United States Patent
Terbrueggen et al.

(10) Patent No.: US 9,745,616 B2
(45) Date of Patent: Aug. 29, 2017

(54) METHODS AND COMPOSITIONS FOR DETECTING TARGET NUCLEIC ACIDS

(75) Inventors: Robert Terbrueggen, Manhattan Beach, CA (US); Yenbou Liu, Arcadia, CA (US); John Ray Childers, Jr., Long Beach, CA (US); Chang Hee Kim, Rancho Palos Verdes, CA (US); Majid R. Abedi, Anaheim, CA (US)

(73) Assignee: DXTERITY DIAGNOSTICS INCORPORATED, Rancho Dominguez, CA (US)

( * ) Notice: Subject to any disclaimer, the term of this patent is extended or adjusted under 35 U.S.C. 154(b) by 146 days.

(21) Appl. No.: 14/118,524

(22) PCT Filed: May 17, 2012

(86) PCT No.: PCT/US2012/038436
§ 371 (c)(1),
(2), (4) Date: Mar. 5, 2014

(87) PCT Pub. No.: WO2012/158967
PCT Pub. Date: Nov. 22, 2012

(65) Prior Publication Data
US 2014/0171338 A1    Jun. 19, 2014

Related U.S. Application Data

(60) Provisional application No. 61/486,817, filed on May 17, 2011.

(51) Int. Cl.
*C12Q 1/68* (2006.01)
*C12N 9/00* (2006.01)
*G01N 33/00* (2006.01)
*C07H 21/04* (2006.01)

(52) U.S. Cl.
CPC ......... *C12Q 1/6813* (2013.01); *C12Q 1/6809* (2013.01); *C12Q 1/6834* (2013.01); *C12Q 1/6855* (2013.01); *C12Q 1/6862* (2013.01)

(58) Field of Classification Search
None
See application file for complete search history.

(56) References Cited

U.S. PATENT DOCUMENTS

| | | | |
|---|---|---|---|
| 4,469,863 A | 9/1984 | Ts'o et al. | |
| 5,034,506 A | 7/1991 | Summerton et al. | |
| 5,185,243 A | 2/1993 | Ullman et al. | |
| 5,216,141 A | 6/1993 | Benner | |
| 5,235,033 A | 8/1993 | Summerton et al. | |
| 5,346,994 A | 9/1994 | Chomczynski | |
| 5,386,023 A | 1/1995 | Sanghvi et al. | |
| 5,476,930 A | 12/1995 | Letsinger et al. | |
| 5,514,546 A | 5/1996 | Kool | |
| 5,602,240 A | 2/1997 | De Mesmaeker | |
| 5,637,684 A | 6/1997 | Cook et al. | |
| 5,644,048 A | 7/1997 | Yau | |
| 5,674,683 A | 10/1997 | Kool | |
| 5,681,943 A | 10/1997 | Letsinger et al. | |
| 5,683,874 A | 11/1997 | Kool | |
| 5,714,320 A | 2/1998 | Kool | |
| 5,780,613 A | 7/1998 | Letsinger et al. | |
| 5,808,036 A | 9/1998 | Kool | |
| 6,077,668 A | 6/2000 | Kool | |
| 6,140,480 A | 10/2000 | Kool | |
| 6,218,108 B1 | 4/2001 | Kool | |
| 6,265,166 B1 | 7/2001 | Frank-Kamenetskii et al. | |
| 6,479,650 B1 | 11/2002 | Kool | |
| 6,511,810 B2 | 1/2003 | Bi et al. | |
| 6,670,193 B2 | 12/2003 | Kool | |
| 6,942,771 B1 | 9/2005 | Kayyem | |
| 6,955,901 B2 | 10/2005 | Schouten | |
| 7,033,753 B1 | 4/2006 | Kool | |
| 7,153,658 B2 | 12/2006 | Anderson et al. | |
| 7,198,900 B2 | 4/2007 | Woudenberg et al. | |
| 2004/0110134 A1 | 6/2004 | Wenz et al. | |
| 2004/0214196 A1 | 10/2004 | Aydin | |
| 2004/0235005 A1 | 11/2004 | Friedlander et al. | |

(Continued)

FOREIGN PATENT DOCUMENTS

| EP | 320308 | 6/1989 |
|---|---|---|
| EP | 439182 | 7/1991 |

(Continued)

OTHER PUBLICATIONS

"Viruses" (Wikipedia.com, accessed Nov. 24, 2012).*
"How many species of bacteria are there" (wisegeek.com; accessed Jan. 21, 2014).*
"Fungi," (Wikipedia.com; accessed Jun. 3, 2013).*
"Plant," (Wikipedia.com; accessed Mar. 8, 2013).*
"Mammal," (Wikipedia.com; accessed Sep. 22, 2011 ).*
"Murinae," (Wikipedia.com, accessed Mar. 18, 2013).*
"List of sequenced bacterial genomes" (Wikipedia.com; accessed Jan. 24, 2014).*
Stern, Rowena F. et al. "Multiplex ligation-dependent probe amplification using a completely synthetic probe set", Biotechniques, vol. 37, No. 3, pp. 399-405 (2004).

(Continued)

*Primary Examiner* — Bradley L Sisson
(74) *Attorney, Agent, or Firm* — Morgan, Lewis & Bockius LLP; Robin M. Silva

(57) ABSTRACT

The present invention provides compositions, apparatuses and methods for detecting one or more nucleic acid targets present in a sample. Methods of the invention include utilizing two or more ligation probes that reversibly bind a target nucleic acid in close proximity to each other and possess complementary reactive ligation moieties. When such probes have bound to the target in the proper orientation, they are able to undergo a spontaneous chemical ligation reaction that yields a ligation product that is directly detected or that is amplified to produce amplicons that are then detected. The present invention also provides methods to stabilize sample RNA so that degradation does not significantly affect the results of the analysis.

17 Claims, 13 Drawing Sheets

(56) References Cited

U.S. PATENT DOCUMENTS

| | | |
|---|---|---|
| 2004/0235154 A1 | 11/2004 | Oh et al. |
| 2004/0259102 A1 | 12/2004 | Kool |
| 2004/0259105 A1 | 12/2004 | Fan et al. |
| 2005/0142545 A1 | 6/2005 | Conn et al. |
| 2005/0208503 A1 | 9/2005 | Yowanto et al. |
| 2005/0208543 A1 | 9/2005 | Vann et al. |
| 2005/0272071 A1 | 12/2005 | Lao et al. |
| 2006/0003351 A1 | 1/2006 | Karger et al. |
| 2006/0024731 A1* | 2/2006 | Barany et al. ............ 435/6 |
| 2006/0063163 A1 | 3/2006 | Chen et al. |
| 2006/0068378 A1 | 3/2006 | Mirkin et al. |
| 2006/0199192 A1* | 9/2006 | Kool et al. ............... 435/6 |
| 2007/0218477 A1* | 9/2007 | Thomas ................... 435/6 |
| 2008/0124810 A1 | 5/2008 | Terbrueggen |
| 2010/0267585 A1 | 10/2010 | Terbrueggen |

FOREIGN PATENT DOCUMENTS

| | | |
|---|---|---|
| EP | 1130113 A1 | 9/2001 |
| WO | WO 89/12696 | 12/1989 |
| WO | WO 90/01069 | 2/1990 |
| WO | WO 92/03576 | 3/1992 |
| WO | WO 92/20702 | 11/1992 |
| WO | WO 94/24143 A1 | 10/1994 |
| WO | WO 94/29485 | 12/1994 |
| WO | WO 95/15971 | 6/1995 |
| WO | WO 96/15271 | 5/1996 |
| WO | WO 96/35699 | 11/1996 |
| WO | WO 96/40712 | 12/1996 |
| WO | WO 97/31256 | 8/1997 |
| WO | WO 97/46568 | 12/1997 |
| WO | WO 98/20162 | 5/1998 |
| WO | WO 99/37819 | 7/1999 |
| WO | WO 01/27326 | 4/2001 |
| WO | WO 01/92579 A2 | 12/2001 |
| WO | WO 01/94638 | 12/2001 |
| WO | WO 02/02823 | 1/2002 |
| WO | WO 2004/005545 A1 | 1/2004 |
| WO | WO 2004/076692 | 9/2004 |
| WO | WO 2007/133703 | 11/2007 |
| WO | WO 2010/114599 | 10/2010 |

OTHER PUBLICATIONS

Abe et al., "Destabilizing Universal Linkers for Signal Amplification in Self-Lighting Probes for RNA" *J. Am. Chem. Soc.* (2004) 126:13980:13986.
Abe et al., "Flow cytometric detection of specific RNAS in native human cells with quenched autoligating FRET probes" *Proc. Natl. Acad. Sci. USA* (2006) 103(2):263-8.
Abramson et al., "Nucleic acid amplification technologies" *Current Opinion in Biotechnology* (1993) 4:41-47.
Arar et al., "Synthesis and Antiviral Activity of Peptide-Oligonucleotide Conjugates Prepared by Using $N_\alpha$ (Bromoacetyl) peptides" *BioConj. Chem.* (1995) 6:573.
Bachmann et al., "Improvement of PCR amplified DNA sequencing with the aid of detergents" *Nucleic Acid Res.* (1990) 18:1309.
Backes et al., "An Alkanesulfonamide 'Safety-Catch' Linker for Solid-Phase Synthesis" *J. Org. Chem.* 64:2322-2330.
Baselt, D.R. et al., "A Biosensor Based on Magnetoresistance Technology", *Biosensors & Bioelectronics*, (1998) 13:731-739.
Beaucage et al., "The Functionalization of Oligonucleotides Via Phosphoramidite Derivatives" *Tetrahedron* (1993) 49(10):1925.
Bibikova, M. et al., "Quantitative Gene Expression Profiling in Formalin-Fixed, Paraffin-Embedded Tissues Using Universal Bead Arrays", *American Journal of Pathology*, (2004) 165:5 1799-1807.
Botti et al., "Chemical Synthesis of Proteins and Circular Peptides Using $N^\alpha$-1(1-Phenyl-2-Mercaptoethyl) Auxiliaries" *Protein Pept. Lett.* (2005) 12(8):729-35.
Brill et al., "Synthesis of Oligodeoxynucleoside Phosphorodithioates via Thioamidites" *J. Am. Chem. Soc.* (1989) 111:2321.

Carlsson et al., "Screening for genetic mutations" *Nature* (1996) 380:207.
Chan et al., "Construction and Characterization of a Heterodimeric Iron Protein: Defining Roles for Adenosine Triphosphate in Nitrogenase Catalysis" *Biochemistry* (2000) 39(24):7221-8.
Cuppolletti et al., "Oligomeric Fluorescent Labels for DNA" *Bioconjug. Chem.* (2005) 16(3):528-34.
Dempcy et al., "Synthesis of a thymidyl pentamer of deoxyribonucleic guanidine and binding studies with DNA homopolynucleotides" *Proc. Natl. Acad. Sci. USA* (1995) 92:6097.
Dill, K. et al., "Immunoassays and Sequence-Specific DNA Detection on a Microchip Using Enzyme Amplified Electrochemical Detection", *J. Biochem. Biophys. Methods*, (2004) 59:181-187.
Dogan et al., "5'-Tethered Stilbene Derivatives as Fidelity-and Affinity-Enhancing Modulators of DNA Duplex Stability" *J. Am. Chem. Soc.* (2004) 126:4762-4763.
Dose et al., "Convergent Synthesis of Peptide Nucleic Acids by Native Chemical Ligation", *Org. Letters* (2005) 7:20 4365-4368.
Dose et al., "Reducing Product Inhibition in DNA-Template-Controlled Ligation Reactions", *Agnew. Chem. Int. Ed.* (2006) 45:5369-5373.
Egholm, M. et al., "Peptide Nucleic Acids (PNA). Oligonucleotide Analogues with an Achiral Peptide Backbone" *J. Am. Chem. Soc.* (1992) 114:1895.
Egholm, M. et al. "PNA Hybridizes to Complementary Oligonucleotides Obeying the Watson-Crick Hydrogen-Bonding Rules", *Nature*, (1993) 365:566-568.
Fan, JB et al., "A Versatile Assay for High-Throughput Gene Expression Profiling on Universal Array Matrices", *Genome Research*, (2004) 14, 878-885.
Ficht et al., "Single-Nucleotide-Specific PNA-Peptide Ligation on Synthetic and PCR DNA Templates", *J. Am. Chem. Soc.* (2004) 126:9970-9981.
Ficht et al. "As Fast and Selective as Enzymatic Ligations: Unpaired Nucleobases Increase the Selectivity of DNA-Controlled Native Chemical PNA Ligation" *ChemBioChem* (2005) 6:2098-2103.
Foss, R.D. et al., "Effects of Fixative and Fixation Time on the Extraction and Polymerase Chain Reaction Amplification of RNA from Paraffin-Embedded Tissue. Comparison of Two Housekeeping Gene mRNA Controls", *Diagn. Mol. Pathol.*, 3(3):148-155 (1994).
Gottesfeld, J.M. et al., "Sequence-specific Recognition of DNA in the Nucleosome by Pyrrole-Imidazole Polyamides" *J. Mol. Biol.* (2001) 309:615-629.
Grossman et al., "High-Density Multiplex Detection of Nucleic Acid Sequences: Oligonucleotide Ligation Assay and Sequence-Coded Separation", *Nucleic Acids Research*, Oxford University Press, Surrey, Great Britain, vol. 22, No. 21, pp. 4527-4534 (1994).
Grossmann et al., "DNA-Catalyzed Transfer of a Reporter Group" *J. Am. Chem. Soc.* (2006) 128:15596-15597.
Gryaznov, S.M. and Letsinger, R.L., "Template controlled coupling and recombination of oligonucleotide blocks containing thiophosphoryl groups" *Nucleic Acids Research* (1993) 21:1403.
Gryaznov et al., "Chemical Ligation of Oligonucleotides in the Presence and Absence of Template", *J. Am. Chem. Soc.*, (1993) 115(9):3808-3809.
Gryaznov et al., "Enhancement of Selectivity in Recognition of Nucleic Acids via Chemical Autoligation", *Nucleic Acids Res.*, (1994) 22:2366-2369.
Herrlein and Letsinger, "A Covalent Lock for Self-Assembled Oligonucleotide Conjugates", *J. Am. Chem. Soc.*, (1995) 117:10151-10152.
Horn et al., "Oligonucleotides with Alternating Anionic and Cationic Phosphoramidate Linkages: Synthesis and Hybridization of Sterio-uniform Isomers", *Tetrahedron Letters* (1996) 37:743.
Jeffs et al., "Unusual conformation of a 3'-thioformacetal linkage in a DNA duplex" *J. Biomolecular NMR* (1994) 34:17.
Jenkins et al., "The Biosynthesis of Carbocyclic Nucleosides" *Chem. Soc. Rev.* (1995) pp. 169-176.
Karim et al., "Convenient genotyping of six myostatin mutation causeing double-muscling in cattle using a multiplex oligonucleotide ligation assay", *Animal Genetics*, vol. 31, No. 6, pp. 396-399 (2000).

(56) References Cited

OTHER PUBLICATIONS

Kenner, G.W., "The Safety Catch Principle in Solid Phase Peptide Synthesis", *J. Chem. Soc.* (1971) pp. 636-637.
Kiedrowski et al., "Parabolic Growth of a Self-Replicating Hexadeoxynucleotide Bearing a 3'5'-Phosphoamidate Linkage" *Agnew. Chem. Intl. Ed.* English (1991) 30:423.
Kool, E.T. et al., "Convergent DNA synthesis: a non-enzymatic dimerization approach to circular oligodeoxynucleotides" *Nucleic Acid Res.* (1995) 23 (17):3547.
Koshkin et al., "LNA (Locked Nucleic Acid): An RNA Mimic Forming Exceeingly Stable LNA:LNA Duplexes" *J. Am. Chem. Soc.* (1998) 120:13252-3.
Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition" *Tetrahedron* (1998) 54:3607-3630.
Kutyavin et al., "Oligonucleotides with conjugated dihydropyrroloindole tripeptides: base composition and backbone effects on hybridization" *Nucleic Acids Research* (1997) vol. 25, No. 18: 3718-3723.
Kutyavin et al., "3'-Minor groove binder-DNA probes increase sequence specificity at PCR extension temperatures" *Nucleic Acids Research* (2000) vol. 28, No. 2:655-661.
Landegren, U. "Ligation-based DNA Diagnostics" *Bioessays* (1993) 15(11):761-5.
Landegren, U. et al., "A Ligase-Mediated Gene Detection Technique", *Science*, (1988) 241(4689):1077-1080.
Letsinger et al., "Phosphoramidate Analogs of Oligonucleotides" *J. Org. Chem.* (1970) 35:3800.
Letsinger et al., *Nucl. Acids Res.* (1986) 14:3487.
Letsinger et al., "Cationic Oligonucleotides" *J. Am. Chem. Soc.* (1988) 110:4470.
Letsinger et al., "Hybridization of Alternating Cationic/Anionic Oligonucleotides to RNA Segments", *Nucleotide and Nucleoside* (1994) 13:1597.
Liu, R. et al., "Fully Integrated Miniature Device for Automated Gene Expression DNA Microarray Processing", *Anal. Chem.*, (2006) 78(6):1980-1986.
Luebke and Dervan, "Nonenzymatic Sequence-Specific Ligation of Double-Helical DNA", *J. Am. Chem. Soc.*, (1991) 113:7447-7448.
Luebke, K.J. and Dervan, P.B., "Nonenzymatic Ligation of Oligodeoxyribonucleotides no a Duplex DNA Template by Triple-Helix Formation", *J. Am. Chem. Soc.* (1989) 111:8733.
Mag et al., "Synthesis and selective cleavage of an oligodeoxynucleotide containing a bridged internucleotide 5'-phosphorothioate linkage", *Nucleic Acids Res.* (1991) 19:1437-1441.
Marshall et al., "DNA Chips: An Array of Possibilities", *Nat Biotechnol.* (1998) 16(1):27-31.
Martel et al., (High Throughput Genomics) "Multiplex Screening Assay for mRNA Combining Nuclease Protection with Luminescent Array Detection," *Assay and Drug Development Technologies* 1:61-71 (2002).
Meier et al., "Peptide Nucleic Acids (PNAs)—Unusual Properties of Nonionic Oligonucleotide Analogues" *Chem. Int. Ed. Engl.* (1992) 31:1008.
Mesmaeker et al., "Comparison of Rigid and Flexible Backbones in Antisense Oligonucleotides", *Bioorganic & Medicinal Chem. Lett.* (1994) 4:395.
Metelev, V.G. et al., "Oligodeoxyribonucleotides With Internucleotidic or Terminal Phosphorothioate Groups: Different Pathways in the Reaction with Water-Soluble Carbodimide", *Nucleosides & Nucleotides* (1999) 18:2711.
Miller, G.P. et al., "New, stronger nucleophiles for nucleic acid-templated chemistry: Synthesis and application in fluorescence detection of cellular RNA", *Bioorganic and Medicinal Chemistry* (2008) 16:56-64.

Moran et al., "A thymidine triphospate shape analog lacking Watson-Crick pairing ability is replicated with high sequence selectivity", *Proc. Natl. Acad. Sci. USA* (1997) 94(20):10506-11.
Narayanan et al., "Clamping down on weak terminal base pairs: oligonucleotides with molecular caps as fidelity-enhancing elements at the 5'- and 3'-terminal residues", *Nucleic Acids Research* (2004) 32:2901-2911.
Nickerson, "Gene probe assays and their detection", *Current Opinion in Biotechnology* (1993) 4:48-51.
Nilsson, M. et al., "RNA-Templated DNA Litigation for Transcript Analysis", *Nucleic Acids Research*, 29:2 578-581 (2001).
Offer et al., "Extending Synthetic Access to Proteins with a Removable Acyl Transfer Auxiliary", *J. Am. Chem. Soc.* (2002) 124(17):4642-6.
Ollivier et al., "Fmoc Solid-Phase Synthesis of Peptide Thioesters Using an Intramolecular N,S-Acyl Shift" *Organic Letters* (2005) vol. 7, No. 13, pp. 2647-2650.
Pauwels et al., "Biological Activity of New 2-5A Analogues", *Chemica Scripta* (1986) 26:141.
Pooga, M. et al., "PNA oligomers as tools for specific modulation of gene expression", *Biomolecular Engineering* (2001) 17:183-192.
Pritchard et al., "Effects of Base Mismatches on Joining of Short Oligonucleotides by DNA Ligases", *Nucleic Acids Res.* (1997) 25(17):3403-7.
Rawls, R., "Optimistic About Antisense" *C & E* News (Jun. 2, 1997), p. 35-39.
Sando et al., "Nonenzymatic DNA ligation in *Escherichia coli* cells", *Nucleic Acids Res. Suppl.* (2002) 2:121-2.
Sando et al., "Quencher as Leaving Group: Efficient Detection of DNA-Joining Reactions", *J. Am. Chem. Soc.* (2002) 124(10)2096-7.
Sando et al., "Imaging of RNA in Bacteria with Self-Ligating Quenched Probes", *Journal Am. Chem.* (2002) 124(33):9686-7.
Sando et al., "Quenched Auto-Ligating DNAs: Multicolor Identification of Nucleic Acids at Single Nucleotide Resolution", *J. Am. Chem. Soc.* (2004) 126(4):1081-7.
Sawai et al., "Synthesis and Properties of Oligoadenylic Acids Contaiing 2'-5' Phosphoramide Linkage", *Chem. Lett.* (1984) 805.
Schafer et al., "DNA variation and the future of human genetics", *Nature Biotechnology* (1993) 16:33-39.
Schouten et al., "Relative quantification of 40 nucleic acid sequences by multiplex ligation-dependent probe amplification", *Nucleic Acid Research*, Oxford University Press, Great Britain, vol. 30, No. 12 (2002).
Shabarova, Z.A., et al., "Chemical ligation of DNA: the first non-enzymatic assembly of a biologically active gene", *Nucleic Acids Research* (1991) 19:4247.
Silverman et al., "Quenched autoligation probes allow discrimination of live bacterial species by single nucleotide differences in rRNA", *Nucleic Acids Res.* (2005) 33(15):4978-86.
Silverman et al., "Detecting RNA and DNA with Templated Chemical Reactions", *Chem. Rev.*, (2006) 106:3775-3789.
Sprinzl et al., "Enzymatic Incorporation of ATP and CTP Analogues into the 3' End of Trna", *Eur. J. Biochem.* (1977) 81:579.
Steemers, F.J. et al., "Screening Unlabeled DNA Targets with Randomly Ordered Fiber-Optic Gene Arrays", *Nat Biotechnol.* (2000) 18(1):91-4.
Stern et al., "Multiplex ligation-dependent probe amplification using a completely synthetic probe set", *Biotechniques*, vol. 37, No. 3, pp. 399-405 (2004).
Stetsenko and Gait, "Efficient Conjugation of Peptides to Oligonucleotides by 'Native Ligation'", *J. Org. Chem.* (2000) 65(16):4900-8.
Ueno, Y. et al., "Nucleosides and Nucleotides. 165. Chemical Ligation of Oligodeoxynuclotides Having a Mercapto Group at the 5-Position of 2'-Deoxyuridine Via a Disulfide Bond" *Nucleosides and Nucleotides*, Marcel Dekker Inc., vol. 17, No. 1-3 (1998) pp. 283-289.
Umek, R.M. et al., "Electronic Detection of Nucleic Acids—A Versatile Platform for Molecular Diagnostics", *J. Molecular Diagnostics*, (2001) 3:74-84.
Van Eijk, M.J.T., "SNPWaveTM: a flexible multiplexed SNP genotyping technology", *Nucleic Acids Research*, vol. 32, No. 4 (2004).

(56) References Cited

OTHER PUBLICATIONS van't Veer, L.J., et al., "Gene Expression Profiling Predicts Clinical Outcome of Breast Cancer", *Nature*, (2002) 415(6871):530-536 (2002).

Wahlestedt C. et al., "Potent and nontoxic antisense oligonucleotides containing locked nucleic acids", *PNAS* (2000) 97:5633-5638.

Wang et al., "Large-Scale Identification, Mapping, and Genotyping of Single-Nucleotide Polymorphisms in the Human Genome", *Science* (1998) 280:1077.

Warren et al., "Toward Fully Synthetic Glycoproteins by Ultimately Convergent Routs: A Solution to a Long-Standing Problem", *J. Am. Chem. Soc.* (2004) 126(21):6576-82.

Weizmann, Y. et al., "Magneto-Mechanical Detection of Nucleic Acids and Telomerase Activity in Cancer Cells", *J. Am. Chem. Soc.*, (2004) 126:1073-1080.

Wengel, J. et al., "LNA (Locked Nucleic Acid)", *Nucleosides & Nucleotides*, (1999) 18:1365-1370.

Wu, D.Y. et al., "The Ligation Amplification Reaction (LAR)-Amplification of Specific DNA Sequences Using Sequential Rounds of Template-Dependent Ligation", *Genomics* (1989) 4(4):560-9.

Xu et al., "Chemical and enzymatic properties of bridging 5'-S-phosphorothioester linkages in DNA", *Nucleic Acid Res.* (1998) 26(13):3159-64.

Xu et al., "Nonenzymatic Autoligation in Direct Three-Color Detection of RNA and DNA Point Mutations" *Nature Biotechnology* (2001) 19(2):148-52.

Xu and Kool, E.T., "A Novel 5'-Iodonucleoside Allows Efficient Nonenzymatic Ligation of Single-stranded and Duplex DNAs", *Tetrahedron Letters* (1997) 38:5595.

Xu and Kool, E.T., "High sequence fidelity in a non-enzymatic DNA autoligation reacation", *Nucleic Acid Research* (1999) 27:875.

Yang et al., "Badge, Beads Array for the Detection of Gene Expression, a High Throughput Diagnostic Bioassay", *Genome Research* (2001) 11(11):1888-98.

Yeakley, JM et al., "Profiling Alternative Splicing on Fiber-Optic Arrays", *Nature Biotechnology*, (2002) 20:353-358.

Castiglioni et al., "Development of a Universal Microarray Based on the Ligation Detection Reaction and 16S rRNA Gene Polymorphism to Target Diversity of Cyanobacteria", Applied and Environmental Microbiology, vol. 70, No. 12, pp. 7161-7172 (2004).

\* cited by examiner 2-probe system 3-probe system

CPG = Control Pore Glass
DMT = bis-(4-methoxyphenyl)phenylmethyl

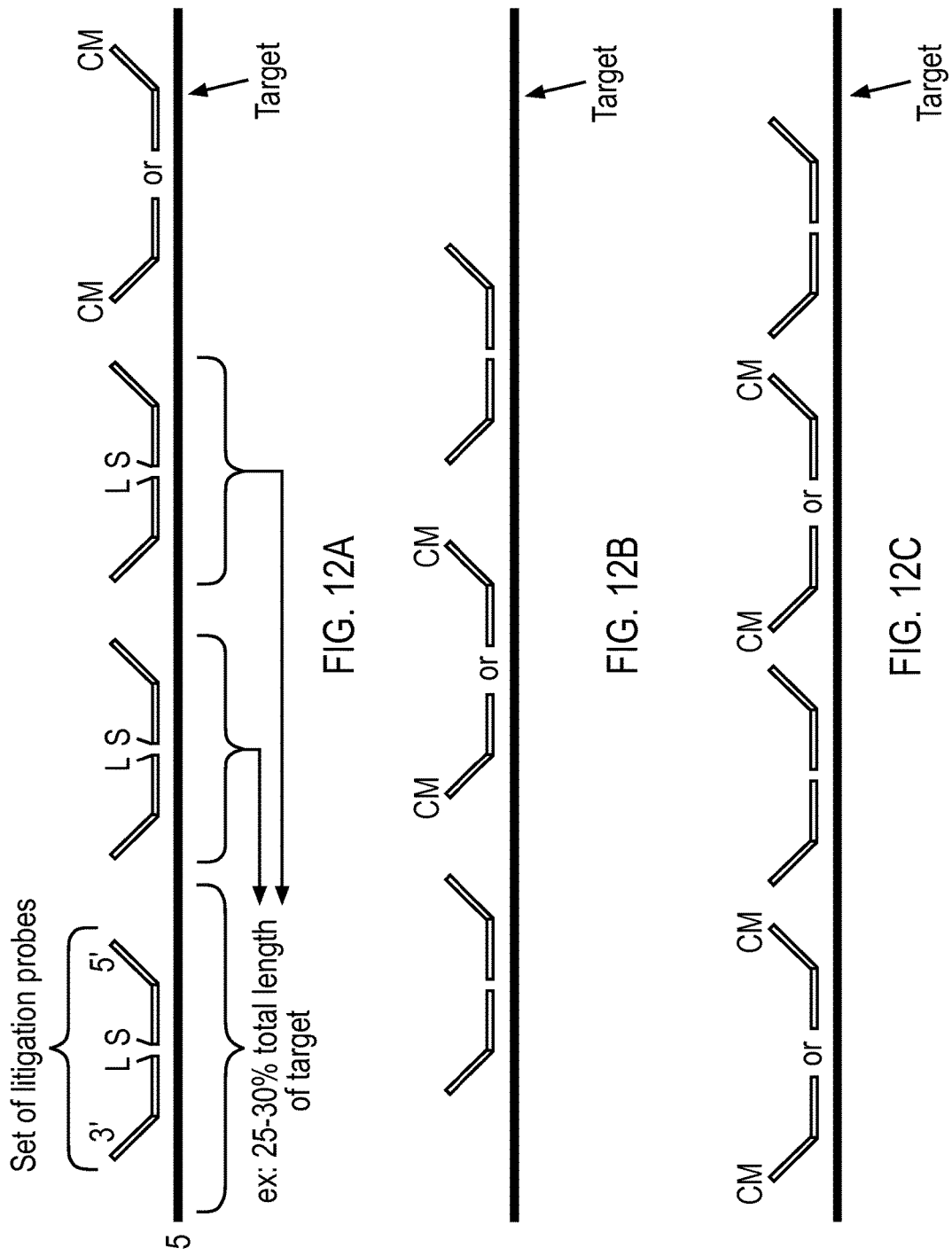

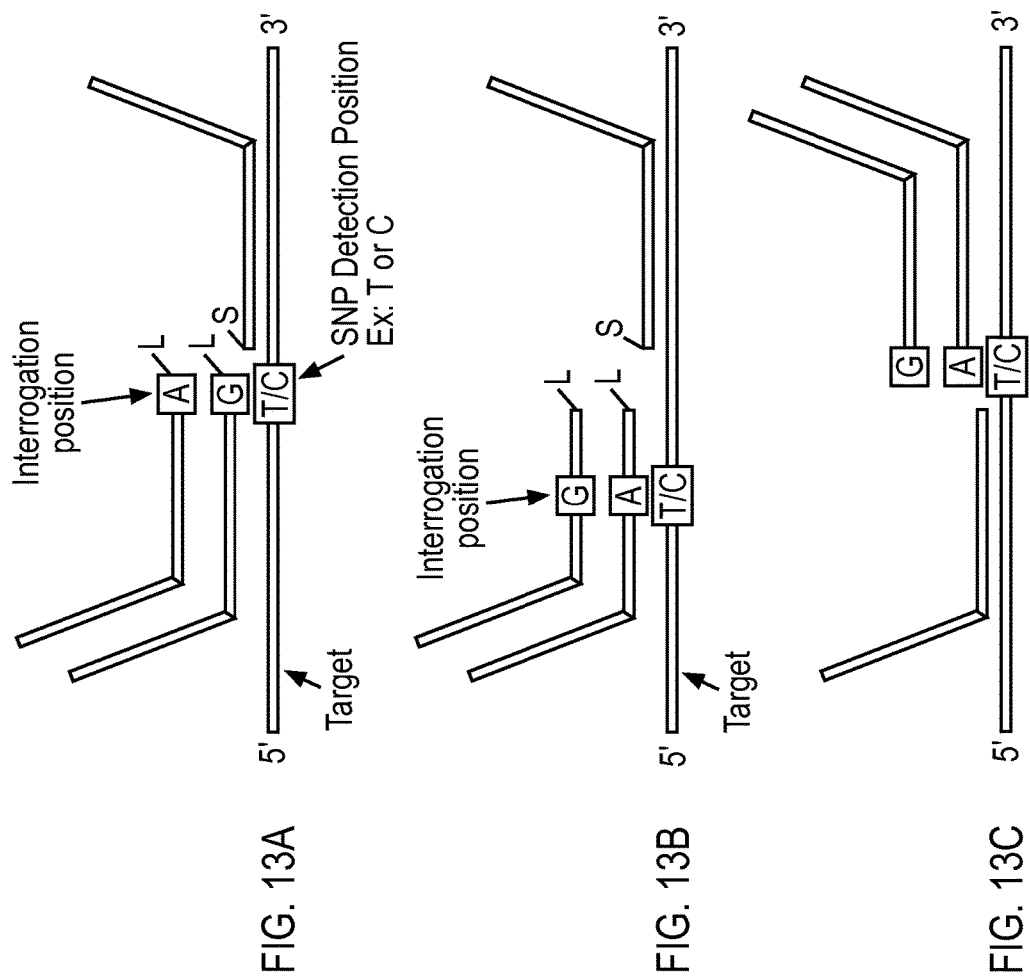

METHODS AND COMPOSITIONS FOR DETECTING TARGET NUCLEIC ACIDS

CROSS REFERENCE TO RELATED APPLICATIONS

This application is a 371 National Phase of International Application No. PCT/US2012/038436 filed May 17, 2012 which claims priority to U.S. Provisional Patent Application No. 61/486,817, filed on May 17, 2011, each of which is hereby incorporated by reference in its entirety.

STATEMENT REGARDING FEDERALLY SPONSORED RESEARCH

This invention was made with government support under Grant No. 1R43HG006656-01 awarded by the Small Business Innovation Research (SBIR) program. The government has certain rights in the invention.

BACKGROUND OF THE INVENTION

The detection of specific nucleic acids is an important tool for diagnostic medicine and molecular biology research. Gene probe assays currently play a role in a number of spheres of diagnostic medicine and molecular biology, including for example identifying infectious organisms such as bacteria and viruses, in probing the expression of normal and mutant genes and identifying genes associated with disease or injury, such as oncogenes, in typing tissue for compatibility preceding tissue transplantation, in matching tissue or blood samples for forensic medicine, for responding to emergency response situations like a nuclear incident or pandemic flu outbreak, in determining disease prognosis or causation, and in exploring homology among genes from different species.

Ideally, a gene probe assay should be sensitive, specific and easily automatable. The requirement for sensitivity (i.e. low detection limits) has been greatly alleviated by the development of the polymerase chain reaction (PCR) and other amplification technologies which allow researchers to exponentially amplify a specific nucleic acid sequence before analysis. For example, multiplex PCR amplification of SNP loci with subsequent hybridization to oligonucleotide arrays can be used to simultaneously genotype hundreds of SNPs.

Specificity is a challenge for gene probe assays. The extent of molecular complementarity between probe and target defines the specificity of the interaction. Variations in composition and concentrations of probes, targets and salts in the hybridization reaction as well as the reaction temperature, and length of the probe may all alter the specificity of the probe/target interaction. It can be possible under some circumstances to distinguish targets with perfect complementarity from targets with mismatches, although this is generally difficult using traditional technology, since small variations in the reaction conditions will alter the hybridization. Techniques for mismatch detection include probe digestion assays in which mismatches create sites for probe cleavage, and DNA ligation assays where single point mismatches prevent ligation.

A variety of enzymatic and non-enzymatic methods are available for detecting sequence variations. Examples of enzyme based methods include Invader™, oligonucleotide ligation assay (OLA) single base extension methods, allelic PCR, and competitive probe analysis (e.g. competitive sequencing by hybridization). Enzymatic DNA ligation reactions are well known in the art and have been used extensively in SNP detection, enzymatic amplification reactions and DNA repair. A number of non-enzymatic or template mediated chemical ligation methods can also be used to detect sequence variations. These include chemical ligation methods that utilize coupling reagents, such as N-cyanoimidazole, cyanogen bromide, and 1-ethyl-3-(3-dimethylaminopropyl)-carbodiimide hydrochloride.

A widely recognized problem when analyzing RNA for genetic studies is the inherent instability of the RNA itself. RNA naturally has a short lifetime in living organisms because organisms regulate the RNA concentration which regulates downstream processes which are dependent on the RNA. There are also many natural processes which lead to the destruction of an RNA.

In recent years researchers have spent considerable effort developing methods for the analysis of gene expression in cells. This is generally accomplished by analyzing the cell contents for the amount of specific mRNA molecules present. Measurements of gene expression are based on the underlying assumption that the analyzed RNA sample closely resembles the number of transcripts in vivo. Hence, maintaining the integrity of the RNA after extraction from the cell is of paramount importance. Researchers have recognized that transcripts of different genes (mRNA) possess different stabilities which implies that that degradation of RNA occurring during the isolation procedure may be non-uniformly distributed among different RNA molecules. One comparison of RNA samples of different degrees of degradation shows that up to 75% of microarray-based measurements of differential gene expression can be caused by degradation bias. Auer H, Liyanarachchi S, Newsom D, Klisovic M I, Marcucci G, Kornacker K (2003), *Nature Genetics* 35:292-293.

There remains a need for methods and compositions for efficient and specific nucleic acid detection and for stabilization of RNA following extraction from cells.

BRIEF SUMMARY OF THE INVENTION

Accordingly, the present invention provides methods and compositions for non-enzymatic chemical ligation reactions which provides rapid target detection and greatly simplified processes of detecting and measuring target nucleic acids.

In one aspect, the present invention provides a method for detecting a plurality of different target nucleic acids in a sample, wherein each target nucleic acid comprises a first target domain adjacent to a second target domain and a third target capture domain located upstream or downstream from the first and second target domains. The method comprises the steps of (a) providing a plurality of ligation substrates each comprising one of the target nucleic acids; a first set of ligation probes comprising (i) a first nucleic acid ligation probe comprising a first probe domain hybridized to a first target domain of the one target nucleic acid sequence and a 5'-ligation moiety; and (ii) a second nucleic acid ligation probe comprising a second probe domain hybridized to a second target domain of the one target nucleic acid sequence and a 3' ligation moiety; (b) ligating the first and second ligation probes without the use of a ligase enzyme to form a first plurality of ligation products; (c) hybridizing target capture probes comprising a capture moiety to the third target domain of the target nucleic acids to form target complexes; (d) capturing the target complexes on a surface using the capture moiety; amplifying the ligation products to form amplicons; and (f) detecting the amplicons, thereby detecting the target nucleic acids.

In a further embodiment and in accordance with the above, the target nucleic acids further comprise a fourth target domain adjacent to a fifth target domain and the plurality of ligation substrates each further comprises a second set of ligation probes comprising a third nucleic acid ligation probe hybridized to the fourth target domain and a fourth nucleic acid ligation probe hybridized to the fifth target domain. In such embodiments, the method further comprises the steps of ligating the third and fourth ligation probes in the absence of a ligase enzyme such that the one target nucleic acid sequence comprises multiple ligation products and the detecting step (f) comprises detecting amplicons generated from the multiple ligation products.

In a further embodiment and in accordance with any of the above, the target nucleic acids further comprise a sixth target domain adjacent to a seventh target domain, the plurality of ligation substrates each further comprises a third set of ligation probes comprising a fifth nucleic acid ligation probe hybridized to the sixth target domain and a sixth nucleic acid ligation probe hybridized to the seventh target domain, and the method further comprises ligating the third and fourth ligation probes in the absence of a ligase enzyme such that the one target nucleic acid sequence comprises multiple ligation products.

In a still further embodiment and in accordance with any of the above, each of the ligation probes further comprises a primer sequence.

In a still further embodiment and in accordance with any of the above, at least one of the ligation probes of each set of ligation probes further comprises a variable spacer sequence such that the amplicons have a target specific length.

In a yet further embodiment and in accordance with any of the above, only one ligation probe of each set of ligation probes comprises the variable spacer sequence.

In a yet further embodiment and in accordance with any of the above, the variable spacer sequence is contained between the probe domain and the primer of the ligation probe.

In a further embodiment and in accordance with any of the above, the capture moiety of the target capture probe comprises a member selected from: a capture nucleic acid sequence, a bead and a binding partner of a binding partner pair.

In a further embodiment and in accordance with any of the above, the 5' ligation moiety comprises DABSYL and the 3' ligation moiety comprises phosphorothioate.

In a further embodiment and in accordance with any of the above, the 3' ligation moiety comprises DABSYL.

In a further embodiment and in accordance with any of the above, the sample was collected into a buffer comprising guanidinium hydrochloride (GuHCl). In an exemplary embodiment, the sample is blood.

In a further embodiment and in accordance with any of the above, the target nucleic acids comprise DNA or RNA.

In a still further embodiment and in accordance with any of the above, the detecting step (f) utilizes a technique selected from the group consisting of capillary electrophoresis, mass spectrometry, microarray analysis, sequencing, real-time PCR, optical detection, fluorescence detection, bioluminescence detection, chemiluminescence detection, electrochemical detection, electrochemiluminescence detection and lateral flow detection.

In a further embodiment and in accordance with any of the above, the hybridizing step (c) occurs simultaneously with the ligating step (b).

In a further aspect and in accordance with any of the above, the present invention provides a method of detecting a plurality of different target nucleic acids in a sample, wherein each target sequence comprises an adjacent first and a second target domain, the method comprising: (a) providing a plurality of ligation substrates each comprising one of the different target nucleic acids, a first nucleic acid ligation probe comprising a first probe domain complementary to a first target domain of the one target nucleic acid, a first primer sequence; and a 5'-ligation moiety; and a second nucleic acid ligation probe comprising: a second probe domain complementary to a second target domain of the one target nucleic acid, a second primer sequence, and a 3' ligation moiety. One of the ligation probe comprises a variable spacer sequence. The method further comprises the steps of (b) ligating the first and second ligation probes in the absence of a ligase enzyme to form a plurality of different ligation products, wherein different ligation products have different target specific lengths; (c) amplifying the ligation product; and (d) detecting the presence of the different ligation products on the basis of the different target lengths.

In a further embodiment and in accordance with any of the above, the target nucleic acid sequences are RNA or DNA.

In a further embodiment and in accordance with any of the above, the sample is derived from blood.

In a still further embodiment and in accordance with any of the above, the sample is derived from paraffin embedded samples.

In a yet further embodiment and in accordance with any of the above, the detecting is by capillary electrophoresis or by mass spectrometry.

In a further embodiment and in accordance with any of the above, each of the first primers are the same and each of the second primers are the same.

In further aspects and in accordance with any of the above, the present invention provides a kit for detecting a target nucleic acid sequence, wherein the target sequence comprises an adjacent first and a second target domain, the kit comprising: (a) 2× lysis buffer comprising 6 M GuHCl; (b) a first ligation probe comprising: (i) a first probe domain complementary to the first target domain; (ii) a first primer sequence; and (iii) a 5'-ligation moiety; and (c) a second nucleic acid ligation probe comprising: (i) a second probe domain complementary the second target domain; (ii) a second primer sequence; and (iii) a 3' ligation moiety.

In a further embodiment and in accordance with any of the above, one or both of the ligation probes further comprise a variable spacer sequence.

In a further aspect and in accordance with any of the above, the present invention provides a method of detecting a plurality of different target nucleic acids in a sample, wherein each target sequence comprises an adjacent first and a second target domain, the method comprising: (a) providing a reaction mixture comprising: (i) a target sample comprising blood; and (ii) 1× lysis buffer comprising 3 M GuHCl; (b) contacting the reaction mixture with a plurality of different probes sets, each probe set comprising: (i) a first ligation probe comprising: (1) a first probe domain complementary to a first target domain of the one target nucleic acid; (2) a first primer sequence; and (3) a 5'-ligation moiety; and (iii) a second nucleic acid ligation probe comprising: (1) a second probe domain complementary to a second target domain of the one target nucleic acid; (2) a second primer sequence; and (3) a 3' ligation moiety; (d) ligating the first and second ligation probes in the absence of a ligase enzyme to form a plurality of different ligation products; (e) amplifying the different ligation products; and (f) detecting the presence of the ligation products.

In a further embodiment and in accordance with any of the above, the ligation probes further comprises a variable spacer sequence.

In a further embodiment and in accordance with any of the above, the target nucleic acids are RNA.

In a further embodiment and in accordance with any of the above, one of the first and second ligation probes further comprises one of a binding partner pair, and prior to amplifying, a bead comprising the other binding pair is added to capture the ligated products.

In a further embodiment and in accordance with any of the above, the detecting is done using the variable spacer sequence.

In a further aspect and in accordance with any of the above, the present invention provides a method for detecting a plurality of target RNA sequences in a sample, where each target nucleic acid sequence comprises an adjacent first and second target domain and a third target domain. The method includes the steps of collecting a sample into a buffer to form a stabilized sample; conducting an assay in accordance with any of the above in the stabilized sample to detect the plurality of target nucleic acids.

In a further embodiment and in accordance with any of the above, the sample is stable for at least 1 week at ambient room temperature.

BRIEF DESCRIPTION OF THE DRAWINGS

FIG. 12A-C is a further schematic illustration of possible orientations of one embodiment of the present invention, which can find particular use in assessing sample integrity. FIG. 12A depicts a similar orientation to FIG. 11, except with the capture probe(s) "downstream" of the ligation probe sets. CM is a capture moiety. As will be appreciated by those in the art, the CM can be on either the 3' or 5' terminus of the capture probe, although it usually is depicted on the 3' end. In addition, the portion of each ligation probe that does not hybridize to a target domain can contain a number of different functionalities, including, but not limited to, primer binding domains, size tags, capture sequences, etc., as is shown in FIG. 11. FIG. 12A shows a situation where the ligation probe sets are spaced over the length of the target in roughly 25-30% increments for a sample integrity assessment. As will be appreciated by those in the art and described below, the spacing of the different ligation probe sets can vary as needed. FIG. 12B depicts an alternative orientation. FIG. 12C depicts an orientation that can be used both for integrity assessment or redundancy.

FIG. 13A-C depict several schematic of embodiments of the invention for use in SNP detection.

DETAILED DESCRIPTION OF THE INVENTION

Figure 1:
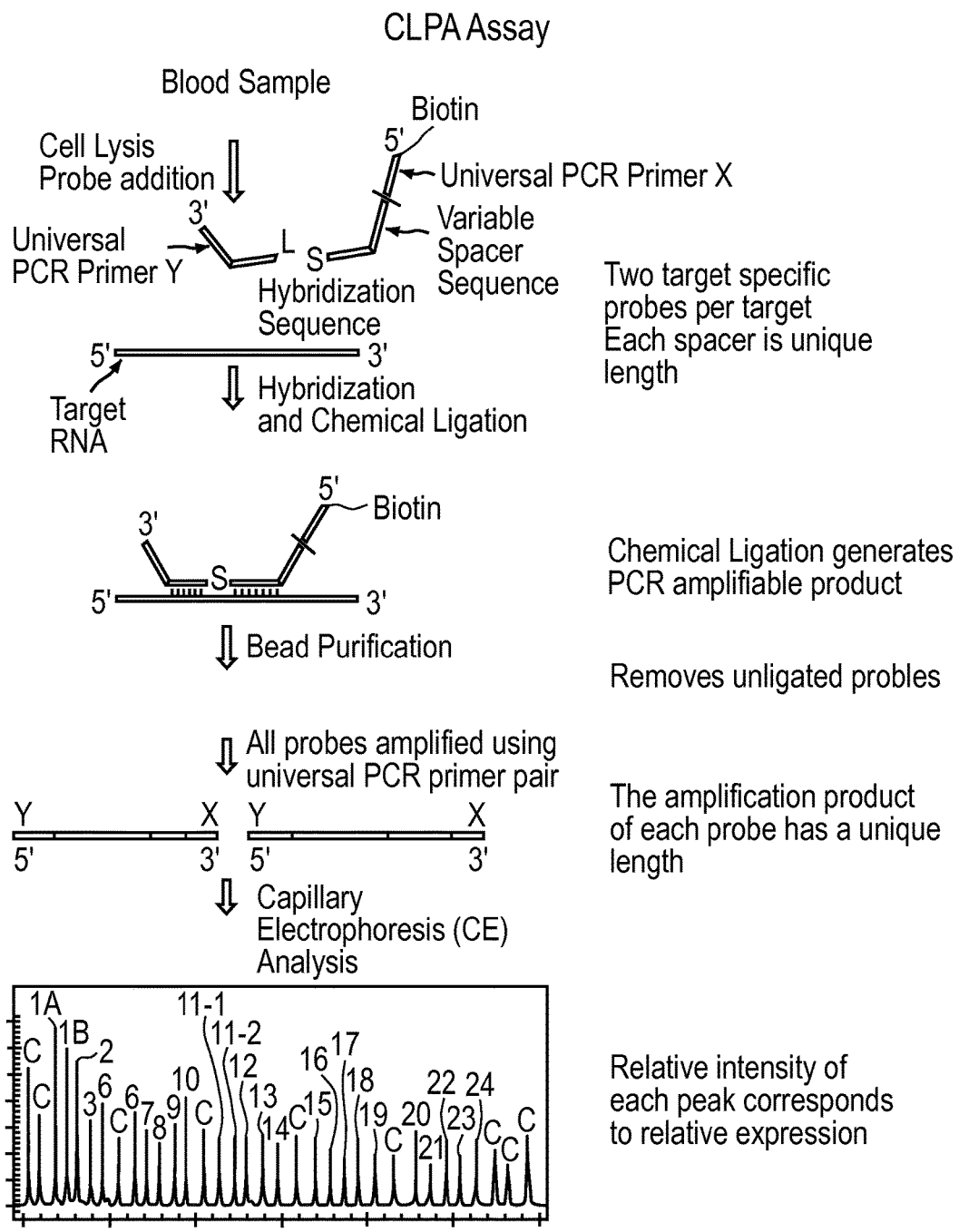
FIG. 1 is a schematic representation of one embodiment of the CLPA-CE assay.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, phage display, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995) *Biochemistry* (4th Ed.) Freeman, New York, Gait, *"Oligonucleotide Synthesis: A Practical Approach"* 1984, IRL Press, London, Nelson and Cox (2000), *Lehninger, Principles of Biochemistry* $3^{rd}$ Ed., W. H. Freeman Pub., New York, N.Y. and Berg et al. (2002) *Biochemistry*, $5^{th}$ Ed., W. H. Freeman Pub., New York, N.Y., all of which are herein incorporated in their entirety by reference for all purposes.

Note that as used herein and in the appended claims, the singular forms "a," "an," and "the" include plural referents unless the context clearly dictates otherwise. Thus, for example, reference to "a polymerase" refers to one agent or mixtures of such agents, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, compositions, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". The term "about" also includes the exact value "X" in addition to minor increments of "X" such as "X+0.1" or "X−0.1." It also is to be understood, although not always explicitly stated, that the reagents described herein are merely exemplary and that equivalents of such are known in the art.

I. Overview

The present invention includes methods and compositions for detecting target nucleic acids in a sample. In general, target nucleic acids are detected through methods that include a step of chemical ligation in which two ligation probes hybridized to adjacent domains of a target nucleic acid are ligated without the use of an exogenous ligase enzyme.

The invention provides methods utilizing two or more ligation probes (also referred to herein as "oligonucleotide probes") that reversibly bind a target nucleic acid in close proximity to each other and possess complementary reactive ligation moieties. In the ligation reaction, when the probes have bound to the target in the proper orientation, they are able to undergo a spontaneous chemical ligation reaction that yields a ligated oligonucleotide product that does not rely on the use of a ligase enzyme. The presence of the target(s) of interest can then be determined by measuring the presence or amount of ligated oligonucleotide product (also referred to herein as a "ligation product") in a number of different ways. As is described below, the ligation probes can contain a variety of additional functionalities, including, but not limited to, detectable labels to aid in the identification, quantification or detection of the ligated oligonucleotide product, including, for example, direct labels such as optical, and electrochemical labels, etc. as more fully described below, variable spacer sequences or "size tags" comprising nucleic acid sequences that are sized to be specific for a particular target, such that detecting ligation products (or amplicons generated from such ligation products) of a particular size identifies the presence and/or amount of a particular target nucleic acid sequence. Another optional functionality for inclusion in one or more of the ligation probes are capture moieties designed for subsequent capture on a solid support (e.g. microarrays, microbeads, nanoparticles, etc.), which include, but are not limited to, binding partners such as biotin, anchoring oligonucleotide sequences (also referred to herein as "anchor sequences" or "capture sequences") molecular handles that promote the concentration or manipulation of the ligated product (magnetic particles, oligonucleotide coding sequences), and promoter and primer sequences to facilitate subsequent secondary amplification of the ligated product via an enzyme like a DNA or RNA polymerase.

Preferably, the ligation reactions of the invention do not require the presence of exogeneously added ligases, nor additional enzymes, although some secondary reactions may rely on the use of enzymes such as polymerases, as described below. Amplification of the target may also include turnover of the ligation product, in which the ligation product has a lower or comparable affinity for the template or target nucleic acid than do the separate ligation probes. Thus, upon ligation of the hybridized probes, the ligation product is released from the target, freeing the target to serve as a template for a new ligation reaction. Alternatively, thermal cycling can be done to remove a ligation product from the target sequence and allow new ligation probes to hybridize for another cycle of ligation.

The invention provides compositions, apparatus and methods for the detection of one or more nucleic acid targets in a sample including, but not limited to, DNA and RNA targets. Advantages of using non-enzymatic approaches for nucleic acid target detection include lower sensitivity to non-natural DNA analog structures, ability to use RNA target sequences and lower cost and greater robustness under varied conditions. In particular, the methods described herein do not require significant sample preparation; that is, the ligation reactions can be performed in the presence of contaminants and buffers that would inhibit or inactivate enzymatic processes for detection. For example, blood samples can be collected into highly denaturing stabilization buffers, the probes added and the reactions occur, under conditions that would denature an enzymatic process. This ability to analyze target nucleic acids, particularly RNA, in impure samples is of particular use in applications such as medical diagnostics (including gene expression profiling and SNP detection), forensic applications, and testing for damage due to environmental toxins and/or radiation. In addition, methods and compositions of the present invention are useful in detection of nucleic acids from samples that are degraded, including paraffin-embedded samples in which the process of fixing and embedding in paraffin resulted in degradation of the samples' nucleic acids.

Figure 11:
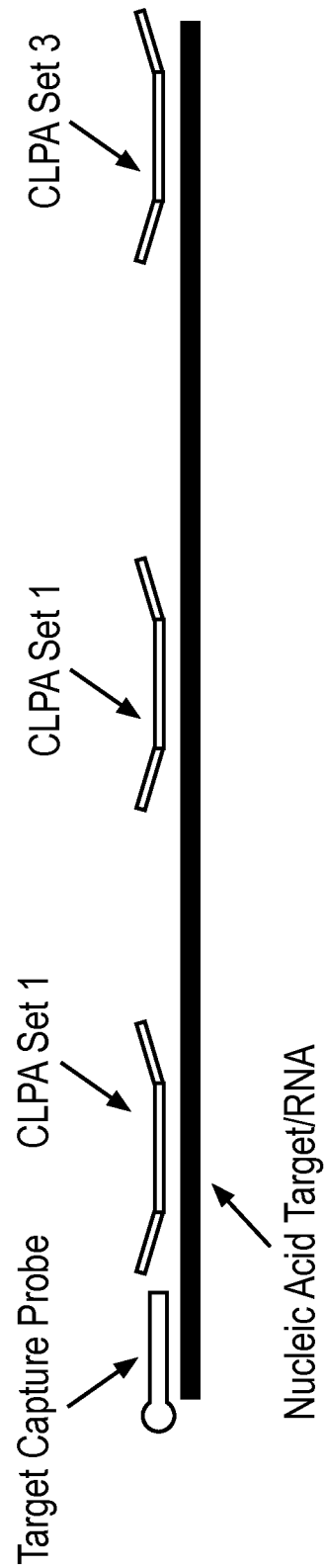
FIG. 11 is a schematic illustration of multiple, unique CLPA probe sets that are bound to the sample target along with a single target capture probe.

In addition, one embodiment of the invention provides for assays relating to target nucleic acid "integrity". That is, as is known in the art with mRNA, for example, or nucleic acids in fixed samples, the nucleic acids are degraded over time. As is shown in FIG. 11 and FIG. 12 and more fully described below, the present invention allows for the use of multiple ligation complexes to allow for an assessment of the integrity of the sample. Similarly, the use of these multiple ligation complexes per target sequence can also be used for data and assay integrity through redundancy, similar to running samples in duplicate or triplicate, for example.

In further aspects, the present invention provides buffers that serve to stabilize nucleic acids in a sample. Such buffers in general include a denaturant comprising a chaotropic cation, including in a non-limiting embodiment, guanidinium hydrochloride. In specific embodiments of the invention, a sample is collected directly into a buffer of the invention, and then subsequent hybridization and ligation of ligation probes is conducted in that buffer without need of purification of the nucleic acids from the sample. In certain embodiments, the sample collected into the buffer is first diluted and then subsequently methods described herein of hybridizing and ligating two or more ligation probes are conducted within that diluted sample without need of purification of the target nucleic acids in the sample.

As discussed above, ligation probes of the invention are hybridized to a target nucleic acids and then ligated without the use of a ligase enzyme. Following ligation, the new product generated (the "ligation product") can optionally be amplified by an enzymatic or chemical reaction. In the preferred embodiment, the chemical ligation reaction joins two probes that have PCR primer sites on them, e.g. universal PCR primers. Additionally, in one embodiment of the invention, one or both ligation probes contain a stuffer sequence, or variable spacer sequence, which is designed to have differing lengths for each probe set (i.e. each target sequence) thereby resulting in a ligation product having a target-specific length. Following ligation a defined length oligonucleotide can now be exponentially amplified by PCR. In accordance with one aspect of the invention, the probes can possess detectable labels (e.g. fluorescent labels, electrochemical labels, magnetic beads, nanoparticles, biotin, etc.) to aid in the identification, purification, quantification or detection of the ligated oligonucleotide product. The probes may also optionally include in their structure: anchoring oligonucleotide sequences designed for subsequent capture on a solid support (microarrays, microbeads, nanoparticles), molecule handles that promote the concentration or manipulation of the ligated product (magnetic particles, oligonucleotide coding sequences), and promoter sequences to facilitate subsequent secondary amplification of the ligated product via an enzyme like a DNA or RNA polymerase.

The ligation reactions of the invention proceed rapidly, are specific for the target(s) of interest, and can produce multiple copies of the ligated product for each target(s), resulting in an amplification (sometimes referred to herein as "product turnover") of the detectable signal. The ligation reactions of the invention do not require the presence of exogeneously added ligases, nor additional enzymes, although some secondary reactions may rely on the use of enzymes such as polymerases, as described below. Ligation chemistries can be chosen from many of the previously described chemical moieties. Preferred chemistries are ones that can be easily incorporated into routine manufacture techniques, are stable during storage, and demonstrate a large preference for target specific ligation when incorporated into a properly designed ligation probe set. Additionally, for embodiments which involve subsequent amplification by an enzyme, ligation chemistries and probe designs (including unnatural nucleotide analogs) that result in a ligation product that can be efficiently processed by an enzyme are preferred. Amplification of the target may also include turnover of the ligation product, either by destabilization, e.g. in which the ligation product has a lower or comparable affinity for the template or target nucleic acid than do the separate ligation probes, or by standard thermocycling in the presence of excess probes. Thus, upon ligation of the hybridized probes, the ligation product is released from the target, freeing the target to serve as a template for a new ligation reaction.

In further aspects of the invention and as is discussed in further detail below, specificity of the assays of the invention are optionally improved through the use of target capture probes. Target capture probes of the invention include a domain complementary to a domain on the target nucleic acid and a capture moiety. The target capture probes do not participate in the ligation reaction with the ligation probes, but are instead designed to hybridize to the target nucleic acid upstream or downstream from the ligation probes. Hybridization of the target capture probe to the target nucleic acid produces a target complex that includes the target nucleic acid, the target capture probe, and any ligation products formed on the target nucleic acid. The target complex can then be bound to a surface or substrate (such as a bead), and any unbound reactants can be separated from the target complexes bound to the surface or substrate. Thus, since any subsequent amplification and/or detection steps are performed on the subset of the original sample of target nucleic acids that were successfully hybridized with ligation probes, the specificity of the subsequent assays is improved.

The above and further aspects and embodiments of the invention are described in further detail in the following sections.

II. Samples

In one aspect, the present invention provides compositions and methods for detecting the presence or absence of target nucleic acids (also referred to herein as "target sequences") in samples. As will be appreciated by those in the art, the samples may comprise any number of things, including, but not limited to, bodily fluids (including, but not limited to, blood, urine, serum, lymph, saliva, anal and vaginal secretions, perspiration and semen, of virtually any organism, with mammalian samples being preferred and human samples being particularly preferred); environmental samples (including, but not limited to, air, agricultural, water and soil samples); plant materials; biological warfare agent samples; research samples (for example, the sample may be the product of an amplification reaction, for example general amplification of genomic DNA); purified samples, such as purified genomic DNA, RNA, proteins, etc.; raw samples (bacteria, virus, genomic DNA, etc.); as will be appreciated by those in the art, virtually any experimental manipulation may have been done on the sample. Some embodiments utilize siRNA and microRNA as target sequences (Zhang et al., *J Cell Physiol.* (2007) 210(2):279-89; Osada et al., *Carcinogenesis.* (2007) 28(1):2-12; and Mattes et al., *Am J Respir Cell Mol. Biol.* (2007) 36(1):8-12, each of which is incorporated herein by reference in its entirety for all purposes, and in particular all teachings related to target sequences).

Some embodiments of the invention utilize samples from stored (e.g. frozen and/or archived) or fresh tissues. Paraffin-embedded samples are of particular use in many embodiments, as these samples can be very useful for diagnosis and prognosis, due to the presence of additional data associated with the samples. Fixed and paraffin-embedded tissue samples as described herein refers to storable or archival tissue samples. Most patient-derived pathological samples are routinely fixed and paraffin-embedded to allow for histological analysis and subsequent archival storage. Such samples are often not useful for traditional methods of nucleic acid detection, because such studies require a high integrity of the nucleic acid sample so that an accurate measure of nucleic acid expression can be made. Often, gene expression studies in paraffin-embedded samples are limited to qualitative monitoring by using immunohistochemical staining to monitor protein expression levels.

A number of techniques exist for the purification of nucleic acids from fixed paraffin-embedded samples as described in WO 2007/133703 the entire contents of which is herein incorporated by reference for all purposes and in particular for all teachings related to the purification of nucleic acids from paraffin-embedded samples. Methods described by Foss, et al *Diagnostic Molecular Pathology*, (1994) 3:148-155 and Paska, C., et al *Diagnostic Molecular Pathology*, (2004) 13:234-240 as well as commercially available kits like Ambion's Recoverall Total Nucleic acid Isolation kit are included by reference in their entirety. Common methods start with a step that removes the paraffin from the tissue via extraction with Xylene or other organic solvent, followed by treatment with heat and a protease like proteinase K which cleaves the tissue and proteins and helps to release the genomic material from the tissue. The released nucleic acids are then captured on a membrane or precipitated from solution, washed to removed impurities and for the case of mRNA isolation, a DNase treatment step is sometimes added to degrade unwanted DNA.

As will be discussed in further detail herein, both the target analytes and the ligation probes used to detect the target analytes may in accordance with the invention comprise nucleic acids. By "nucleic acid" or "oligonucleotide" or grammatical equivalents herein means at least two nucleotides covalently linked together. The target nucleic acids may comprise DNA or RNA. A nucleic acid of the present invention will generally contain phosphodiester bonds (for example in the case of the target sequences), although in some cases, as outlined below, nucleic acid analogs are included that may have alternate backbones (particularly for use with the ligation, label or capture probes), comprising, for example, phosphoramide (Beaucage et al., *Tetrahedron* (1993) 49(10):1925 and references therein; Letsinger, *J. Org. Chem.* (1970) 35:3800; Sprinzl et al., *Eur. J. Biochem.* (1977) 81:579; Letsinger et al., *Nucl. Acids Res.* (1986) 14:3487; Sawai et al, *Chem. Lett.* (1984) 805; Letsinger et al., *J. Am. Chem. Soc.* (1988) 110:4470; and Pauwels et al., *Chemica Scripta* (1986) 26:141), phosphorothioate (Mag et al., *Nucleic Acids Res.* (1991) 19:1437; and U.S. Pat. No. 5,644,048), phosphorodithioate (Briu et al., *J. Am. Chem. Soc.* (1989) 111:2321, 0-methylphophoroamidite linkages (see Eckstein, *Oligonucleotides and Analogues: A Practical Approach*, Oxford University Press), and peptide nucleic acid backbones and linkages (see Egholm, *J. Am. Chem. Soc.* (1992) 114:1895; Meier et al., *Chem. Int. Ed. Engl.* (1992) 31:1008; Nielsen, *Nature*, (1993) 365:566; Carlsson et al., *Nature* (1996) 380:207, all of which are incorporated herein by reference in their entirety). Other analog nucleic acids include those with bicyclic structures including locked nucleic acids, Koshkin et al., *J. Am. Chem. Soc.* (1998) 120:13252 3); positive backbones (Denpcy et al., *Proc. Natl. Acad. Sci. USA* (1995) 92:6097; non-ionic backbones (U.S. Pat. Nos. 5,386,023, 5,637,684, 5,602,240, 5,216,141 and 4,469,863; Kiedrowshi et al., *Angew. Chem. Intl. Ed. English* (1991) 30:423; Letsinger et al., *J. Am. Chem. Soc.* (1988) 110:4470; Letsinger et al., *Nucleoside & Nucleotide* (1994) 13:1597; Chapters 2 and 3, *ASC Symposium Series* 580, Ed. Y. S. Sanghui and P. Dan Cook; Mesmaeker et al., *Bioorganic & Medicinal Chem. Lett.* (1994) 4:395; Jeffs et al., *J. Biomolecular NMR* (1994) 34:17; Xu et al., *Tetrahedron Lett.* (1996) 37:743) and non-ribose backbones, including those described in U.S. Pat. Nos. 5,235,033 and 5,034,506, and Chapters 6 and 7, *ASC Symposium Series* 580, Ed. Y. S. Sanghui and P. Dan Cook. Nucleic acids containing one or more carbocyclic sugars are also included within the definition of nucleic acids (see Jenkins et al., *Chem. Soc. Rev.* (1995) pp 169-176). Several nucleic acid analogs are described in Rawls, *C & E News* Jun. 2, 1997 page 35. All of these references are herein expressly incorporated by reference in their entirety for all purposes, and in particular for all teachings related to nucleic acids. These modifications of the ribose-phosphate backbone may be done to facilitate the addition of labels or other moieties, to increase or decrease the stability and half-life of such molecules in physiological environments, etc.

For example, the use of the ligation moieties of the invention can, in some cases depending on the chemistry utilized, result in nucleic acid analogs as the ligation product. For example, as shown in Scheme 1, below, the use of certain ligation moieties result in a phosphothioester bonds.

As will be appreciated by those in the art, all of these nucleic acid analogs may find use in the present invention. In addition, mixtures of naturally occurring nucleic acids and analogs can be made; for example, at the site of a ligation moiety, an analog structure may be used. Alternatively, mixtures of different nucleic acid analogs, and mixtures of naturally occurring nucleic acids and analogs may be made.

Nucleic acid analogue may include, for example, peptide nucleic acid (PNA, WO 92/20702, incorporated herein by reference in its entirety) and Locked Nucleic Acid (LNA, Koshkin A A et al. *Tetrahedron* (1998) 54:3607-3630, Koshkin A A et al. *J. Am. Chem. Soc.* (1998) 120:13252-13253, Wahlestedt C et al. *PNAS* (2000) 97:5633-5638, each of which is incorporated herein by reference in its entirety). In some applications analogue backbones of this type may exhibit improved hybridization kinetics, improved thermal stability and improved sensitivity to mismatch sequences.

The nucleic acids may be single stranded or double stranded, as specified, or contain portions of both double stranded or single stranded sequences. The nucleic acid may be DNA, both genomic and cDNA, RNA or a hybrid, where the nucleic acid contains any combination of deoxyribo- and ribo-nucleotides, and any combination of bases, including naturally occurring nucleobases (uracil, adenine, thymine, cytosine, guanine) and non-naturally occurring nucleobases (inosine, xathanine hypoxathanine, isocytosine, isoguanine, 5-methylcytosine, pseudoisocytosine, 2-thiouracil and 2-thiothymine, 2-aminopurine, N9-(2-amino-6-chloropurine), N9-(2,6-diaminopurine), hypoxanthine, N9-(7-deazaguanine), N9-(7-deaza-8-aza-guanine) and N8-(7-deaza-8-aza-adenine). 5-propynyl-uracil, 2-thio-5-propynyl-uracil) etc. As used herein, the term "nucleobase" includes both "nucleosides" and "nucleotides", and monomers of nucleic acid analogs. Thus, for example, the individual units of a peptide nucleic acid, each containing a base, are referred to herein as a nucleobase.

Nucleic acid samples (e.g. target sequences) that do not exist in a single-stranded state in the region of the target sequence(s) are generally rendered single-stranded in such region(s) prior to detection or hybridization. Generally, nucleic acid samples can be rendered single-stranded in the region of the target sequence using heat or chemical denaturation. For polynucleotides obtained via amplification, methods suitable for generating single-stranded amplification products are preferred. Non-limiting examples of amplification processes suitable for generating single-stranded amplification product polynucleotides include, but are not limited to, T7 RNA polymerase run-off transcription, RCA, Asymmetric PCR (Bachmann et al., *Nucleic Acid Res.* (1990) 18:1309), and Asynchronous PCR (WO 01/94638). Commonly known methods for rendering regions of double-stranded polynucleotides single stranded, such as the use of PNA openers (U.S. Pat. No. 6,265,166), may also be used to generate single-stranded target sequences on a polynucleotide.

Target Nucleic Acids

As discussed further herein, the invention provides methods and compositions for detecting target sequences. By "target sequence" or "target nucleic acid" or grammatical equivalents herein means a nucleic acid sequence on a single strand of nucleic acid. The target sequence may be a portion of a gene, a regulatory sequence, genomic DNA, cDNA, RNA including mRNA, MicroRNA and rRNA, or others. As is outlined herein, the target sequence may be a target sequence from a sample, or a secondary target such as a product of an amplification reaction, etc. It may be any length, with the understanding that longer sequences are more specific. As will be appreciated by those in the art, the complementary target sequence may take many forms. For example, it may be contained within a larger nucleic acid sequence, i.e. all or part of a gene or mRNA, a restriction fragment of a plasmid or genomic DNA, among others. Any and all combinations of these may serve as target nucleic acids in a particular assay. In many cases, multiplex assays are done, where a plurality of target sequences are simultaneously detected, such as for gene expression profiling as is more fully described below.

In general, each target sequence is comprised of a plurality of different target domains. Each target sequence has at least a pair of ligation domains for hybridization to a set of ligation probes, or more, as described below. For example, a first target domain of a sample target sequence may hybridize to a first ligation probe, and a second target domain in the target sequence may hybridize to a second ligation probe, such as to bring the chemical ligation moieties into spatial proximity sufficient to allow spontaneous chemical ligation.

In general, each pair of target ligation domains is adjacent to each other, that is, there are no nucleotides separating the two domains. This finds use in both general detection of target sequences (e.g. gene expression profiling using mRNA as the target sequences), transfer reactions as discussed below, as well as for single nucleotide polymorphism (SNP) detection. For SNP detection, the target sequence comprises a position for which sequence information is desired, generally referred to herein as the "detection position". In some embodiments, the detection position is a single nucleotide, although in some embodiments, it may comprise a plurality of nucleotides, either contiguous with each other or separated by one or more nucleotides. By "plurality" as used herein is meant at least two. As used herein, the base of a ligation probe which basepairs with the detection position base in a hybrid is termed the "interrogation position".

Each sample target nucleic acid can additionally have multiple pairs of ligation domains. That is, 1, 2, 3 or more sets of ligation probes can hybridize to the same target sequence at multiple locations, as is generally depicted in FIG. 11 or 12. As is more fully outlined below, the use of multiple ligation domains per target nucleic acid can serve as the basis to assess the integrity of the target nucleic acids (and/or the original sample) in the sample.

The sample target nucleic acids may contain other domains, in addition to ligation domains. In certain embodiments, the target nucleic acids of the invention include a target capture domain to which a target capture domain is able to hybridize. In general, as depicted in FIG. 11 and depending on the purpose of the assay, a target capture domain can be "upstream", "downstream" or "in-between" one or more of the ligation domains of the target nucleic acid.

Unless specified, the terms "first" and "second" are not meant to confer an orientation of the sequences with respect to the 5'-3' orientation of the target sequence. For example, assuming a 5'-3' orientation of the complementary target sequence, the first target domain may be located either 5' to the second domain, or 3' to the second domain. For ease of reference and not to be limiting, these domains are sometimes referred to as "upstream" and "downstream", with the normal convention being the target sequence being displayed in a 5' to 3' orientation. However, it should be noted that ligation domains have an orientation such that the 3' and 5' ligation moieties of the ligation probe sets hybridize either completely adjacently (e.g. no intervening nucleobases) or within a distance that the linkers attaching the ligation moieties allow for ligation.

In some embodiments, the pair of target ligation domains may be separated. For example, in some cases, when ligation amplification is desired, the ligation probes may utilize linkers and be separated when hybridized by one or more nucleobases of the target sequence to confer hybridization instability on the ligated product. In other applications, As will be discussed in further detail below, buffers of the invention are of use in stabilizing nucleic acids, particularly RNA, in a sample. In some aspects of the invention, samples are collected into buffers of the invention. In further embodiments, and as is discussed in further detail below, such buffers include one or more of a denaturant, a reducing agent, a surfactant, a pH buffer, EDTA, and any combination thereof.

III. Buffers

In one aspect, the invention provides methods and compositions which stabilize nucleic acids (also referred to herein as "sample nucleic acid" or "target nucleic acids"). By "stabilize" as used herein is meant that the nucleic acids in a sample are resistant to degradation even when stored at ambient room temperature or above for a period of time. In some embodiments, nucleic acids contained in buffers of the invention are stable at room temperature or above for about one day to about three months. Stability can be measured using any means known in the art, including assays for nucleic acid integrity as further discussed below. In further embodiments, a sample comprising nucleic acids contained in a buffer of the invention is assessed as having increased stability as compared to a sample that was not stored in the buffer if at least 10%, 20%, 30%, 40%, 50%, 60%, 70%, 80%, 90%, 95% of the nucleic acids in the sample stored in the buffer show less degradation than those in the sample that was not stored in the buffer. In yet further embodiments, a sample is identified as being stabilized by the buffers of the present invention if at least a majority of the nucleic acids in the sample show reduced degradation as compared to a sample that was not stored in the buffer. Stability of RNA samples are often assessed by Capillary Electrophoresis methodologies that look to measure the average size of the nucleic acid sample. Stabilized samples will have a longer average size than non-stabilized samples. Another aspect of this invention is the use of multiple ligation probe sets combined with one or more target capture probes that can be used to assess the average size of a target nucleic acid, and by correlation, the level of degradation of the target nucleic acid.

Buffers of the invention can optionally and in any combination include one or more of a denaturant, a reducing agent, a surfactant, a pH buffer, a chelator such as EDTA, and any combination thereof. As will be appreciated, buffers of the invention may include multiple types of components within the same class—e.g., buffers of the invention may include one or more different kinds of denaturants in combination with one or more types of surfactants, and so on.

An advantage of the buffers of the present invention is that they can be used to stabilize nucleic acids such as RNA in a sample and then the sample can be directly analyzed from the buffer solutions in accordance with the methods described herein. In other words, samples contained in buffer solutions of the invention can be subjected to the chemical ligation and detection methods described herein without isolation or purification of the RNA. Another advantage of the buffers of the invention is that cell lysis occurs upon the collection of the sample in the buffer, thus not requiring an additional lysis step to release the target nucleic acids from the sample.

In an exemplary embodiment, a sample comprising RNA can be combined in a buffer solution comprising guanidinium hydrochloride, ethylenediaminetetraacetic acid (EDTA), dithiothreitol (DTT), Triton X-100, and Tris-HCL at a pH of 7.5. In another embodiment, the sample comprising RNA can be combined in a buffer solution comprising guanidinium isothiocyanate, EDTA, DTT, Triton X-100, and Tris-HCl at a pH of 7.5. The RNA is stable in such buffer solutions and it is not necessary to isolate the RNA from other sample constituents which may enhance degradation of the RNA.

In further embodiments, the buffers of the invention preferably include a denaturant, particularly a chaotropic cation, that has the effect of increasing reaction and binding efficiency in the methods and assays described herein by helping to unfold the secondary structure of the RNA. Common Chaotropic molecules are guanidinium hydrochloride, guanidinium isothiocyanate, betaine or glycine betaine, urea, thiourea, and lithium perchlorate. Without being bound by theory, chaotropic agents that are effective in breaking of tertiary structure in nucleic acids are preferred and chaotropic agents that also maintain the solubility of the nucleic acid target in solution are particularly beneficial. An advantage of buffers of the invention, particularly buffers comprising a chaotropic cation, is that the buffer keeps the nucleic acids of the sample in solution. This is in contrast to other traditional buffers used in transport systems for blood-based tests, which tend to precipitate/form a cationic shell around the nucleic acids of the sample (particularly RNA). Since the buffers of the invention keep the nucleic acids in solution, and since the chemical ligation methods of the assays of the invention do not require enzymes, a sample can be collected into a buffer and the ligation probes (and in many embodiments, target capture probes) can be added to the sample and ligation products formed. To change hybridization conditions to then release the ligation products or target complexes for further analysis, the sample plus buffer can simply be diluted to dilute the denaturant and thereby change the hybridization conditions, thus allowing analysis of the nucleic acids using any of the methods described herein and known in the art.

In further embodiments, the buffers of the invention have a pH of about 5 to about 8.5. More preferably the buffer solution has a pH of about 6 to 8 and even more preferably, a pH of approximately 7.3 or 7.5.

The following sections discuss exemplary buffer components in further detail. Although each of these components is discussed separately, the present invention encompasses any combination of the following buffer components as well as any other components known in the art.

Denaturants

In preferred embodiments, buffers of the present invention include one or more denaturants. By denaturant as used herein is meant any substance that serves to unfold the double helix of nucleic acids with loss of secondary and tertiary structure. In further embodiments, the denaturants comprise a chaotropic cation, including without limitation guanidinium hydrochloride (GuHCl) and guanidinium isothiocyanate.

In further embodiments, the denaturant is guanidinium hydrochloride, which is present in a concentration from about 1 molar to about 8 molar and more preferably, a concentration of about 2 molar to about 4 molar, and even more preferably, a concentration of approximately 3 molar. In further embodiments, concentration of GuHCl in buffers of the invention range from about 0.2-10, 0.5-9, 1-8, 1.5-7, 2-6, 2.5-5, and 3.0-4.0 molar. In still further embodiments, concentrations of GuHCl in buffers of the invention are about 0.5, 1, 2, 3, 4, 5, 6, 7, 8, 9, 10, 11, 12, 13, 14 or 15 molar.

In other embodiments, the denaturant is guanidinium isothiocyanate, which is present in a concentration from about 1 molar to about 8 molar and more preferably, a concentration of about 2 molar to about 4 molar, and even more preferably, a concentration of approximately 3 molar. In further embodiments, concentration of guanidinium isothiocyanate in buffers of the invention range from about 0.2-10, 0.5-9, 1-8, 1.5-7, 2-6, 2.5-5, and 3.0-4.0 molar. In still further embodiments, concentrations of guanidinium isothiocyanate in buffers of the invention are about 0.5, 1, 2, 3, 4, 5, 6, 7, 8, 9, 10, 11, 12, 13, 14 or 15 molar.

As will be appreciated, other denaturants known in the art can be used in buffers of the invention at similar concentrations as those listed above for guanidinium hydrochloride and guanidinium isothiocyanate.

In some embodiments, such as with the use of high concentrations of salts such as guanidinium salts, these reagents also serve as lysis agents. As will be appreciated by those in the art, in general, the use of a denaturant that also serves as a cell lysis agent is of particular use, although the present invention also contemplates the use of a first separate lysis step followed by the addition of the denaturant.

Surfactants

In some embodiments, buffers of the present invention include one or more surfactants. In further embodiments, the surfactant includes without limitation Triton X-100 and sodium N-lauroylsarcosine.

In further embodiments, the surfactant is present in buffers of the invention at a concentration from about 0.1% to about 5% by weight. In still further embodiments, the surfactant is present in a concentration of about 0.1%-10%, 0.5%-9.5%, 1%-9%, 1.5%-8.5%, 2%-8%, 2.5%-7.5%, 3%-7%, 3.5%-6.5%, 4%-6%, and 4.5%-5.5% by weight. In preferred embodiments, the surfactant has a concentration of about 0.5% to about 3%. In a further embodiment, the surfactant has a concentration of approximately 1.5% by weight.

ph Buffer

In some embodiments, buffers of the present invention include one or more pH buffers. Such pH buffers include without limitation Tris. In other embodiments the pH buffer can be one of many known by those skilled in the art. Generally the pH buffer used in the present invention includes an agent that has a pKa within one pH unit of the operating pH.

In some embodiments, the pH buffer is present in buffers of the invention at a concentration from about 10 mM to about 100 mM. In preferred embodiments, the pH buffer has a concentration of about 20 mM to about 50 mM and more preferably, a concentration of approximately 30 mM. In further embodiments, the pH buffer has a concentration of about 5-150, 10-140, 15-130, 20-120, 25-110, 30-100, 35-90, 40-80, 45-70, and 50-60 mM.

Reducing Agents

In some embodiments, buffers of the present invention include one or more reducing agents. Such reducing agents can include without limitation Dithiothreitol (DTT) and mercaptoethanol.

In further embodiments, the reducing agents have a concentration from about 1 mM to about 100 mM. In preferred embodiments, the reducing agent has a concentration of about 4 mM to about 7 mM and even more preferably, a concentration of approximately 5 mM. In still further embodiments, the reducing agents have a concentration of about 0.5-10, 1-9.5, 1.5-9, 2-8.5, 2.5-8, 3-7.5, 3.5-7, 4-6.5 mM. In yet further embodiments, the reducing agents have a concentration of about 1-150, 10-140, 15-130, 20-120, 25-110, 30-100, 35-90, 40-80, 45-70, and 50-60 mM.

EDTA

In further embodiments, buffers of the invention include EDTA at a concentration of from about 1 mM to about 100 mM. More preferably the EDTA has a concentration of about 10 mM to about 50 mM and even more preferably, a concentration of approximately 20 mM. In further embodiments, the EDTA is present at a concentration of about 1-150, 10-140, 15-130, 20-120, 25-110, 30-100, 35-90, 40-80, 45-70, and 50-60 mM. In still further embodiments, the EDTA has a concentration of about 5, 10, 15, 20, 25, 30, 35, 40, 45, 50, 55, 60 mM.

Additional Buffer Components

The buffers of the invention may further include any additional components known in the art, particularly components known in the art to be of use in reactions involving nucleic acids. Additional components may include without limitation: adjuvants, diluents, binders, stabilizers, salts (including NaCl and $MgCl_2$), lipophilic solvents, preservatives, or the like. Buffer components may also include pharmaceutical excipients and additives, proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this invention, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

Uses of Buffers of the Invention

Buffers of the invention can be used with any of the sample collection, chemical ligation, or assays discussed herein.

In some embodiments, samples containing target nucleic acids are collected into buffers of the invention. The advantage of buffers of the invention is that they tend to stabilize nucleic acids contained in the samples. Thus, degradation that often begins to occur, particularly with RNA, immediately upon collection is prevented to at least some degree by the buffers of the invention, providing the advantage of a robust set of target nucleic acids for further analysis using methods of the invention.

In further embodiments, upon collection of samples into buffers of the invention, ligation probes and optionally target capture probes (which are further discussed in detail below) can be added directly to the sample in the buffer without purification of the target nucleic acids. In some embodiments, the sample in the buffer is first diluted prior to the addition of the probes (including ligation and target capture probes). Because the ligation methods of the present invention are not reliant on enzymes, hybridization and ligation of ligation probes can occur without purifying the nucleic acids from the sample and without relying on the use of a ligase enzyme. This further serves to limit the degradation that occurs in the nucleic acids of the sample.

IV. Ligation Probes and Chemical Ligation Methods

In one aspect, ligation probes of the invention comprise any polymeric species that is capable of interacting with a nucleic acid target(s) in a sequence specific manner and possess chemical moieties allowing the probes to undergo a spontaneous chemical ligation reaction with another polymeric species possessing complementary chemical moieties. In one embodiment, the ligation probes can be DNA, RNA, PNA, LNA, modified versions of the aforementioned and/or any hybrids of the same (e.g. DNA/RNA hybrids, DNA/LNA hybrids, DNA/PNA hybrids). In a preferred embodiment, the ligation probes comprise DNA or RNA oligonucleotides.

Ligation probes of the invention are designed such that when the probes bind to a part of the target polynucleotide in close spatial proximity, a chemical ligation reaction occurs between the probes. In general, the probes comprise chemically reactive moieties (herein generally referred to as "ligation moieties") and bind to the target polynucleotide in a particular orientation, such that the chemically reactive moieties come into close spatial proximity, thus resulting in a spontaneous ligation reaction that can take place without the use of a ligase enzyme.

In one embodiment, the invention provides sets of ligation probes, usually a first and a second ligation probe, although as is described herein some embodiments utilize more than two. In addition, as noted herein, in some cases a transfer reaction is done rather than ligation; "ligation probes" includes "transfer probes". Each ligation probe comprises a nucleic acid portion, sometimes referred to herein as a "ligation domain" or "probe domain" that is substantially complementary to one of the target domains. Probes of the present invention are designed to be complementary to a target sequence such that hybridization of the target sequence and the probes of the present invention occurs. As outlined herein, this complementarity need not be perfect; there may be any number of base pair mismatches which will interfere with hybridization between the target sequence and the probes of the present invention. However, if the number of mutations is so great that no hybridization can occur under even the least stringent of hybridization conditions, the sequence is not a complementary sequence. Thus, by "substantially complementary" herein is meant that the probes are sufficiently complementary to the target sequences to hybridize under normal reaction conditions. "Identical" sequences are those that over the length of the shorter sequence of nucleobases, perfect complementarity exists. A variety of hybridization conditions may be used in the present invention, including high, moderate and low stringency conditions; see for example Maniatis et al., *Molecular Cloning: A Laboratory Manual,* 2d Edition, 1989, and Ausubel, et al, *Short Protocols in Molecular Biology,* herein incorporated by reference. The hybridization conditions may also vary when a non-ionic backbone, e.g. PNA is used, as is known in the art.

In one aspect of the invention, the length of the probe is designed to vary with the length of the target sequence, the specificity required, the reaction (e.g. ligation or transfer)

and the hybridization and wash conditions. Generally, in this aspect ligation probes range from about 5 to about 150 nucleobases, with from about 15 to about 100 being preferred and from about 25 to about 75 being especially preferred. In general, these lengths apply equally to ligation and transfer probes.

In another embodiment of the invention, referred to herein as "CLPA-CE" which is described more fully below, probe length is designed to vary for each target of interest thereby generating ligation products that can be identified and analyzed based on length variance.

Ligation probes of the invention are designed to be specific for the polynucleotide target. These probes bind to the target in close spatial proximity to each other and are oriented in such a manner that the chemically reactive ligation moieties are in close spatial proximity. In one aspect, two or more probes are designed to bind near adjacent sites on a target polynucleotide. In a preferred embodiment, two probes bind to the target such that the ligation moiety at the 5' end of one oligonucleotide probe is able to interact with the ligation moiety at the 3' end of the other probe. In preferred embodiments, the ligation reaction between the ligation moieties occurs without the use of an exogenous ligase enzyme, also referred to herein as "chemical ligation." It should be noted that the sets of ligation probes do not ligate using ligases due to the presence of the ligation moieties.

In the case of SNP detection, a set of ligation probes may in some cases actually comprise be three or four or five different ligation probes, some of which are allele specific. By "allele specific" probe or primer is meant a probe or primer that hybridizes to a target sequence and discriminates between alleles. In this case, for example, when a SNP is biallelic (such as depicted in FIG. 13), a set of three ligation probes are used, two of which contain a different nucleotide at the detection position. That is, as is known in the art, mismatches at the junction of a ligation complex will either result in no ligation or a decreased amount of ligation. So, depending on the orientation of the probes, the detection position can either be on the terminal position of the "upstream" probe or the downstream probe as is depicted in FIGS. 13A and 13C). The mismatch can also be positioned internally to a probe and the mismatch discrimination is based on differences in the binding strength or Tm of the mismatch discriminating probes (as depicted in FIG. 13B. In the case of a biallelic SNP, two of the probes have the same probe domain except that the nucleotide at the detection position, corresponding to the interrogation position on the target sequence, is different. Thus, depending on whether the patient is homozygotic (T/T or C/C) or heterozygotic (T/C or C/T), the ligation between probes occurs. Furthermore, in this invention, there is generally an additional difference between the mismatch detection ligation probes that enables the easy identification of which probe was preferentially ligated. For example, the "A" allelic probe may have a variable spacer sequence of 15 nucleotides (15 mer) and the "G" allelic probe may have a variable spacer sequence of 20 nucleotides (20 mer), the probes may have different capture domains or label sequences, etc.

Similarly, as will be appreciated by those in the art, triallelic or quadallelic SNPs use 4 (3 probes with the same target domain and one with the other target domain) or 5 (4 probes with the same target domain and one with the other target domain) ligation probes in the set.

The size of the primer and probe nucleic acid may vary, as will be appreciated by those in the art with each portion of the probe and the total length of the probe in general varying from 5 to 500 nucleotides in length. Each portion is preferably between 10 and 100 being preferred, between 15 and 50 being particularly preferred, and from 10 to 35 being especially preferred, depending on the use and amplification technique. Thus, for example, the universal priming site(s) of the probes are each preferably about 15-20 nucleotides in length, with 18 being especially preferred. The adapter sequences of the probes are preferably from 15-25 nucleotides in length, with 20 being especially preferred. The target specific portion of the probe is preferably from 15-50 nucleotides in length. In addition, the primer may include an additional amplification priming site. In a preferred embodiment the additional amplification priming site is a T7 RNA polymerase priming site.

A number of non-enzymatic or template mediated chemical ligation methods can be used in accordance with the present invention. These include chemical ligation methods that utilize coupling reagents, such as N-cyanoimidazole, cyanogen bromide, and 1-ethyl-3-(3-dimethylaminopropyl)-carbodiimide hydrochloride. See Metelev, V. G., et al., *Nucleosides & Nucleotides* (1999) 18:2711; Luebke, K. J., and Dervan, P. B. *J. Am. Chem. Soc.* (1989) 111:8733; and Shabarova, Z. A., et al., *Nucleic Acids Research* (1991) 19:4247, each of which is incorporated herein by reference in its entirety for all purposes and in particular for all teachings related to chemical ligation. Kool (U.S. Pat. No. 7,033,753), which is incorporated herein by reference in its entirety, describes the use of chemical ligation and fluorescence resonance energy transfer (FRET) to detect genetic polymorphisms. The readout in this process is based on the solution phase change in fluorescent intensity. Terbrueggen (US Patent Publication No. 12008/0124810) which is incorporated herein by reference in its entirety describes the use of chemical ligation methods, compositions and reagents for the detection of nucleic acids via microarray detection. Other chemical ligation methods react a 5'-tosylate or 5'-iodo group with a 3'-phosphorothioate group, resulting in a DNA structure with a sulfur atom replacing one of the bridging phosphodiester oxygen atoms. See Gryanov, S. M., and Letsinger, R. L., *Nucleic Acids Research* (1993) 21:1403; Xu, Y. and Kool, E. T. *Tetrahedron Letters* (1997) 38:5595; and Xu, Y. and Kool, E. T., *Nucleic Acids Research* (1999) 27:875, each of which is herein incorporated by reference in its entirety. Letsinger et al (U.S. Pat. No. 5,780,613, herein incorporated by reference in its entirety) have previously described an irreversible, nonenzymatic, covalent autoligation of adjacent, template-bound oligonucleotides wherein one oligonucleotide has a 5' displaceable group and the other oligonucleotide has a 3' thiophosphoryl group. Each of these references describing chemical ligation methods is incorporated herein by reference in its entirety for all purposes and in particular for all teachings related to chemical ligation.

In one aspect, the ligation reactions of the invention include transfer reactions. In this embodiment, the probes hybridize to the target sequence, but rather than oligonucleotide probes being ligated together to form a ligation product, a nucleic acid-directed transfer of a molecular entity (including reporter molecules such as fluorophores, quenchers, etc) from one oligonucleotide probe to other occurs. This transfer reaction is analogous to a ligation reaction, however instead of joining of two or more probes, one of the probes is ligated to the transfer molecule and the other probe is the "leaving" of the chemical reaction. Importantly, similar to the ligation reaction, the transfer reaction is facilitated by the proximal binding of the transfer probes onto a nucleic acid target, such that significant signal is detected only if the probes have hybridized to the target nucleic acid in close enough proximity to one another (e.g., at adjacent sites) for the transfer reaction to take place.

In one aspect, the invention relates to methods of chemical ligation that include the binding of at least a first and a second ligation probe to the target nucleic acid to form a "ligation substrate" under conditions such that the ligation moieties of the first and second ligation probes are able to spontaneously react, ligating the probes together, in the absence of exogenous ligase; that is, no exogenous ligase is added to the reaction and instead the reaction proceeds without the use of a ligase. In the case of the transfer reaction, this may be referred to as either a "ligation substrate" or a "transfer substrate". By "ligation substrate" herein is meant a substrate for chemical ligation comprising at least one target nucleic acid sequence and two or more ligation probes. Similarly, included within the definition of "ligation substrate" is a "transfer substrate", comprising at least one target nucleic acid sequence and two or more transfer probes. Once the chemical ligation step has occurred, the product of reaction is sometimes referred to as a "ligation complex", comprising the ligated probes and the target to which they are still hybridized.

Figure 3:
FIG. 3 is a schematic representation showing one embodiment of the 2-probe and the 3-probe CLPA reaction.
Figure 3:

In some embodiments of the invention, for example when additional specificity is desired, more than two ligation probes can be used, as is generally depicted in FIG. 3. In this embodiment, the "middle" ligation probe(s) can also be adjacent or separated by one or more nucleobases of the target sequence. In a preferred embodiment, the ligation reaction does not require the presence of a ligase enzyme and occurs spontaneously between the bound probes in the absence of any addition (e.g. exogeneous) ligase.

Chemical ligation can, under appropriate conditions, occur spontaneously without the addition of any additional activating reagents or stimuli. Alternatively, "activating" agents or external stimuli can be used to promote the chemical ligation reaction. Examples of activating agents include, without limitation, carbodiimide, cyanogen bromide (BrCN), imidazole, 1-methylimidazole/carbodiimide/cystamine, N-cyanoimidazole, dithiothreitol (DTT), tris(2-carboxyethyl)phosphine (TCEP) and other reducing agents as well as external stimuli like ultraviolet light, heat and/or pressure changes.

As is outlined herein, the ligation moieties of the invention may take a variety of configurations, depending on a number of factors. Most of the chemistries depicted herein are used in phosphoramidite reactions that generally progress in a 3' to 5' direction. That is, the resin contains chemistry allowing attachment of phosphoramidites at the 5' end of the molecule. However, as is known in the art, phosphoramidites can be used to progress in the 5' to 3' direction; thus, the invention includes moieties with opposite orientation to those outlined herein.

Each set of ligation probes (or transfer probes) contains a set of a first ligation moiety and a second ligation moiety. The identification of these ligation moiety pairs depends on the chemistry of the ligation to be used. In addition, as described herein, linkers (including but not limited to destabilization linkers) may be present between the probe domain and the ligation moiety of one or both ligation probes. In general, for ease of discussion, the description herein may use the terms "upstream" and "downstream" ligation probes, although this is not meant to be limiting.

Different sets of ligation probes can be designed for use in any of the assays and methods described herein. The sets of ligation probes can be designed to include ligation probes directed to one or more target domains of a target nucleic acid, or different probe sets can be designed to detect different target nucleic acids. For example, for detection of a particular target nucleic acid in embodiments in which two ligation probes are used, a set of ligation probes is designed such that the first probe (e.g., the "upstream probe") comprises a probe domain directed to a first target domain. The set also includes a second ligation probe (e.g., the "downstream probe") that is directed to a second target domain that is adjacent to and downstream from the first target domain. The first and second target domains may in some embodiments be separated by a gap of one, two or three nucleotides. This set of ligation probes thus produces ligation products that can be detected to identify the presence of the target nucleic acid to which they are directed. In further embodiments, different sets of ligation probes can be designed to detect different target nucleic acids. In still further embodiments, different sets of ligation probes are designed to detect the same target nucleic acid—in such embodiments, the different sets of ligation probes are directed to different domains of the same target nucleic acid, such that the same target nucleic acid may have multiple ligation products, depending on the number of different probe sets used. As will be appreciated, similar designs can be used when designing sets of probes for use in embodiments in which more than two ligation probes are used to form a single ligation product.

Halo Leaving Group Chemistry

In one embodiment of the invention, the chemistry is based on 5' halogen leaving group technology such as is generally described in Gryanov, S. M., and Letsinger, R. L., (1993) *Nucleic Acids Research,* 21:1403; Xu, Y. and Kool, E. T. (1997) *Tetrahedron Letters,* 38:5595; Xu, Y. and Kool, E. T., (1999) *Nucleic Acids Research,* 27:875; Arar et al., (1995), *BioConj. Chem.,* 6:573; Kool, E. T. et. al, (2001) *Nature Biotechnol* 19:148; Kool, E. T. et. al., (1995) *Nucleic Acids Res,* 23 (17):3547; Letsinger et al., U.S. Pat. No. 5,476,930; Shouten et al., U.S. Pat. No. 6,955,901; Andersen et al., U.S. Pat. No. 7,153,658, all of which are expressly incorporated by reference herein. In this embodiment, the first ligation probe includes at its 5' end a nucleoside having a 5' leaving group, and the second ligation probe includes at its 3' end a nucleoside having 3' nucleophilic group such as a 3' thiophosphoryl. The 5' leaving group can include many common leaving groups know to those skilled in the art including, for example the halo-species (I, Br, Cl) and groups such as those described by Abe and Kool, *J. Am. Chem. Soc.* (2004) 126:13980-13986, which is incorporated herein by reference in its entirety. In a more preferred embodiment of this aspect of the invention, the first ligation probe has a 5' leaving group attached through a flexible linker and a downstream oligonucleotide which has a 3' thiophosphoryl group. This configuration leads to a significant increase in the rate of reaction and results in multiple copies of ligated product being produced for every target.

The "upstream" oligonucleotide, defined in relation to the 5' to 3' direction of the polynucleotide template as the oligonucleotide that binds on the "upstream" side (i.e., the left, or 5' side) of the template includes, as its 5' end, a 5'-leaving group. Any leaving group capable of participating in an $S_N2$ reaction involving sulfur, selenium, or tellurium as the nucleophile can be utilized. The leaving group is an atom or group attached to carbon such that on nucleophilic attack of the carbon atom by the nucleophile (sulfur, selenium or tellurium) of the modified phosphoryl group, the leaving group leaves as an anion. Suitable leaving groups include, but are not limited to a halide, such as iodide, bromide or chloride, a tosylate, benzenesulfonate or p-nitrophenylester, as well as RSO$_3$ where R is phenyl or phenyl substituted with one to five atoms or groups comprising F, Cl, Br, I, alkyl (C1 to C6), nitro, cyano, sulfonyl and carbonyl, or R is alkyl with one to six carbons. The leaving group is preferably an iodide, and the nucleoside at the 5' end of the upstream oligonucleotide is, in the case of DNA, a 5'-deoxy-5'-iodo-2'-deoxynucleoside. Examples of suitable 5'-deoxy-5'-iodo-2'-deoxynucleosides include, but are not limited to, 5'-deoxy-5'-iodothymidine (5'-I-T), 5'-deoxy-5'-iodo-2'-deoxycytidine (5'-I-dC), 5'-deoxy-5'-iodo-2'-deoxyadenosine (5'-I-dA), 5'-deoxy-5'-iodo-3-deaza-2'-deoxyadenosine (5'-I-3-deaza-dA), 5'-deoxy-5'-iodo-2'-deoxyguanosine (5'-I-dG) and 5'-deoxy-5'-iodo-3-deaza-2'-deoxyguanosine (5'-I-3-deaza-dG), and the phosphoroamidite derivatives thereof (see FIG. 2). In the case of RNA oligonucleotides, analogous examples of suitable 5'-deoxy-5'-iodonucleosides include, but are not limited to, 5'-deoxy-5'-iodouracil (5'-I-U), 5'-deoxy-5'-iodocytidine (5'-I-C), 5'-deoxy-5'-iodoadenosine (5'-I-A), 5'-deoxy-5'-iodo-3-deazaadenosine (5'-I-3-deaza-A), 5'-deoxy-5'-iodoguanosine (5'-I-G) and 5'-deoxy-5'-iodo-3-deazaguanosine (5'-I-3-deaza-G), and the phosphoroamidite derivatives thereof. In a preferred embodiment, an upstream ligation probe contains 2'-deoxyribonucleotides except that the modified nucleotide on the 5' end, which comprises the 5' leaving group, is a ribonucleotide. This embodiment of the upstream nucleotide is advantageous because the bond between the penultimate 2'-deoxyribonucleotide and the terminal 5' ribonucleotide is susceptible to cleavage using base. This allows for potential reuse of an oligonucleotide probe that is, for example, bound to a solid support, as described in more detail below. In reference to the CLPA assay, which is described more fully below, the 5' leaving group of the "upstream" probe is most preferably DABSYL.

The "downstream" oligonucleotide, which binds to the polynucleotide template "downstream" of, i.e., 3' to, the upstream oligonucleotide, includes, as its 3' end, a nucleoside having linked to its 3' hydroxyl a phosphorothioate group (i.e., a "3'-phosphorothioate group"), a phosphoroselenoate group (i.e., a "3'-phosphoroselenoate group), or a phosphorotelluroate group (i.e., a "3'-phosphorotelluroate group"). The chemistries used for autoligation are thus sulfur-mediated, selenium-mediated, or tellurium mediated. Self-ligation yields a ligation product containing a 5' bridging phosphorothioester (—O—P(O)(O.sup.-)—S—), phosphoroselenoester (—O—P(O)(O.sup.-)—Se—) or phosphorotelluroester (—O—P(O)(O.sup.-)—Te—), as dictated by the group comprising the 3' end of the downstream oligonucleotide. This non-natural, achiral bridging diester is positioned between two adjacent nucleotides and takes the place of a naturally occurring 5' bridging phosphodiester. Surprisingly, the selenium-mediated ligation is 3 to 4 times faster than the sulfur-mediated ligation, and the selenium-containing ligation product was very stable, despite the lower bond strength of the Se—P bond. Further, the bridging phosphoroselenoester, as well as the bridging phosphorotelluroester, are expected to be cleavable selectively by silver or mercuric ions under very mild conditions (see Mag et al., *Nucleic Acids Res*. (1991) 19:1437 1441).

In one embodiment, a downstream oligonucleotide contains 2'-deoxyribonucleotides except that the modified nucleotide on the 3' end, which comprises the 3' phosphorothioate, phosphoroselenoate, or phosphorotelluroate, is a ribonucleotide. This embodiment of the upstream nucleotide is advantageous because the bond between the penultimate 2'-deoxyribonucleotide and the terminal ribonucleotide is susceptible to cleavage using base, allowing for potential reuse of an oligonucleotide probe that is, for example, bound to a solid support. In reference to the CLPA assay, as described more fully below, the "downstream" probe most preferably includes at its 3' end 3'-phosphorothioate.

It should be noted that the "upstream" and "downstream" oligonucleotides can, optionally, constitute the two ends of a single oligonucleotide, in which event ligation yields a circular ligation product. The binding regions on the 5' and 3' ends of the linear precursor oligonucleotide must be linked by a number of intervening nucleotides sufficient to allow binding of the 5' and 3' binding regions to the polynucleotide target.

Compositions provided by the invention include a 5'-deoxy-5-'iodo-2'-deoxynucleoside, for example a 5'-deoxy-5'-iodothymidine (5'-I-T), 5'-deoxy-5'-iodo-2'-deoxycytidine (5'-I-dC), 5'-deoxy-5'-iodo-2'-deoxyadenosine (5'-I-dA), 5'-deoxy-5'-iodo-3-deaza-2'-deoxyadenosine (5'-I-3-deaza-dA), 5'-deoxy-5'-iodo-2'-deoxyguanosine (5'-I-dG) and 5'-deoxy-5'-iodo-3-deaza-2'-deoxyguanosine (5'-I-3-deaza-dG), and the phosphoroamidite derivatives thereof, as well as an oligonucleotide comprising, as its 5' end, a 5'-deoxy-5'-iodo-2'-deoxynucleoside of the invention. Compositions provided by the invention further include a 5'-deoxy-5'-iodonucleoside such as 5'-deoxy-5'-iodouracil (5'-I-U), 5'-deoxy-5'-iodocytidine (5'-I-C), 5'-deoxy-5'-iodoadenosine (5'-1-A), 5'-deoxy-5'-iodo-3-deazaadenosine (5'-I-3-deaza-A), 5'-deoxy-5'-iodoguanosine (5'-I-G) and 5'-deoxy-5'-iodo-3-deazaguanosine (5'-I-3-deaza-G), and the phosphoroamidite derivatives thereof, as well as an oligonucleotide comprising, as its 5' end, a 5'-deoxy-5'-iodonucleoside of the invention. Also included in the invention is a nucleoside comprising a 3'-phosphoroselenoate group or a 3'-phosphorotelluroate group, and an oligonucleotide comprising as its 3' end a nucleoside comprising a 3'-phosphoroselenoate group or a 3'-phosphorotelluroate group. Oligonucleotides containing either or both of these classes of modified nucleosides are also included in the invention, as are methods of making the various nucleosides and oligonucleotides. Oligonucleotides that are modified at either or both of the 5' or 3' ends in accordance with the invention optionally, but need not, include a detectable label, preferably a radiolabel, a fluorescence energy donor or acceptor group, an excimer label, or any combination thereof.

In addition, in some cases, substituent groups may also be protecting groups (sometimes referred to herein as "PG"). Suitable protecting groups will depend on the atom to be protected and the conditions to which the moiety will be exposed. A wide variety of protecting groups are known; for example, DMT is frequently used as a protecting group in phosphoramidite chemistry (as depicted in the figures; however, DMT may be replaced by other protecting groups in these embodiments. A wide variety of protecting groups are suitable; see for example, Greene's Protective Groups in Organic Synthesis, herein incorporated by reference for protecting groups and associated chemistry.

By "alkyl group" or grammatical equivalents herein is meant a straight or branched chain alkyl group, with straight chain alkyl groups being preferred. If branched, it may be branched at one or more positions, and unless specified, at any position. The alkyl group may range from about 1 to about 30 carbon atoms (C1-C30), with a preferred embodiment utilizing from about 1 to about 20 carbon atoms (C1-C20), with about C1 through about C12 to about C15 being preferred, and C1 to C5 being particularly preferred, although in some embodiments the alkyl group may be much larger. Also included within the definition of an alkyl group are cycloalkyl groups such as C5 and C6 rings, and heterocyclic rings with nitrogen, oxygen, sulfur or phosphorus. Alkyl also includes heteroalkyl, with heteroatoms of sulfur, oxygen, nitrogen, and silicone being preferred. Alkyl includes substituted alkyl groups. By "substituted alkyl group" herein is meant an alkyl group further comprising one or more substitution moieties "R", as defined above.

By "amino groups" or grammatical equivalents herein is meant $NH_2$, —NHR and —$NR_2$ groups, with R being as defined herein. In some embodiments, for example in the case of the peptide ligation reactions, primary and secondary amines find particular use, with primary amines generally showing faster reaction rates.

By "nitro group" herein is meant an —$NO_2$ group.

By "sulfur containing moieties" herein is meant compounds containing sulfur atoms, including but not limited to, thia-, thio- and sulfo-compounds, thiols (—SH and —SR), and sulfides (—RSR—). A particular type of sulfur containing moiety is a thioester (—(CO)—S—), usually found as a substituted thioester (—(CO)—SR). By "phosphorus containing moieties" herein is meant compounds containing phosphorus, including, but not limited to, phosphines and phosphates. By "silicon containing moieties" herein is meant compounds containing silicon.

By "ether" herein is meant an —O—R group. Preferred ethers include alkoxy groups, with —O—$(CH_2)_2CH_3$ and —O—$(CH_2)_4CH_3$ being preferred.

By "ester" herein is meant a —COOR group.

By "halogen" herein is meant bromine, iodine, chlorine, or fluorine. Preferred substituted alkyls are partially or fully halogenated alkyls such as $CF_3$, etc.

By "aldehyde" herein is meant —RCOH groups.

By "alcohol" herein is meant —OH groups, and alkyl alcohols —ROH.

By "amido" herein is meant —RCONH— or RCONR— groups.

By "ethylene glycol" herein is meant a —(O—$CH_2$—$CH_2$)$_n$— group, although each carbon atom of the ethylene group may also be singly or doubly substituted, i.e. —(O—$CR_2$—$CR_2$)$_n$—, with R as described above. Ethylene glycol derivatives with other heteroatoms in place of oxygen (i.e. —(N—$CH_2$—$CH_2$)$_n$— or —(S—$CH_2$—$CH_2$)$_n$—, or with substitution groups) are also preferred.

Additionally, in some embodiments, the R group may be a functional group, including quenchers, destabilization moieties and fluorophores (as defined below). Fluorophores of particular use in this embodiment include, but are not limited to Fluorescein and its derivatizes, TAMRA (Tetramethyl-6-carboxyrhodamine), Alexa dyes, and Cyanine dyes (e.g. Cy3 and Cy5).

Quencher moieties or molecules are known in the art, and are generally aromatic, multiring compounds that can deactivate the excited state of another molecule. Fluorophore-quencher pairs are well known in the art. Suitable quencher moieties include, but are not limited to Dabsyl (Dimethyl-amini(azobenzene) sulfonyl) Dabcyl (Dimethylamino (azobenzene)carbonyl), Eclipse Quenchers (Glen Research Catalog) and blackhole Quenchers (BHQ-1, BHQ-2 and BHQ-3) from Biosearch Technologies.

Methods of making probes having halo leaving groups is known in the art; see for example Abe et al., *Proc Natl Aced Sci USA* (2006) 103(2):263-8; Silverman et al., *Nucleic Acids Res*. (2005) 33(15):4978-86; Cuppolletti et al., *Bioconjug Chem*. (2005) 16(3):528-34; Sando et al., *J Am Chem. Soc*. (2004) 4; 126(4):1081-7; Sando et al., *Nucleic Acids Res Suppl*. (2002) 2:121-2; Sando et al., *J Am Chem. Soc*. (2002) 124(10):2096-7; Xu et al., *Nat. Biotechnol*. (2001) 19(2):148-52; Xu et al., *Nucleic Acids Res*. (1998) 26(13):3159-64; Moran et al., *Proc Natl Aced Sci USA* (1997) 94(20):10506-11; Kool, U.S. Pat. No. 7,033,753; Kool, U.S. Pat. No. 6,670,193; Kool, U.S. Pat. No. 6,479,650; Kool, U.S. Pat. No. 6,218,108; Kool, U.S. Pat. No. 6,140,480; Kool, U.S. Pat. No. 6,077,668; Kool, U.S. Pat. No. 5,808,036; Kool, U.S. Pat. No. 5,714,320; Kool, U.S. Pat. No. 5,683,874; Kool, U.S. Pat. No. 5,674,683; and Kool, U.S. Pat. No. 5,514,546, each of which is incorporated herein by reference in its entirety.

Nucleophile Ligation Moieties

In some embodiments, ligation probes of the invention comprise a ligation moiety comprising a nucleophile such as an amine. Ligation moieties comprising both a thiol and an amine find particular use in certain reactions. In general, the nucleophile ligation moieties can include a wide variety of potential amino, thiol compounds as long as the nucleophile ligation moiety contains a thiol group that is proximal to a primary or secondary amino and the relative positioning is such that at least a 5 or 6 member ring transition state can be achieve during the S to N acyl shift.

Accordingly, nucleophile ligation molecules that comprise 1, 2 or 1, 3 amine thiol groups find particular use. Primary amines find use in some embodiments when reaction time is important, as the reaction time is generally faster for primary than secondary amines, although secondary amines find use in acyl transferase reactions that contribute to destabilization as discussed below. The carbons between the amino and thiol groups can be substituted with non-hydrogen R groups, although generally only one non-hydrogen R group per carbon is utilized. Additionally, adjacent R groups may be joined together to form cyclic structures, including substituted and unsubstituted cycloalkyl and aryl groups, including heterocycloalkyl and heteroaryl and the substituted and unsubstituted derivatives thereof. In the case where a 1,2 amino thiol group is used and adjacent R groups are attached, it is generally preferred that the adjacent R groups form cycloalkyl groups (including heterocycloalkyl and substituted derivatives thereof) rather than aryl groups.

In this embodiment, for the generation of the 4 sigma bond contraction of the chain for destabilization, the replacement ligation moiety relies on an acyl transferase reaction.

Linkers

In many embodiments, linkers (sometimes shown herein as "L" or "-(linker)$_n$-", (where n is zero or one) may optionally be included at a variety of positions within the ligation probe(s). Suitable linkers include alkyl and aryl groups, including heteroalkyl and heteroaryl, and substituted derivatives of these. In some instances, for example when Native Peptide Ligation reactions are done, the linkers may be amino acid based and/or contain amide linkages. As described herein, some linkers allow the ligation probes to be separated by one or more nucleobases, forming abasic sites within the ligation product, which serve as destabilization moieties, as described below.

Destabilization Moieties

In accordance with one aspect of the invention, it is desirable to produce multiple copies of ligated product for each target molecule without the aid of an enzyme. One way to achieve this goal involves the ligated product disassociating from the target following the chemical ligation reaction to allow a new probe set to bind to the target. To increase ligation product turnover, probe designs, instrumentation, and chemical ligation reaction chemistries that increase product disassociation from the target molecule are desirable. Suitable destabilization moieties are discussed below and include, but are not limited to molecule entities that result in a decrease in the overall binding energy of an oligonucleotide to its target site. Potential examples include, but are not limited to alkyl chains, charged complexes, and ring structures.

Previous work has shown one way to achieve product disassociation and increase product turnover is to "heat cycle" the reaction mixture. Heat cycling is the process of varying the temperature of a reaction so as to facilitate a desired outcome. Most often heat cycling takes the form of briefly raising the temperature of the reaction mixture so that the reaction temperature is above the melting temperature of the ligated product for a brief period of time causing the product to disassociate from the target. Upon cooling, a new set of probes is able to bind the target, and undergo another ligation reaction. This heat cycling procedure has been practiced extensively for enzymatic reactions like PCR.

While heat cycling is one way to achieve product turnover, it is possible to design probes such that there is significant product turnover without heat cycling. Probe designs and ligation chemistries that help to lower the melting temperature of the ligated product increase product turnover by decreasing product inhibition of the reaction cycle.

Accordingly, in one aspect, the probes are designed to include elements (e.g. destabilization moieties), which, upon ligation of the probes, serve to destabilize the hybridization of the ligation product to the target sequence. As a result, the ligated substrate disassociates after ligation, resulting in a turnover of the ligation product, e.g. the ligation product comprising the two ligation probes dehybridizes from the target sequence, freeing the target sequence for hybridization to another probe set.

In addition, increasing the concentration of the free (e.g. unhybridized) ligation probes can also help drive the equilibrium towards release of the ligation product (or transfer product) from the target sequence. Accordingly, some embodiments of the invention use concentrations of probes that are 1,000,000 fold higher than that of the target while in other embodiments the probes are 10,000 to 100 fold higher than that of the target. As will be appreciated by those skilled in the art, increasing the concentration of free probes can be used by itself or with any embodiment outlined herein to achieve product turnover (e.g. amplification). While increasing the probe concentration can result in increased product turnover, it can also lead to significant off target reactions such as probe hydrolysis and non-target mediated ligation.

In one aspect, probe elements include structures which lower the melting temperature of the ligated product. In some embodiments, probe elements are designed to hybridize to non-adjacent target nucleobases, e.g. there is a "gap" between the two hybridized but unligated probes. In general, this is done by using one or two linkers between the probe domain and the ligation moiety. That is, there may be a linker between the first probe domain and the first ligation moiety, one between the second probe domain and the second ligation moiety, or both. In some embodiments, the gap comprises a single nucleobase, although more can also be utilized as desired. As will be appreciated by those skilled in the art, there may be a tradeoff between reaction kinetics and length of the linkers; if the length of the linker(s) are so long that contact resulting in ligation is kinetically disfavored, shorter linkers may be desired. However, in some cases, when kinetics are not important, the length of the gap and the resulting linkers may be longer, to allow spanning gaps of 1 to 10 nucleobases. Generally, in this embodiment, what is important is that the length of the linker(s) roughly corresponds to the number of nucleobases in the gap.

In another aspect of this embodiment of the invention, the formation of abasic sites in a ligation product as compared to the target sequence serves to destabilize the duplex. For example, Abe and Kool (*J. Am. Chem. Soc.* (2004) 126: 13980-13986) compared the turnover when two different 8-mer oligonucleotide probes (Bu42 and DT40) were ligated with the same 7-mer probe (Thio 4). When Thio4 is ligated with DT40, a continuous 15-mer oligonucleotide probe with a nearly native DNA structure is formed that should be perfectly matched with the DNA target. However, when Thio4 is ligated with Bu42, a 15-mer oligonucleotide probe is formed, but when the probe is bound to the target, it has an abasic site in the middle that is spanned by an alkane linker. Comparison of the melting temperature (Tm) of these two probes when bound to the target shows approximately a 12° C. difference in melting temperature (58.5 for Bu42 versus 70.7° C. for DT40). This 12° C. difference in melting temperature led to roughly a 10-fold increase in product turnover (91.6-Bu42 versus 8.2 DT40) at 25° C. when the probe sets (10.000-fold excess, 10 µM conc) were present in large excess compared to the target (1 nM). Similarly, Dose et al (Dose 2006) showed how a 4° C. decrease in Tm for two identical sequences, chemically ligated PNA probes (53° C. versus 57° C.) results in approximately a 4-fold increase in product turnover.

Recent work has demonstrated the use of chemical ligation based Quenched Auto-Ligation (QUAL) probes to monitor RNA expression and detect single base mismatches inside bacterial and human cells (WO 2004/0101011 herein incorporated by reference).

In one embodiment, destabilization moieties are based on the removal of stabilization moieties. That is, if a ligation probe contains a moiety that stabilizes its hybridization to the target, upon ligation and release of the stabilization moiety, there is a drop in the stability of the ligation product. Accordingly, one general scheme for reducing product inhibition is to develop probes that release a molecular entity like a minor groove binding molecule during the course of the initial chemical ligation reaction or following a secondary reaction post ligation. Depending on the oligonucleotide sequence, minor groove binders like the dihydropyrroloindole tripeptide ($DPI_3$) described by Kutyavin (Kutyavin 1997 and Kutyavin 2000) can increase the Tm of a duplex nucleic acid by up to 40° C. when conjugated to the end of an oligonucleotide probe. In contrast, the unattached version of the DPI3 only increases the Tm of the same duplex by 2° C. or so. Thus, minor groove binders can be used to produce probe sets with enhanced binding strengths, however if the minor groove binder is released during the course of the reaction, the binding enhancement is loss and the ligated product will display a decreased Tm relative to probes in which the minor groove binder is still attached.

Suitable minor groove binding molecules include, but are not limited to, dihydropyrroloindole tripeptide ($DPI_3$), distamycin A, and pyrrole-imidazole polyamides (Gottesfeld, J. M., et al., *J. Mol. Biol.* (2001) 309:615-629.

In addition to minor groove binding molecules tethered intercalators and related molecules can also significantly increase the melting temperature of oligonucleotide duplexes, and this stabilization is significantly less in the untethered state. (Dogan, et al., *J. Am. Chem. Soc.* (2004) 126:4762-4763 and Narayanan, et al., *Nucleic Acids Research*, (2004) 32:2901-2911).

Similarly, as will be appreciated by those in the art, probes with attached oligonucleotide fragments (DNA, PNA, LNA, etc) capable of triple helix formation, can serve as stabilization moieties that upon release, results in a decrease of stabilization of the ligation product to the target sequence (Pooga, M, et al., *Biomolecular Engineering* (2001) 17:183-192.

Another general scheme for decreasing product inhibition by lowering the binding strength of the ligated product is to incorporate abasic sites at the point of ligation. This approach has been previously demonstrated by Abe (*J. Am. Chem. Soc.* (2004) 126:13980-13986), however it is also possible to design secondary probe rearrangements to further amplify the decrease in Tm via straining the alignment between the ligated probes and the target. For example, Dose et al. (*Org. Letters* (2005) 7:20 4365-4368) showed how a rearrangement post-ligation that changed the spacing between PNA bases from the ideal 12 sigma bonds to 13 resulted in a lowering of the Tm by 4° C. Larger rearrangements and secondary reactions that interfere with the binding of the product to the target or result in the loss of oligonucleotide bases can further decrease the Tm.

The present invention provides methods and compositions for a ligation reaction that results in a chain contraction of up to 4 sigma bonds during the rearrangement, which should have a significant effect on the Tm post-rearrangement compared to the 1 base expansion using the chemistry described by Dose. This chemistry is based on the acyl transfer auxiliary that has been described previously (Offer et al., *J Am Chem. Soc.* (2002) 124(17):4642-6). Following completion of the chain contraction, a free-thiol is generated that is capable of undergoing another reaction either with a separate molecule or with itself. For example, this thiol could react with an internal thioester to severely kink the oligonucleotide and thus further decrease the ligation product's ability to bind to the target.

Thus, in this embodiment, ligation reactions that release functional groups that will undergo a second reaction with the ligation product can reduce stabilization of the hybrid of the ligation product and the target sequence.

Variable Spacer Sequences

In addition to the target domains, ligation moieties, and optional linkers, one or more of the ligation probes of the invention can have variable spacer sequences (also referred to as "stuffer sequences"). These variable spacer sequences are of particular use in the CLPA-CE assays described in further detail herein. That is, the variable spacer sequence can serve as a type of "label" or "barcode" to identify the target sequence when the products are detected on the basis of length, for example using capillary electrophoresis (CE).

Variable spacer sequences are domains of ligation probes that can have varying lengths. These varying lengths will in some embodiments be specific to a particular target sequence to which other domains of the ligation probe (e.g., the probe domain) are able to hybridize, such that the length of the ligation product resulting from ligation of ligation probes containing stuffer sequences is a target-specific length. As a result, any amplicons generated from such ligation products will also have a target-specific length. In other embodiments, the variable spacer sequence is designed to render all ligation products of similar length so as to facilitate the efficiency of subsequent amplification reactions.

In some embodiments, only one of the ligation probes of a ligation probe pair comprises a variable spacer sequence. In other embodiments, both ligation probes comprise the variable spacer sequence. In embodiments in which three or more ligation probes are used, one or more of the ligation probes forming a particular ligation product can contain the variable spacer sequence, although in this embodiment is it generally one or both of the terminal probes that contains the variable spacer sequence.

In further embodiments and in accordance with any of the above, the variable spacer sequence is contained within a region of the ligation probe that is substantially non-complementary to both any other domains of the target nucleic acid as well as to any of the target nucleic acids in a sample.

In still further embodiments, the ligation probes (as will be discussed in further detail below) contain a primer sequence. In accordance with any of the above, the variable spacer sequence is in some embodiments contained between the probe domain (the region of the ligation probe that hybridizes to a target sequence) and the primer sequence, such that the amplicon contains the variable spacer sequence.

In further aspects, variable spacer sequences of the invention include nucleic acids such as DNA or RNA. Variable spacer sequences may also include a combination of both deoxyribonucleotides and ribonucleotides. Variable spacer sequences may further include nucleotide analogues, linkers, or any of the additional moieties discussed herein as optionally present in ligation and/or target capture probes of the invention.

Figure 6:
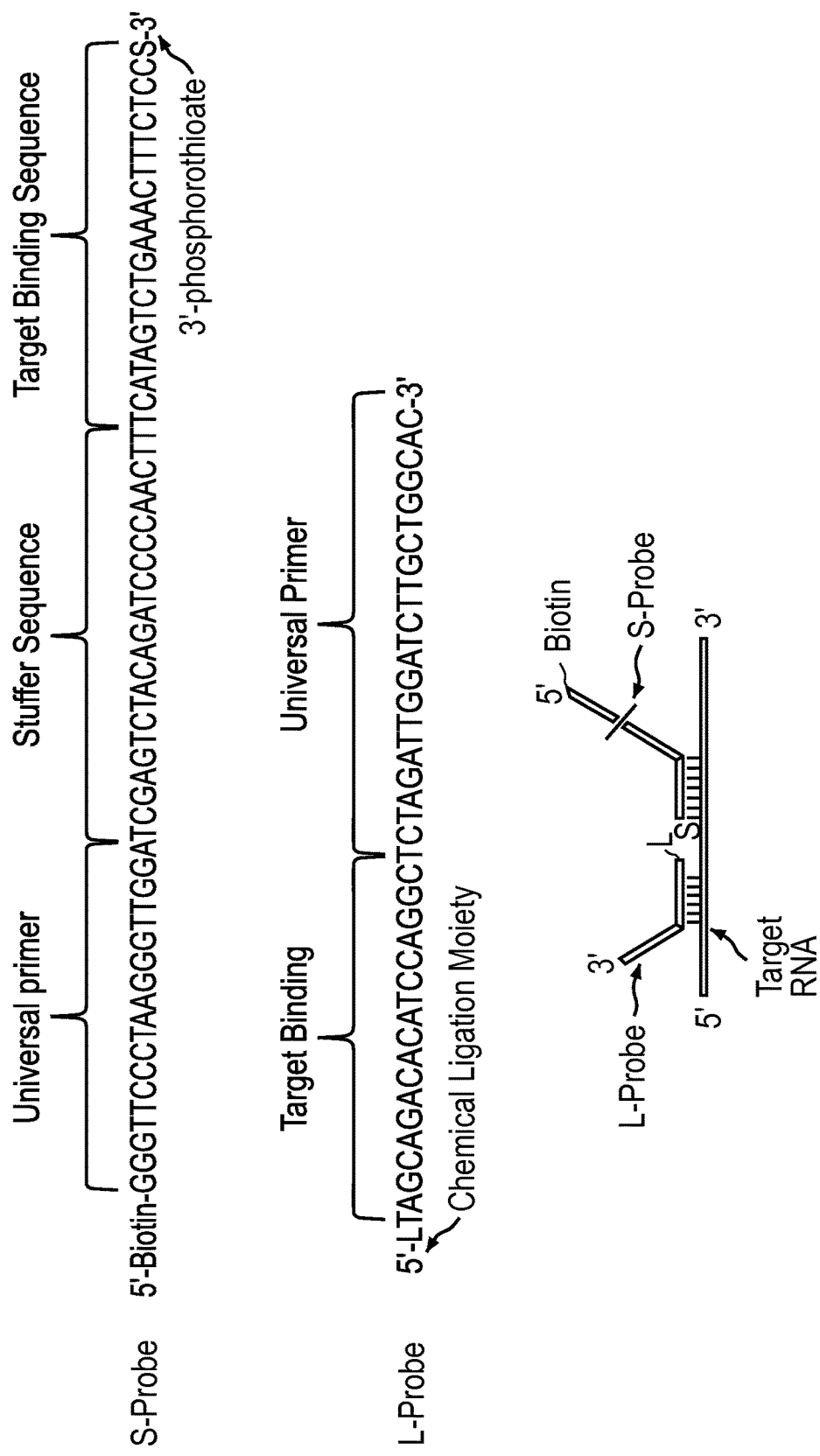
FIG. 6 is a schematic representation showing probe design for a CLPA assay in which the probe contains a size-variant stuffer sequence.

In general, for multiplex assays where multiple target sequences are to be detected simultaneously, variable spacer sequences are designed to result in either or both of the ligation product or (in the case where an amplification reaction follows the ligation step) the resulting amplicons from each ligation product to have a different nucleotide length from other ligation products or amplicons in the sample. That is, the amplicon from one target nucleic acid will be different from the length of the amplicon from a different target nucleic acid. Similarly, when multiple ligation probe sets are used for a single target as is shown in FIGS. 6 and 11, each ligation product and/or amplicon will have a different length, allowing detection of the different products.

The differing lengths of the variable spacer sequences will depend on the sensitivity of the detection system. For sophisticated Capillary electrophoresis (CE) systems, such as Genetic Analyzer systems made by Life Technologies or the PACE systems by Beckman Coulter, ligation products and/or amplicons can be separated and thus detected when they differ in length by as few as one nucleotide. Other CE systems with lower size resolution, may require length differences of 5 to 100 base pairs depending on the resolution. In general, higher resolution CE systems require longer separation channel lengths and often longer separation times. Furthermore, denaturing capillary electrophoresis systems tend to have better resolution than non-denaturing systems. In general, the variable spacer sequences are designed to result in nucleotide differences ranging from 1 to 100 bases with 5 to 20 bases being preferred. Greater size differences can be used, but often require additional cost or reduce the number of possible ligation probes that can be combined in a single test.

In addition, variable spacer sequences can be used in conjunction with other labels to expand the number of different "barcodes" that can be used. That is, a variable spacer sequence length can be "reused" by encoding it with a second label; for example, one amplicon containing a variable spacer sequence of 20 nucleotides can use a fluorescent label of a first color, and another amplicon containing the 20 mer spacer sequence can use a fluorescent label of a different color. These amplicons of the same size can be simultaneously detected using a multi-channel CE instrument that can identify amplicons with different wavelength (color) products like is commonly practiced in forensic medicine.

Additional Functionalities of Ligation Probes

In addition to the target domains, ligation moieties, and optional linkers, one or more of the ligation probes of the invention can have additional functionalities, including, but not limited to, promoter and primer sequences (or complements thereof, depending on the assay), labels, including label probe binding sequences, and capture or anchor sequences.

In many embodiments, the ligation probes are constructed so as to contain the necessary priming site or sites for the subsequent amplification scheme. In a preferred embodiment the priming sites are universal priming sites. By "universal priming site" or "universal priming sequences" herein is meant a sequence of the probe that will bind a primer for amplification.

In a preferred embodiment, one universal priming sequence or site is used. In this embodiment, a preferred universal priming sequence is the RNA polymerase T7 sequence, that allows the T7 RNA polymerase make RNA copies of the adapter sequence as outlined below. Additional disclosure regarding the use of T7 RNA polymerase is found in U.S. Pat. Nos. 6,291,170, 5,891,636, 5,716,785, 5,545,522, 5,922,553, 6,225,060 and 5,514,545, all of which are expressly incorporated herein by reference.

In a preferred embodiment, for example when amplification methods requiring two primers such as PCR are used, each probe preferably comprises an upstream universal priming site (UUP) and a downstream universal priming site (DUP). Again, "upstream" and "downstream" are not meant to convey a particular 5'-3' orientation, and will depend on the orientation of the system. Preferably, only a single UUP sequence and a single DUP sequence is used in a probe set, although as will be appreciated by those in the art, different assays or different multiplexing analysis may utilize a plurality of universal priming sequences. In some embodiments probe sets may comprise different universal priming sequences. In addition, the universal priming sites are preferably located at the 5' and 3' termini of the target probe (or the ligated probe), as only sequences flanked by priming sequences will be amplified.

In addition, universal priming sequences are generally chosen to be as unique as possible given the particular assays and host genomes to ensure specificity of the assay. However, as will be appreciated by those in the art, sets of priming sequences/primers may be used; that is, one reaction may utilize 500 target probes with a first priming sequence or set of sequences, and an additional 500 probes with a second sequence or set of sequences.

As will be appreciated by those in the art, when two priming sequences are used, the orientation of the two priming sites is generally different. That is, one PCR primer will directly hybridize to the first priming site, while the other PCR primer will hybridize to the complement of the second priming site. Stated differently, the first priming site is in sense orientation, and the second priming site is in antisense orientation.

As will be appreciated by those in the art, in general, highly multiplexed reactions can be performed, with all of the universal priming sites being the same for all reactions. Alternatively, "sets" of universal priming sites and corresponding probes can be used, either simultaneously or sequentially. The universal priming sites are used to amplify the modified probes to form a plurality of amplicons that are then detected in a variety of ways, as outlined herein. In preferred embodiments, one of the universal priming sites is a T7 site. In some embodiments this priming site serves as a template for the synthesis of RNA.

In a preferred embodiment, when detecting multiple targets simultaneously, all of the oligonucleotide ligation probe sets in the reaction are designed to contain identical promoter or primer pair binding sites such that following ligation and purification, if appropriate, all of the ligated products can be amplified simultaneously using the same enzyme and/or same primers. In other words, in embodiments involving the detection of multiple target nucleic acids, different ligation probe sets containing ligation probes directed to different target nucleic acid sequences can in some embodiments possess identical promoter or primer pair binding sites (e.g., "universal" primer binding sites) such that the ligation products resulting from the hybridization and ligation of these ligation probes can be amplified using the same enzyme and/or primers.

In one embodiment, one or more of the ligation probes comprise a promoter sequence. In embodiments that employ a promoter sequence, the promoter sequence or its complement will be of sufficient length to permit an appropriate polymerase to interact with it. Detailed descriptions of sequences that are sufficiently long for polymerase interaction can be found in, among other places, Sambrook and Russell, which are hereby incorporated by reference for all purposes and in particular for all teachings related to promoter sequences for polymerases. In certain embodiments, amplification methods comprise at least one cycle of amplification, for example, but not limited to, the sequential procedures of: interaction of a polymerase with a promoter; synthesizing a strand of nucleotides in a template-dependent manner using a polymerase; and denaturing the newly-formed nucleic acid duplex to separate the strands.

In another embodiment, one or both of the ligation probes comprise a primer sequence. As outlined below, the ligation products of the present invention may be used in additional reactions such as enzymatic amplification reactions. In one embodiment, the ligation probes include primer sequences designed to allow an additional level of amplification. As used herein, the term "primer" refers to nucleotide sequence, whether occurring naturally as in a purified restriction digest or produced synthetically, which is capable of acting as a point of initiation of nucleic acid sequence synthesis when placed under conditions in which synthesis of a primer extension product which is complementary to a nucleic acid strand is induced, i.e. in the presence of different nucleotide triphosphates and a polymerase in an appropriate buffer ("buffer" includes pH, ionic strength, cofactors etc.) and at a suitable temperature. One or more of the nucleotides of the primer can be modified, for instance by addition of a methyl group, a biotin or digoxigenin moiety, a fluorescent tag or by using radioactive nucleotides. A primer sequence need not reflect the exact sequence of the template. For example, a non-complementary nucleotide fragment may be attached to the 5' end of the primer, with the remainder of the primer sequence being substantially complementary to the target strand.

By using several priming sequences and primers, a first ligation product can serve as the template for additional ligation products. These primer sequences may serve as priming sites for PCR reactions, which can be used to amplify the ligation products. In addition to PCR reactions, other methods of amplification can utilize the priming sequences, including but not limited to ligase chain reactions, Invader™, positional amplification by nick translation (NICK), primer extension/nick translation, and other methods known in the art. As used herein, "amplification" refers to an increase in the number of copies of a particular nucleic acid. Copies of a particular nucleic acid made in vitro in an amplification reaction are called "amplicons" or "amplification products".

Amplification may also occur through a second ligation reaction, in which the primer sites serve as hybridization sites for a new set of ligation probes which may or may not comprise sequences that are identical to the first set of ligation probes that produced the original ligation products. The target sequence is thus exponentially amplified through amplification of ligation products in subsequent cycles of amplification.

In another embodiment of this aspect of the invention, the primer sequences are used for nested ligation reactions. In such nested ligation reactions, a first ligation reaction is accomplished using methods described herein such that the ligation product can be captured, for example by using biotinylated primers to the desired strand and capture on beads (particularly magnetic beads) coated with streptavidin. After the ligation products are captured, a second ligation reaction is accomplished by hybridization of ligation probes to primer sequences within a section of the ligation product which is spatially removed from (i.e., downstream from) the end of the ligation product which is attached to the capture bead, probe, etc. At least one of the primer sequences for the secondary ligation reaction will be located within the region of the ligation product complementary to the ligation probe which is not the ligation probe that included the anchor or capture sequence. The ligation products from this second ligation reaction will thus necessarily only result from those sequences successfully formed from the first chemical ligation, thus removing any "false positives" from the amplification reaction. In another embodiment, the primer sequences used in the secondary reaction may be primer sites for other types of amplification reactions, such as PCR.

In one embodiment, one or more of the ligation probes comprise an anchor sequence. By "anchor sequence" herein is meant a component of a ligation probe that allows the attachment of a ligation product to a support for the purposes of detection. Suitable means for detection include a support having attached thereto an appropriate capture moiety. Generally, such an attachment will occur via hybridization of the anchor sequence with a capture probe, which is substantially complementary to the anchor sequence.

In a preferred embodiment, one of the probes further comprises an "anchor" sequence, (sometimes referred to in the art and herein as "zip codes" or "bar codes" or "adapters"). Adapters facilitate immobilization of probes to allow the use of "universal arrays". That is, arrays (either solid phase or liquid phase arrays) are generated that contain capture probes that are not target specific, but rather specific to individual (preferably) artificial adapter sequences.

Thus, an "adapter sequence" is a nucleic acid that is generally not native to the target sequence, i.e. is exogenous, but is added or attached to the target sequence. It should be noted that in this context, the "target sequence" can include the primary sample target sequence, or can be a derivative target such as a reactant or product of the reactions outlined herein; thus for example, the target sequence can be a PCR product, a first ligation probe or a ligated probe in an OLA reaction, etc. The terms "barcodes", "adapters", "addresses", "tags" and "zipcodes" have all been used to describe artificial sequences that are added to amplicons to allow separation of nucleic acid fragment pools. One preferred form of adapters are hybridization adapters. In this embodiment adapters are chosen so as to allow hybridization to the complementary capture probes on a surface of an array. Adapters serve as unique identifiers of the probe and thus of the target sequence. In general, sets of adapters and the corresponding capture probes on arrays are developed to minimize cross-hybridization with both each other and other components of the reaction mixtures, including the target sequences and sequences on the larger nucleic acid sequences outside of the target sequences (e.g. to sequences within genomic DNA). Other forms of adapters are mass tags that can be separated using mass spectroscopy, electrophoretic tags that can be separated based on electrophoretic mobility, etc. Some adapter sequences are outlined in U.S. Ser. No. 09/940,185, filed Aug. 27, 2001, hereby incorporated by reference in its entirety. Preferred adapters are those that meet the following criteria. They are not found in a genome, preferably a human genome, and they do not have undesirable structures, such as hairpin loops.

In one embodiment the use of adapter sequences allow the creation of more "universal" surfaces; that is, one standard array, comprising a finite set of capture probes can be made and used in any application. The end-user can customize the array by designing different soluble target probes, which, as will be appreciated by those in the art, is generally simpler and less costly. In a preferred embodiment, an array of different and usually artificial capture probes are made; that is, the capture probes do not have complementarity to known target sequences. The anchor sequences can then be incorporated in the target probes.

As will be appreciated by those in the art, the length of the anchor sequences will vary, depending on the desired "strength" of binding and the number of different anchor desired. In a preferred embodiment, adapter sequences range from about 6 to about 500 basepairs in length, with from about 8 to about 100 being preferred, and from about 10 to about 25 being particularly preferred.

In a preferred embodiment, the adapter sequence uniquely identifies the target analyte to which the target probe binds. That is, while the adapter sequence need not bind itself to the target analyte, the system allows for identification of the target analyte by detecting the presence of the adapter. Accordingly, following a binding or hybridization assay and washing, the probes including the adapters are amplified. Detection of the adapter then serves as an indication of the presence of the target nucleic acid.

In one embodiment the adapter includes both an identifier region and a region that is complementary to capture probes on a universal array as described above. In this embodiment, the amplicon hybridizes to capture probes on a universal array. Detection of the adapter is accomplished following hybridization with a probe that is complementary to the adapter sequence. Preferably the probe is labeled as described herein.

In general, similar to variable spacer sequences, unique adapter sequences are used for each unique target analyte. That is, the elucidation or detection of a particular adapter sequence allows the identification of the target analyte to which the target probe containing that adapter sequence bound. However, as discussed herein, in some cases, it is possible to "reuse" adapter sequences and have more than one target analyte share an adapter sequence.

In a preferred embodiment the adapters contain different sequences or properties that are indicative of a particular target molecule. That is, each adapter uniquely identifies a target sequence. As described above, the adapters are amplified to form amplicons. The adapter is detected as an indication of the presence of the target analyte, i.e. the particular target nucleic acid.

In one embodiment of this aspect of the invention, the upstream oligonucleotide is designed to have an additional nucleotide segment that does not bind to the target of interest, but is to be used to subsequently capture the ligated product on a suitable solid support or device of some sort. In a preferred embodiment of this aspect of the invention, the downstream oligonucleotide has a detectable label attached to it, such that following ligation, the resulting product will contain a capture sequence for a solid support at its 3' end and a detectable label at its 5' end, and only ligated products will contain both the capture sequence and the label.

In another aspect of the invention pertaining in particular to multiplex target detection, each upstream probe of a probe set may be designed to have a unique sequence (also referred to herein as an "anchor sequence) at is 3' end that corresponds to a different position on a DNA array. Each downstream probe of a probe set may optionally contain a detectable label that is identical to the other downstream probes, but a unique target binding sequence that corresponds to its respective targets. Following hybridization with the DNA array, only ligated probes that have both an address sequence (upstream probe) and a label (downstream probe) will be observable. In another aspect of the invention, the detectable label can be attached to the upstream probe and the capture sequence can be a part of the downstream probe, such that the ligated products will have the detectable label more towards the 3' end and the capture sequence towards the 5' end of the ligated product. The exact configuration is best determined via consideration of the ease of synthesis as well as the characteristics of the devices to be used to subsequently detect the ligated reaction product.

The anchor sequence may have both nucleic and non-nucleic acid portions. Thus, for example, flexible linkers such as alkyl groups, including polyethylene glycol linkers, may be used to provide space between the nucleic acid portion of the anchor sequence and the support surface. This may be particularly useful when the ligation products are large.

In addition, in some cases, sets of anchor sequences that correspond to the capture probes of "universal arrays" can be used. As is known in the art, arrays can be made with synthetic generic sequences as capture probes, that are designed to non-complementary to the target sequences of the sample being analyzed but to complementary to the array binding sequences of the ligation probe sets. These "universal arrays" can be used for multiple types of samples and diagnostics tests because same array binding sequences of the probes can be reused/paired with different target recognition sequences.

In one embodiment, one or more of the ligation probes comprise a label. By "label" or "labeled" herein is meant that a compound has at least one element, isotope or chemical compound attached to enable the detection of the compound, e.g. renders a ligation probe or ligation or transfer product detectable using known detection methods, e.g., electronic, spectroscopic, photochemical, or electrochemiluminescent methods. In general, labels fall into three classes: a) isotopic labels, which may be radioactive or heavy isotopes; b) magnetic, electrical, thermal; and c) colored or luminescent dyes; although labels include enzymes and particles such as magnetic particles as well. The dyes may be chromophores or phosphors but are preferably fluorescent dyes, which due to their strong signals provide a good signal-to-noise ratio. Suitable dyes for use in the invention include, but are not limited to, fluorescent lanthanide complexes, including those of Europium and Terbium, fluorescein, fluorescein isothiocyanate, carboxy-fluorescein (FAM), dichlorotriazinylamine fluorescein, rhodamine, tetramethylrhodamine, umbelliferone, eosin, erythrosin, coumarin, methyl-coumarins, pyrene, Malacite green, Cy3, Cy5, stilbene, Lucifer Yellow, Cascade Blue™, Texas Red, alexa dyes, dansyl chloride, phycoerythrin, green fluorescent protein and its wavelength shifted variants, bodipy, and others known in the art such as those described in Haugland, Molecular Probes Handbook, (Eugene, Oreg.) 6th Edition; The Synthegen catalog (Houston, Tex.), Lakowicz, Principles of Fluorescence Spectroscopy, 2nd Ed., Plenum Press New York (1999), and others described in the 6th Edition of the Molecular Probes Handbook by Richard P. Haugland, herein expressly incorporated by reference. Additional labels include nanocrystals or Q-dots as described in U.S. Ser. No. 09/315,584, herein expressly incorporated by reference.

In a preferred embodiment, the label is a secondary label that part of a binding partner pair. For example, the label may be a hapten or antigen, which will bind its binding partner. In a preferred embodiment, the binding partner can be attached to a solid support to allow separation of extended and non-extended primers. For example, suitable binding partner pairs include, but are not limited to: antigens (such as proteins (including peptides)) and antibodies (including fragments thereof (FAbs, etc.)); proteins and small molecules, including biotin/streptavidin; enzymes and substrates or inhibitors; other protein-protein interacting pairs; receptor-ligands; and carbohydrates and their binding partners. Nucleic acid-nucleic acid binding protein pairs are also useful. In general, the smaller of the pair is attached to the NTP for incorporation into the primer. Preferred binding partner pairs include, but are not limited to, biotin (or imino-biotin) and streptavidin, digeoxinin and Abs, and Prolinx™ reagents.

In a preferred embodiment, the binding partner pair comprises biotin or imino-biotin and streptavidin. Imino-biotin is particularly preferred as imino-biotin disassociates from streptavidin in pH 4.0 buffer while biotin requires harsh denaturants (e.g. 6 M guanidinium HCl, pH 1.5 or 90% formamide at 95° C.).

In a preferred embodiment, the binding partner pair comprises a primary detection label (for example, attached to a ligation probe) and an antibody that will specifically bind to the primary detection label. By "specifically bind" herein is meant that the partners bind with specificity sufficient to differentiate between the pair and other components or contaminants of the system. The binding should be sufficient to remain bound under the conditions of the assay, including wash steps to remove non-specific binding. In some embodiments, the dissociation constants of the pair will be less than about $10^{-4}$ to $10^{-6}$ $M^{-1}$, with less than about $10^{-5}$ to $10^{-9}$ $M^{-1}$ being preferred and $10^{-9}$ $M^{-1}$ being particularly preferred.

In a preferred embodiment, the secondary label is a chemically modifiable moiety. In this embodiment, labels comprising reactive functional groups are incorporated into the nucleic acid. The functional group can then be subsequently labeled with a primary label. Suitable functional groups include, but are not limited to, amino groups, carboxy groups, maleimide groups, oxo groups and thiol groups, with amino groups and thiol groups being particularly preferred. For example, primary labels containing amino groups can be attached to secondary labels comprising amino groups, for example using linkers as are known in the art; for example, homo- or hetero-bifunctional linkers as are well known (see 1994 Pierce Chemical Company catalog, technical section on cross-linkers, pages 155 200, incorporated herein by reference).

In this embodiment, the label may also be a label probe binding sequence or complement thereof. By "label probe" herein is meant a nucleic acid that is substantially complementary to the binding sequence and is labeled, generally directly.

The compositions of the invention are generally made using known synthetic techniques. In general, methodologies based on standard phosphoramidite chemistries find particular use in one aspect of the present invention, although as is appreciated by those skilled in the art, a wide variety of nucleic acid synthetic reactions are known. The spacing of the addition of fluorophores and quenchers is well known as well.

VI. Target Capture Probes

In certain aspects, and in accordance with any of the description of ligation probes discussed herein, the present invention further includes the use of target capture probes. These target capture probes do not generally participate in the chemical ligation reactions of the ligation probes, and are useful for increasing the specificity of assays. As is described further herein, the target capture probes are hybridized to the target nucleic acid either upstream or downstream from the ligation product formed from ligation probes as described herein. Hybridizing the target capture probe to the target nucleic acid forms a target complex that comprises the target nucleic acid, one or more ligation products, and the target capture probe. The target capture probe contains a capture moiety that can be used to capture the target complex on a solid support or a bead. Following capture on the support or bead, the non-bound species are removed. The target complex (also referred to herein as a "capture complex") and/or the ligation products is then either analyzed or subjected to amplification (such as PCR).

In general, target capture probes of the invention contain a domain that hybridizes to the target nucleic acid and an additional capture moiety that can be used to selectively capture complexes/molecules that are bound to the target capture through hybridization or other interactions. In some embodiments, the capture moiety can be a capture nucleic acid sequence, a bead, or a binding partner of a binding partner pair (such as biotin, which can then be captured with its binding partner streptavidin).

Target capture probes are designed to hybridize upstream or downstream from ligation probes hybridized to target domains of a nucleic acid. In certain embodiments, target capture probes will hybridize within a predetermined distance to the ligation probes.

As is discussed herein, methods of the invention include the hybridization of two or more ligation probes to target domains of a target nucleic acid under conditions such that the ligation probes spontaneously undergo a chemical ligation without the addition of a ligase enzyme. In embodiments of the invention that use target capture probes along with ligation probes, it will be appreciated that the target capture probes can be hybridized to the target nucleic acid prior to, subsequent to or simultaneously with hybridization of the one or more ligation probes. Similarly, hybridization of the target capture probes may also occur prior to, subsequent to or simultaneously with the spontaneous ligation of the ligation probes.

In certain embodiments, multiple target capture probes are applied to a target nucleic acid. As will be appreciated, these multiple capture probes can be designed to hybridize to any point along the length of the target. In embodiments in which a single ligation product is formed on a target nucleic acid, multiple ligation probes may be used to flank the ligation product on either side. This embodiment is of particular use in quality control or assessments of nucleic acid integrity, because there is an increased likelihood that even a degraded target nucleic acid will be captured when multiple target capture probes are used.

In embodiments in which multiple ligation products are formed on a target nucleic acid, multiple target capture probes may also be hybridized to the target nucleic acid. As discussed above, these multiple target capture probes may be designed to hybridize at different points along the length of the target nucleic acid. In some embodiments, target capture probes are designed to hybridize at or near the 3', 5' or both the 3' and 5' end of the target nucleic acid. In further embodiments, the target capture probes are designed to be hybridized to regions upstream, downstream, and/or interleaved between the different ligation products formed on a target nucleic acid.

VII. Assays and Detection Methods

In exemplary aspects, the present invention provides methods for detecting a plurality of different target nucleic acids in a sample. Such target nucleic acids include at least a first and a second target domain, where the first and second target domains are adjacent to each other. The target nucleic acids can also include a third domain that is a target capture domain, and that target capture domain is located upstream or downstream (i.e., 5' or 3') to the first and second target domains.

In preferred embodiments, assays of the invention include the steps of providing ligation substrates that include a target nucleic acid comprising the target domains and target capture domains discussed above. These ligation substrates each further include a first set of ligation probes comprising a first and second nucleic acid ligation probe. The first nucleic acid ligation probe is hybridized to the first target domain of the target nucleic acid sequence, and the second nucleic acid ligation probe is hybridized to the second target domain of the target nucleic acid sequence. In such embodiments, the first target domain is upstream of the second target domain. The first nucleic acid ligation probe further includes a 5' ligation moiety and the second nucleic acid ligation probe further includes a 3' ligation moiety. Since the first and second target domains are adjacent to each other, the ligation moieties of the two ligation probes hybridized to the target domains are adjacent to each other and are able to undergo ligation without the use of a ligase enzyme to form a ligation product.

Embodiments of the invention further include hybridizing a target capture probe to the third target capture domain of the target nucleic acid to form a target complex. The target complex thus comprises the target nucleic acid, the first ligation probe hybridized to the first target domain, the second ligation probe hybridized to the second ligation domain and the target capture probe hybridized to the third target capture domain. The target capture probe comprises a capture moiety, enabling capture of the target complex on a surface or substrate (such as a bead). Capturing the target complex can be used to separate the target complex from unbound target nucleic acids and ligation probes—in other words, use of a target capture probes provides a way to isolate those target nucleic acids on which a ligation product has successfully been formed.

Assays of the invention can further include amplifying the ligation product formed from the different ligation substrates to form amplicons and then detecting the amplicons to detect the target nucleic acids.

As will be appreciated, assays of the invention may utilize multiple sets of ligation probes directed to multiple target domains. For example, the nucleic acids can further include a fourth target domain adjacent to a fifth target domain, and the ligation substrates further include a second set of ligation probes that include a third ligation probe hybridized to the fourth target domain and a fourth ligation probe hybridized to the fifth target domain. As with the first and second ligation probes discussed above, the third and fourth ligation probes ligate without the use of a ligase enzyme, and thus the target nucleic acid comprises multiple ligation products. Target capture probes can again be hybridized to the target nucleic acids to form target complexes comprising the multiple ligation products, the target nucleic acid and the target capture probes. As discussed above, these target complexes can be captured on a surface and the multiple ligation products can in some embodiments be amplified to form amplicons, which can then be detected.

Similarly, the target nucleic acids can further include a sixth target domain adjacent to a seventh target domain, and a third set of ligation probes containing fifth and sixth ligation probes can be hybridized to the sixth and seventh target domains respectively. As with any of the ligation probes discussed herein, the fifth and sixth ligation probes are ligated without the use of a ligase enzyme, thus producing a target nucleic acid comprising multiple ligation products (i.e., the ligation product formed from the ligation of the first and second ligation probes and/or the ligation product formed from the third and fourth ligation probes). As will be appreciated, a target nucleic acid may contain any number of target domains, and thus any number of ligation probe sets can be used to form ligation products on that target nucleic acid in accordance with the present invention.

Any of the above target nucleic acids comprising multiple ligation products may further be hybridized with one or more target capture probes to form target complexes. Those target complexes can then be captured on a substrate. The ligation products of the target complexes are then amplified using methods known in the art and discussed herein to form amplicons, and those amplicons are then detected to identify and/or quantify the presence of target nucleic acids.

In certain embodiments, the ligation products formed in accordance with any of the methods described herein are not amplified but are instead directly detected using any of the methods described herein.

Prior to detecting the ligation or transfer reaction product, there may be additional amplification reactions. Secondary amplification reactions can be used to increase the signal for detection of the target sequence; e.g. by increasing the number of ligated products produced per copy of target. In one embodiment, any number of standard amplification reactions can be performed on the ligation product, including, but not limited to, strand displacement amplification (SDA), nucleic acid sequence based amplification (NASBA), ligation amplification and the polymerase chain reaction (PCR); including a number of variations of PCR, including "quantitative competitive PCR" or "QC-PCR", "arbitrarily primed PCR" or "AP-PCR", "immuno-PCR", "Alu-PCR", "PCR single strand conformational polymorphism" or "PCR-SSCP", "reverse transcriptase PCR" or "RT-PCR", "biotin capture PCR", "vectorette PCR". "panhandle PCR", and "PCR select cDNA subtraction", among others. In one embodiment, the amplification technique is not PCR. According to certain embodiments, one may use ligation techniques such as gap-filling ligation, including, without limitation, gap-filling OLA and LCR, bridging oligonucleotide ligation, FEN-LCR, and correction ligation. Descriptions of these techniques can be found, among other places, in U.S. Pat. No. 5,185,243, published European Patent Applications EP 320308 and EP 439182, published PCT Patent Application WO 90/01069, published PCT Patent Application WO 02/02823, and U.S. patent application Ser. No. 09/898,323.

In addition to standard enzymatic amplification reactions, it is possible to design probe schemes where the ligated product that is initially produced can itself be the target of a secondary chemical ligation reaction.

Furthermore, "preamplification reactions" can be done on starting sample nucleic acids to generate more target sequences for the chemical reaction ligation. For example, whole genome amplification can be done.

As will be appreciated by those skilled in the art, assays utilizing methods and compositions of the invention can take on a wide variety of configurations, depending on the desired application, and can include in situ assays (similar to FISH), solution based assays (e.g. transfer/removal of fluorophores and/or quenchers), and heterogeneous assays (e.g. utilizing solid supports for manipulation, removal and/or detection, such as the use of high density arrays). In addition, assays can include additional reactions, such as pre-amplification of target sequences and secondary amplification reactions after ligation has occurred, as is outlined herein.

Assays pertaining to this aspect of the invention, as described herein, may rely on increases in a signal, e.g. the generation of fluorescence or chemiluminescence. However, as will be appreciated by those in the art, assays that rely on decreases in such signals are also possible.

In one embodiment, assay reactions are performed "in situ" (also referred to in various assay formats as "in vitro" and/or "ex vivo" depending on the sample), similar to FISH reactions. Since no exogenous enzymes need be added, reagents can be added to cells (living, electroporated, fixed, etc.) such as histological samples for the determination of the presence of target sequences, particularly those associated with disease states or other pathologies.

In addition, "in vitro" assays can be done where target sequences are extracted from samples. Samples can be processed (e.g. for paraffin embedded samples, the sample can be prepared), the reagents added and the reaction allowed to proceed, with detection following as is done in the art.

In some embodiments, ligation products (also referred to herein as "ligated products") are detected using solid supports. For example, the ligated products are attached to beads, using either anchor probe/capture probe hybridization or other binding techniques, such as the use of a binding partner pair (e.g. biotin and streptavidin). In one embodiment, a transfer reaction results in a biotin moiety being transferred from the first ligation probe to a second ligation probe comprising a label. Beads comprising streptavidin are contacted with the sample, and the beads are examined for the presence of the label, for example using FACS technologies.

In other embodiments, ligated products are detected using heterogeneous assays. That is, the reaction is done in solution and the product is added to a solid support, such as an array or beads. Generally, one ligation probe comprises an anchor sequence or a binding pair partner (e.g. biotin, haptens, etc.) and the other comprises a label (e.g. a fluorophore, a label probe binding sequence, etc.). The ligated product is added to the solid support, and the support optionally washed. In this embodiment, only the ligated product will be captured and be labeled.

In another aspect of the invention, one of oligonucleotide probes has an attached magnetic bead or some other label (biotin) that allows for easy manipulation of the ligated product. The magnetic bead or label can be attached to either the upstream or the downstream probe using any number of configurations as outlined herein.

As described herein, secondary reactions can also be done, where additional functional moieties (e.g. anchor sequences, primers, labels, etc.) are added. Similarly, secondary amplification reactions can be done as described herein.

Detection systems are known in the art, and include optical assays (including fluorescence and chemiluminescent assays), enzymatic assays, radiolabelling, surface plasmon resonance, magnetoresistance, cantilever deflection, sequencing, surface plasmon resonance, etc. In some embodiments, the ligated product can be used in additional assay technologies, for example, as described in 2006/0068378, hereby incorporated by reference, the ligated product can serve as a linker between light scattering particles such as colloids, resulting in a color change in the presence of the ligated product.

In some embodiments, the detection system can be included within the sample collection tube; for example, blood collection devices can have assays incorporated into the tubes or device to allow detection of pathogens or diseases.

PCT applications WO 95/15971, PCT/US96/09769, PCT/US97/09739, PCT US99/01705, WO96/40712 and WO98/20162, all of which are expressly incorporated herein by reference in their entirety, describe novel compositions comprising nucleic acids containing electron transfer moieties, including electrodes, which allow for novel detection methods of nucleic acid hybridization.

One technology that has gained increased prominence involves the use of DNA arrays (Marshall et al., *Nat. Biotechnol.* (1998) 16(1):27-31), especially for applications involving simultaneous measurement of numerous nucleic acid targets. DNA arrays are most often used for gene expression monitoring where the relative concentration of 1 to 100,000 nucleic acids targets (mRNA) is measured simultaneously. DNA arrays are small devices in which nucleic acid anchor probes are attached to a surface in a pattern that is distinct and known at the time of manufacture (Marshall et al., *Nat. Biotechnol.* (1998) 16(1):27-31) or can be accurately deciphered at a later time such as is the case for bead arrays (Steemers et al., *Nat. Biotechnol.* (2000) 18(1):91-4; and Yang et al., *Genome Res.* (2001) 11(11):1888-98.). After a series of upstream processing steps, the sample of interest is brought into contact with the DNA array, the nucleic acid targets in the sample hybridize to anchor oligonucleotides on the surface, and the identity and often concentration of the target nucleic acids in the sample are determined.

Many of the nucleic acid detection methods in current use have characteristics and/or limitations that hinder their broad applicability. For example, in the case of DNA microarrays, prior to bringing a sample into contact with the microarray, there are usually a series of processing steps that must be performed on the sample. While these steps vary depending upon the manufacturer of the array and/or the technology that is used to read the array (fluorescence, electrochemistry, chemiluminescence, magnetoresistance, cantilever deflection, surface plasmon resonance), these processing steps usually fall into some general categories: Nucleic acid isolation and purification, enzymatic amplification, detectable label incorporation, and clean up post-amplification. Other common steps are sample concentration, amplified target fragmentation so as to reduce the average size of the nucleic acid target, and exonuclease digestion to convert PCR amplified targets to a single stranded species.

The requirement of many upstream processing steps prior to contacting the DNA array with the sample can significantly increase the time and cost of detecting a nucleic acid target(s) by these methods. It can also have significant implications on the quality of the data obtained. For instance, some amplification procedures are very sensitive to target degradation and perform poorly if the input nucleic acid material is not well preserved (Foss et al., *Diagn Mol. Pathol.* (1994) 3(3):148-55). Technologies that can eliminate or reduce the number and/or complexity of the upstream processing steps could significantly reduce the cost and improve the quality of results obtained from a DNA array test. One method for reducing upstream processing steps involves using ligation reactions to increase signal strength and improve specificity.

As outlined above, the assays can be run in a variety of ways. In assays that utilize detection on solid supports, there are a variety of solid supports, including arrays, that find use in the invention.

In some embodiments, solid supports such as beads find use in the present invention. For example, binding partner pairs (one on the ligated product and one on the bead) can be used as outlined above to remove non-ligated reactants. In this embodiment, magnetic beads are particularly preferred.

In some embodiments of the invention, capture probes are attached to solid supports for detection. For example, capture probes can be attached to beads for subsequent analysis using any suitable technique, e.g. FACS. Similarly, bead arrays as described below may be used.

In one embodiment, the present invention provides arrays, each array location comprising at a minimum a covalently attached nucleic acid probe, generally referred to as a "capture probe". By "array" herein is meant a plurality of nucleic acid probes in an array format; the size of the array will depend on the composition and end use of the array. Arrays containing from about 2 different capture ligands to many thousands can be made. Generally, for electrode-based assays, the array will comprise from two to as many as 100,000 or more, depending on the size of the electrodes, as well as the end use of the array. Preferred ranges are from about 2 to about 10,000, with from about 5 to about 1000 being preferred, and from about 10 to about 100 being particularly preferred. In some embodiments, the compositions of the invention may not be in array format; that is, for some embodiments, compositions comprising a single capture probe may be made as well. In addition, in some arrays, multiple substrates may be used, either of different or identical compositions. Thus, for example, large arrays may comprise a plurality of smaller substrates. Nucleic acid arrays are known in the art, and can be classified in a number of ways; both ordered arrays (e.g. the ability to resolve chemistries at discrete sites), and random arrays (e.g. bead arrays) are included. Ordered arrays include, but are not limited to, those made using photolithography techniques (e.g. Affymetrix GeneChip®), spotting techniques (Synteni and others), printing techniques (Hewlett Packard and Rosetta), electrode arrays, three dimensional "gel pad" arrays and liquid arrays.

In a preferred embodiment, the arrays are present on a substrate. By "substrate" or "solid support" or other grammatical equivalents herein is meant any material that can be modified to contain discrete individual sites appropriate for the attachment or association of nucleic acids. The substrate can comprise a wide variety of materials, as will be appreciated by those skilled in the art, including, but not limited to glass, plastics, polymers, metals, metalloids, ceramics, and organics. When the solid support is a bead, a wide variety of substrates are possible, including but not limited to magnetic materials, glass, silicon, dextrans, and plastics.

As will be appreciated, and as is also discussed above, a number of detection methods can be used to detect the presence of and quantify the ligation products (or the amplicons of the ligation products) formed in accordance with the present invention. Such detection methods can be utilized with any of the ligation products (or their amplicons) in any of the assays discussed herein. Such detection methods include without limitation: capillary electrophoresis, mass spectrometry, microarray analysis, sequencing, real-time PCR, optical detection, fluorescence detection, bioluminescence detection, chemiluminescence detection, electrochemical detection, electrochemiluminescence detection and lateral flow detection.

In addition to the above described-assays, specific assays of use in the invention include chemical ligation dependent probe amplification (CLPA) assays, which are discussed in further detail below.

Chemical Ligation Dependent Probe Amplification (CLPA)

In some aspects, the invention relates to chemical ligation dependent probe amplification (CLPA) technology. CLPA is based on the chemical ligation of target specific ligation probes to form a ligation product. This ligation product subsequently serves as a template for an enzymatic amplification reaction to produce amplicons which are subsequently analyzed using any suitable means, including without limitation detection methods such as those discussed above: capillary electrophoresis, mass spectrometry, microarray analysis, sequencing, real-time PCR, optical detection, fluorescence detection, bioluminescence detection, chemiluminescence detection, electrochemical detection, electrochemiluminescence detection and lateral flow detection. CLPA can be used for a variety of purposes including but not limited to analysis of complex gene signature patterns. Unlike other techniques, such as DASL (Bibikova, M., et al., American Journal of Pathology, (2004), 165:5, 1799-1807) and MLPA (Schouten, U.S. Pat. No. 6,955,901), which utilize an enzymatic ligation reaction, CLPA uses a chemical ligation reaction.

In one embodiment, the CLPA assay comprises the use of two or more ligation probes that incorporate reactive moieties that can self-ligate when properly positioned on a target sequence. In a preferred embodiment, a 3'-phosphorothioate moiety on a first probe reacts with a 5'-DABSYL leaving group on a second probe (See Scheme I below).

Scheme 1: Chemical ligation reaction between a 3' phosphorothioate oligonucleotide (S-probe) and a 5' DABSYL modified oligonucleotide (L-probe).

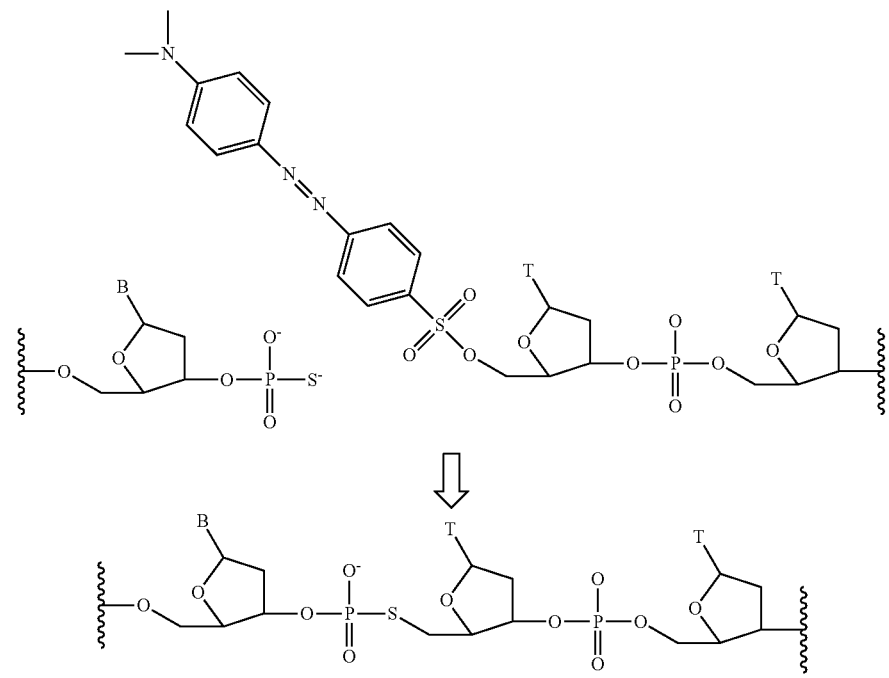

The 5'-DABSYL group reacts about four times faster than other moieties, e.g. iodine, and also simplifies purification of the probes during synthesis.

CLPA has several distinct advantages over other sequence-based hybridization techniques. First, CLPA can be applied directly to RNA analysis without the need to make a DNA copy beforehand. Second, CLPA is relatively insensitive to sample contaminants and can be applied directly to impure samples including body samples such as blood, urine, saliva and feces. Third, CLPA involves fewer steps than other known methods, thereby reducing the time required to gain a result. Moreover, CLPA probes can be stored dry, and properly designed systems will spontaneously react to join two or more oligonucleotides in the presence of a complementary target sequence. Chemical ligation reactions show excellent sequence selectivity and can be used to discriminate single nucleotide polymorphisms.

Significantly, unlike enzymatic ligation methods, CLPA shows nearly identical reactivity on DNA and RNA targets which, as described more fully below, renders CLPA more efficient that other known systems, and expands the scope of applications to which CLPA can be utilized.

Advantageously, the CLPA assay reduces the number of steps required to detect a target nucleic acid, which provides the potential to achieve results in significantly shorter time periods. For example, the general process flow for a standard reverse transcriptase (RT)-multiplex ligase-dependent probe ligation (MLPA) involves the following steps:
1. Isolate total RNA.
2. Use Reverse Transcriptase to make cDNA copy.
3. Hybridize MLPA probe sets to the cDNA target overnight.
4. Add DNA Ligase to join target-bound probes.
5. Amplify ligated probes, e.g. PCR amplification using Taq polymerase and fluorescently labeled PCR primers.
6. Analyze the sample, for example, by CE.

Unlike standard RT-MLPA, CLPA enables analysis to be carried out directly on cell and blood lysates and on RNA targets without a need for steps involving isolating the RNA and performing a reverse transcription reaction to make a cDNA copy prior to ligation. This shortens the time for achieving a result and provides a means to achieve faster analysis.

In further embodiments, CLPA methods of the present invention are conducted on formalin fixed paraffin embedded (FFPE) tissues. In still further embodiments, the FFPE tissues are first subjected to a chemical denaturant to lyse the tissues, and then are subjected to any of the CLPA methods described herein. In yet further embodiments, proteinase K and/or sonication are used to further treat the FFPE tissues prior to application of CLPA methods.

In further embodiments of the invention, faster reaction times are further facilitated by driving the hybridization reaction with higher probe concentrations. Thus, for example, input probe sets may be incorporated in the CLPA reaction at relatively high concentrations, for example, approximately 100-fold higher than those typically used in an MLPA reaction. Elevating the probe concentration significantly reduces the time required for the hybridization step, typically from overnight to between about 15 minutes to about 1 hour.

CLPA probes are generally incorporated in a reaction at a concentration of 250 nanomolar (nM) to 0.01 pM (picomolar) for each probe. Generally, the concentration is between about 1 nM to about 1 pM. Factors to consider when choosing probe concentration include the particular assay and the target being analyzed. The S- or phosphorothioate or Nucleophile probe and L- or leaving group or DABSYL containing probes are incorporated at a concentration that equals or exceeds the concentration of the target. Total concentration of S- and L-probes can reach as high as 10 micromolar (uM). As a non-limiting example, 1 nM for each S and L probe×250 CLPA probe pairs would equal 500 nm (1 nm per probe×2 probes per pair×250 targets) at 10 nM for each probe would mean a total concentration of 5 uM.

The target concentration usually ranges from about 10 micrograms of total RNA to about 10 nanograms, but it can be a little as a single copy of a gene.

When higher probe concentrations are used it is generally preferred to incorporate a purification step prior to amplification, especially for high multiplex analysis (e.g. greater than about 5 targets). In one embodiment of this aspect of this invention, a solid support based capture methodology can be employed including membrane capture, magnetic bead capture and/or particle capture. In a preferred embodiment, a biotin/streptavidin magnetic bead purification protocol is employed after ligation and prior to enzymatic amplification. In some instances, the magnetic particles can be directly added to the amplification master mix without interfering with the subsequent amplification reaction. In other instances, it is preferable to release the captured oligonucleotide from the beads and the released oligonucleotide solution is subsequently amplified without the capture particle or surface being present.

In a preferred embodiment, CLPA involves hybridization of a set of probes to a nucleic acid target sequences such that the probes can undergo self-ligation without addition of a ligase. After a ligation product is produced, amplification is generally used to facilitate detection and analysis of the product. For this purpose, probes are designed to incorporate PCR primers such as, e.g. universal PCR primers. In a preferred embodiment, the universal primers are not added until after the ligation portion of the reaction is complete, and the primers are added after surface capture purification (such as with the use of target capture probes, which are described in further detail herein) along with the polymerase, often as part of a PCR master mix.

The CLPA probes possess reactive moieties positioned such that when the CLPA probes are bound to the nucleic acid target, the reactive moieties are in close spatial orientation and able to undergo a ligation reaction without the addition of ligase enzyme. In a preferred embodiment, the chemical ligation moieties are chosen so as to yield a ligated reaction product that can be efficiently amplified by an amplification enzyme, which is in preferred embodiments a DNA polymerase, but can include other enzymes such as RNA polymerase. Without being bound by theory, chemical ligation chemistries and probe set designs that produce reaction products that more closely resemble substrates that are known as being able to be amplified by DNA and RNA polymerases are more likely to yield efficient probe sets that can be used in the CLPA assay. Especially preferred reaction chemistries are chemical moieties that yield reaction products that closely resemble native DNA such as illustrated in Scheme 1 involving a reaction between a 3'-phosphorothioate and a 5' DABSYL leaving group. In another preferred embodiment, probes sets comprise a 3'-diphosphorothioate (Miller, G. P. et al, Bioorganic and Medicinal Chemistry, (2008) 16:56-64, which is hereby incorporated by reference in its entirety and in particular for all teachings related to probes and 3'-diphosphorothioate chemistries) and a 5'-DABSYL leaving group.

The CLPA probes of the present invention may also incorporate a stuffer sequence (also referred to herein as a variable spacer sequence) to adjust the length of the ligation product. The length of the stuffer sequence can be specific to the target sequence to which the ligation probe is directed, thus providing a convenient means to facilitate analysis of ligation product(s). The stuffer sequence can be located on either or both probes. In embodiments utilizing a 3'-phosphorothioate probe, the stuffer sequence is in preferred embodiments incorporated on this probe (also referred to herein as the "S probe"). As is also discussed above, the stuffer sequence may be located in a region of the ligation probe that is non-complementary to the target nucleic acid, or the stuffer sequence may be located in a region that at least partially overlaps with a region that is complementary to a domain of the target nucleic acid. In further embodiments, the stuffer sequence is located between the primer sequence and the probe domain.

In further embodiments of the invention, CLPA-CE, the stuffer sequence is varied in length in order to produce one or more variable length ligation products which provide the basis for detection and identification of specific target sequences based on length variation. In a preferred embodiment, variable length ligation products are analyzed by capillary electrophoresis (CE). Generally, stuffer sequences are included such that the length of different ligation products varies in a range of at least 1 base pair to about 10 base pairs; preferably from 1 base pair to 4 base pairs. In a preferred embodiment, the length of the different ligation products vary from approximately 80 bp to about 400 bp; preferably in a range of about 100 bp to about 300 bp; more preferably in a range of about 100 bp to about 200 bp. In further embodiments, the stuffer sequences are of a length such that the length of the ligation product is from about 5-1000, 10-950, 15-900, 20-850, 25-800, 30-750, 35-700, 40-650, 50-600, 55-550, 60-500, 65-450, 70-400, 75-350, 80-300, 85-250, 90-200, 95-150 base pairs.

In some embodiments, CLPA probes may further contain other optional element(s) to facilitate analysis and detection of a ligated product. Such elements include any of the elements discussed above in the section on ligation probe pairs. For example, for embodiments referred to herein as CLPA-MDM (and discussed in further detail below), it is preferred that at least one of the ligation probes for incorporate an array binding sequence to bind to an appropriate capture sequence on a microarray platform. For CLPA-MDM, the different CLPA reaction products are not separated by size differences but by the differences in the array binding sequence. In this embodiment, the sequence of the array binding sequence is varied so that each CLPA probe will bind to a unique site on a DNA microarray. The length of the array binding sequence in CLPA-MDM usually varies from 15 to 150 bases, more specifically from 20 to 80 bases, and most specifically from 25 to 50 bases.

In further embodiments, CLPA probes preferably also include other elements to facilitate purification and/or analysis including but not limited to labels such as fluorescent labels and hapten moieties such as, for example, biotin for purifying or detecting ligation product(s). For example, probes and/or ligation product(s) that incorporate biotin can be purified on any suitable avidin/streptavidin platform including beads. While biotin/avidin capture systems are preferred, other hapten systems (e.g. Digoxigenin (DIG) labeling) can be used, as can hybridization/oligonucleotide capture. Hybridization/oligonucleotide capture is a preferred method when it is desirable to release the capture product from the beads at a later stage. In addition to magnetic beads, anti-hapten labeled supports (filter paper, porous filters, surface capture) can be used.

CLPA probe-labeling can be on either probe, either at the end or internally. Preferably biotin is incorporated at the 5' end on the phosphorothioate (S-probe).

Figure 2:
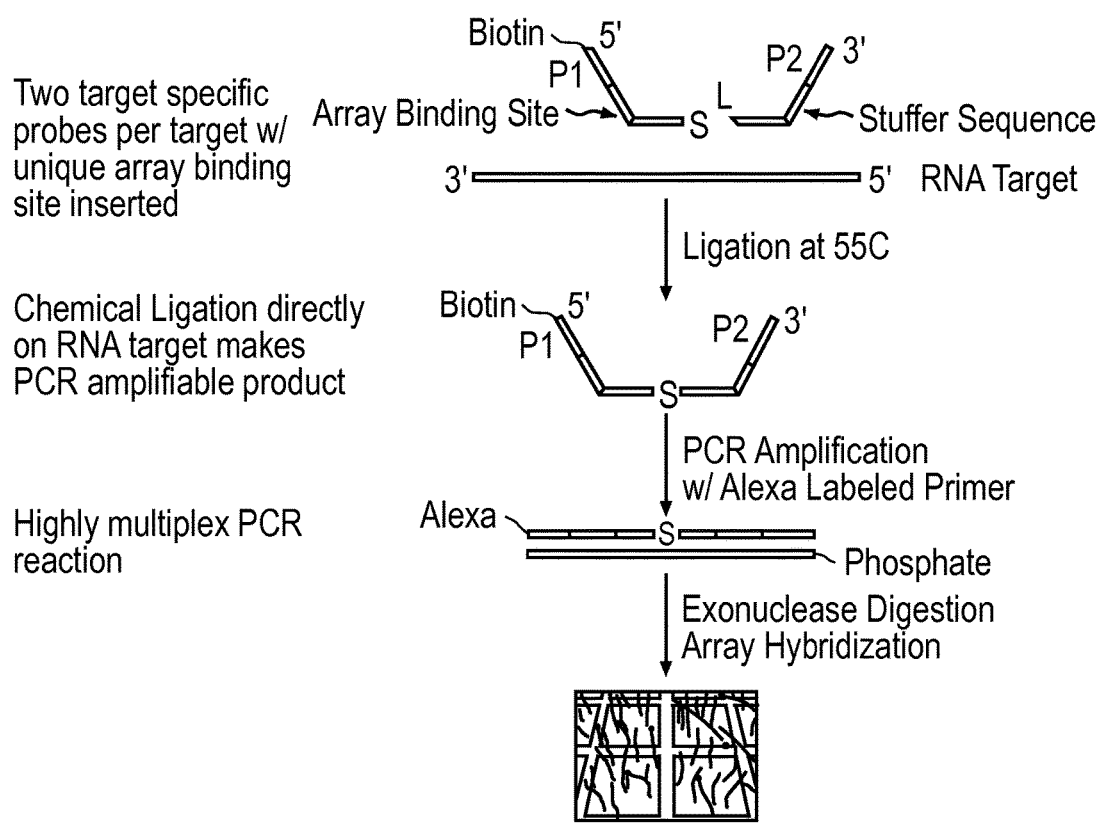
FIG. 2 is a schematic representation of one embodiment of CLPA-MDM assay.

In a preferred embodiment, a CLPA probe set consists of 2 oligonucleotide probes with complementary reactive groups (FIGS. 1 and 2). In another embodiment, the CLPA probe set may consist of 3 or more probes that bind adjacent to each other on a target. In a preferred embodiment of the 3-probe CLPA reaction, the outer probes are designed to contain the enzymatic amplification primer binding sites, and the inner probe is designed to span the region of the target between the other probes. In a more preferred embodiment, the outer probes have non-complementary reactive groups such that they are unable to react with each other in the absence of the internal (middle) probe (FIG. 3). In some instances, both outer probes may have similar reactive moieties except that one group is at the 5' end of one probe and the 3'-end of the other probe, and the L-probe chemistries may also be similar to each other except for positioning on the probe. As is known to one who is skilled in the art, different chemical reagents and processes may be needed to manufacture the probes for the 3-probe CLPA reaction compared to the probes for the 2-probe CLPA system.

Figure 4:
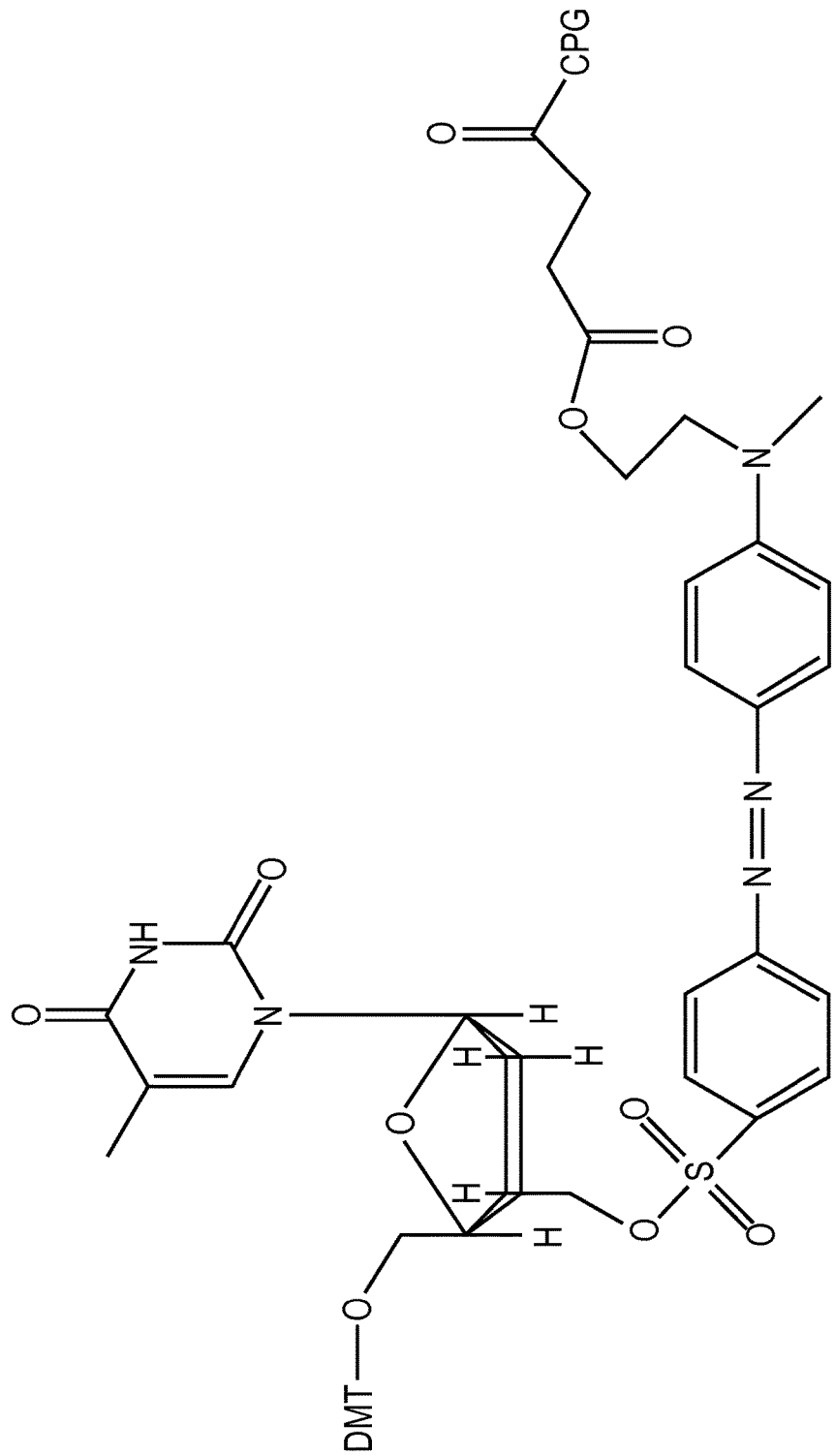
FIG. 4 is a schematic representation of a DNA synthesis resin that can be used to manufacture DNA with a 3'-DABSYL leaving group
Figure 5:
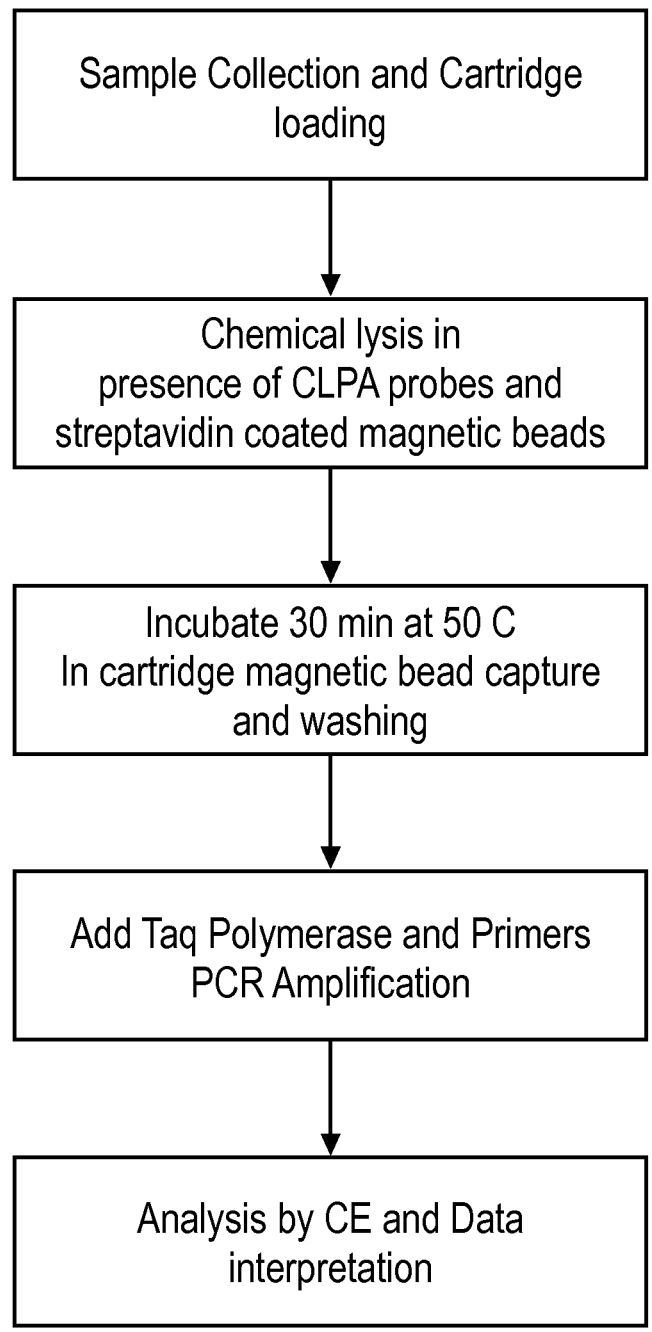
FIG. 5 is a schematic representation on the process flow for one embodiment of the CLPA-CE assay

In a preferred embodiment of the 3-probe CLPA system, one outer probe contains a 3' phosphorothioate (3'S-probe), the other outer probe contains a 5'-phosphorothioate (5'-S-probe) and the center probe contains both a 3'- and a 5'-DABSYL leaving group. The manufacture of a 5'-DABSYL leaving group probes has been reported previously (Sando et al, J. Am. Chem. Soc., (2002), 124(10) 2096-2097). We recently developed a new DNA synthesis reagent that allows for the routine incorporation of a 3'-DABSYL leaving group (see FIG. 4).

In further embodiments and in accordance with any of the CLPA methods described herein, the assays may be conducted in the presence of a buffer of the invention. Such buffers are described in detail above, and any combination of buffer components may be of use in the CLPA methods of the invention. In preferred embodiments, CLPA methods of the invention, including the target capture CLPA, CLPA-CE, and CLPA-MDM methods described below, are conducted in a buffer of the invention, including buffers comprising a denaturant comprising a chaotropic cation such as guanidinium hydrochloride.

Target Capture CLPA

Figure 10:
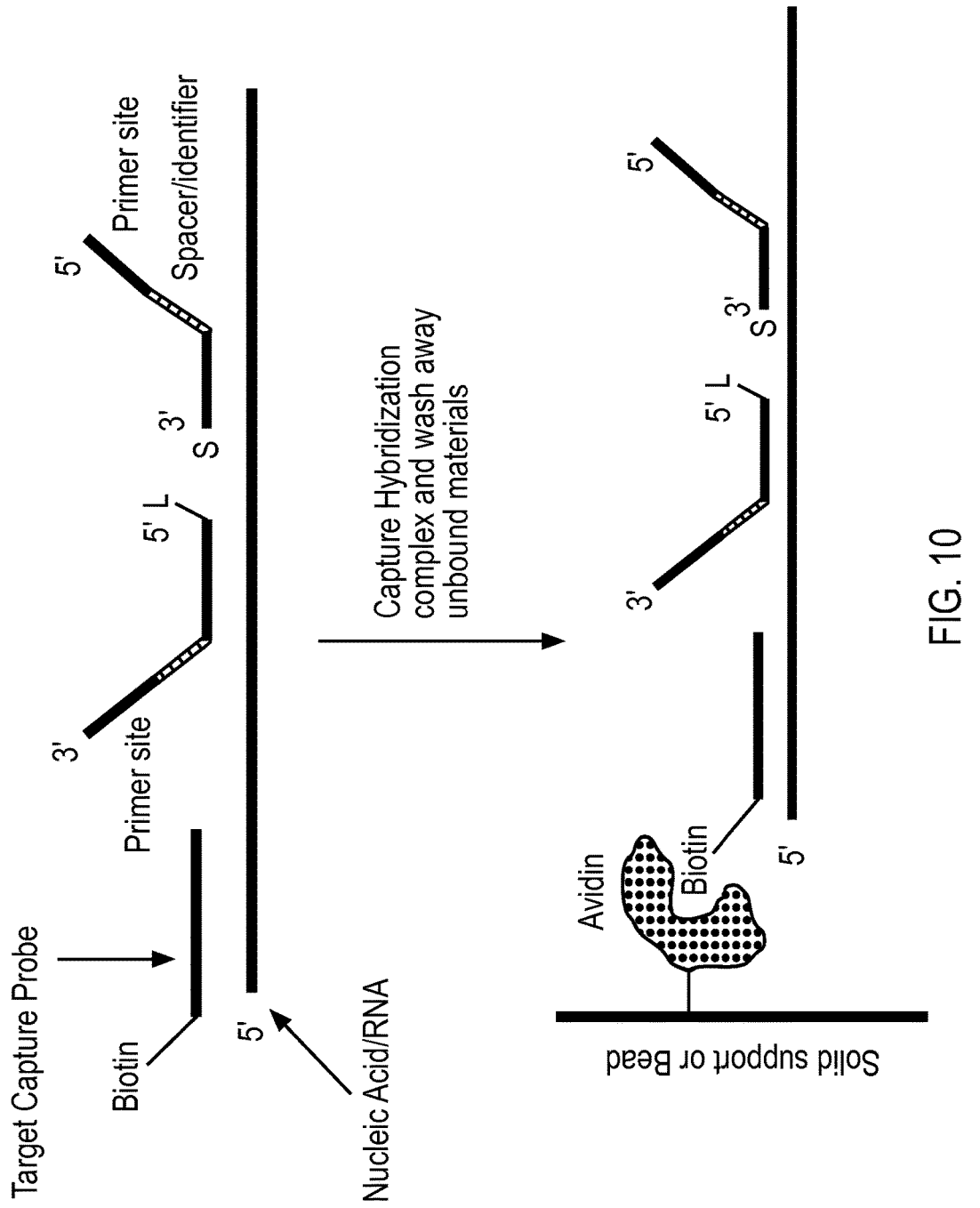
FIG. 10. is a schematic representation of a target capture method used to separate bound CLPA probe sets from solution phase/unbound CLPA probe sets.

In further embodiments, CLPA assays utilizing two or more ligation probes can be combined with a target capture probe that binds upstream or downstream to the CLPA probe set on the same nucleic acid target. This target capture probe contains a capture moiety (which can without limitation include a hapten, a bead, an oligonucleotide capture sequence, and so forth) that can be used to selectively capture complexes/molecules that are bound to the target capture through hybridization or other interactions (FIG. 10).

The target capture probe can be used with any embodiment of CLPA discussed herein.

As is also discussed in further detail above, more than one target capture probe can be applied to a target nucleic acid. These multiple target capture probes can be designed to flank one or more ligation products, either by binding at or near both the 3' and 5' ends of the target nucleic acids or by interleaving the target capture probes between multiple ligation products. As is discussed in further detail below, multiple target capture probes can be used in methods for assessing the quality/integrity of target nucleic acids, particularly RNA.

CLPA-CE

In one aspect, the present invention provides methods for using ligation probes containing variable spacer sequences to produce ligation products, and those ligation products are then detected using capillary electrophoresis.

In certain embodiments, the ligation products are first amplified using any method known in the art (including PCR) to produce amplicons, and it is then the amplicons that are detected using capillary electrophoresis. In further embodiments, the ligation products and/or amplicons are detected by size differentiation capillary electrophoresis (CE) on a sieving matrix, or by slab gel electrophoresis.

A schematic representation for CLPA-CE is provided in FIG. 1. In the embodiment depicted in this figure, a blood sample is subjected to cell lysis by any appropriate means, including without limitation chemical, mechanical or osmotic cell lysis. Preferably, chemical lysis is used.

Following chemical lysis, probes directed to target nucleic acids are applied. FIG. 6 provides a general schematic representation of the design of a probe set for CLPA-CE analysis. In this example, the S probe is designed to include a universal PCR primer for subsequent amplification of ligation product(s). The S probe also includes a stuffer sequence designed with a length that correlates with a specific target sequence. The S probe also includes a target binding sequence (also referred to herein as a "probe domain") that is complementary to a target domain of the target nucleic acid comprising the target sequence to which the stuffer sequence correlates. As will be appreciated, a set of probes may contain a plurality of S probes that are all directed to the same target domain, or the set may contain a mixture of S probes directed to different target domains. Likewise, the L-probe includes a target binding sequence that is complementary to a target domain adjacent to the target domain to which the S probe binds. In this embodiments, the L-probe also includes a universal primer. In further embodiments, one or both of the probes are labeled with a fluorophore (FAM, Cy3, Cy5, etc), however they can also be detected without fluorescence labeling. The labeling is in some embodiments accomplished by using a fluorescently labeled PCR primer.

In the embodiment of CLPA-CE probes pictured in FIG. 6, the S probe also includes a biotin moiety at the 5' end to facilitate purification and removal of unligated probe.

As shown in FIG. 1, after the S- and L-probes are hybridized to the target nucleic acid, the probes undergo a spontaneous chemical ligation to produce a ligation product. In some embodiments in accordance with FIG. 1, a bead purification step is used to remove unligated probes, although the removal of unligated probes is not a required step for all embodiments of CLPA-CE methods. After ligation and the optional removal of unligated probes, the ligation products are amplified. In embodiments in which the ligation probes contain universal primer sequences, universal PCR primer pairs are used to produce amplicons. In embodiments that utilize other types of primer sequences, complementary primer pairs can be used to generate amplicons.

Figure 7:
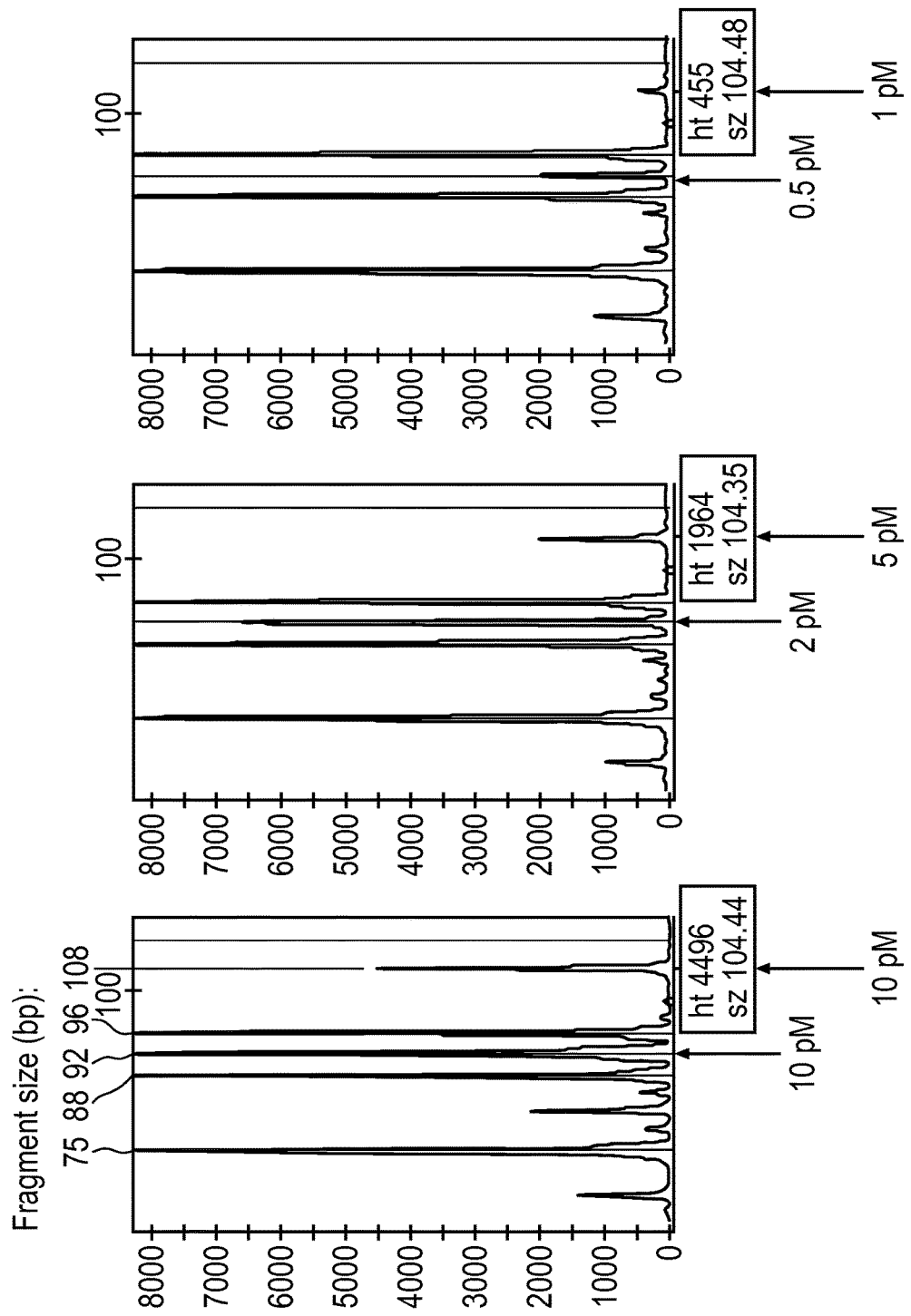
FIG. 7 shows an electrophoretic separation profile on a sample analyzed by CLPA-CE.

Due to the presence of the variable spacer sequence in one (or in some embodiments both) of the ligation probes, the amplicons have a unique length that corresponds to a specific target nucleic acid. Those amplicons are then analyzed using capillary electrophoresis analysis, and the relative intensity of each peak corresponds to relative expression. (FIG. 1 and FIG. 7). In alternative embodiments, other suitable size separation techniques can be used to determine target nucleic acid expression in the sample.

In further embodiments and in accordance with any of the above, the CLPA-CE method includes a step of hybridizing a target capture probe to the target nucleic acid. The resulting target complex comprising the target capture probe, the target nucleic acid and the ligation product is then, prior to amplification of the ligation product, captured on a surface or a substrate through the capture moiety of the target capture probe. In further embodiments, unbound target nucleic acids and ligation probes are removed, leaving only the target complexes and the ligation products. The ligation products can then be amplified and analyzed according to any of the methods described herein. In some embodiments, the ligation products are removed from the target complex prior to amplification using methods known in the art, including heating and the addition of denaturants or other agents to change the hybridization conditions.

CLPA-MDM

In another embodiment of this aspect of the invention, CLPA ligation products are analyzed/detected by microarray analysis (CLPA-MDM). A schematic representation of CLPA-MDM is provided in FIG. 2. CLPA-MDM differs from CLPA-CE in at least the following respects. First, the probe sets differ in design. For example, a general representation of a CLPA-MDM probe set is depicted in FIG. 2. As with CLPA-CE probes, CLPA-MDM probe sets can include universal primers for amplification of ligation product(s). They also include target specific sequences, as well as ligation moieties for enzyme-independent ligation. Additionally, CLPA-MDM probes also may include a stuffer sequence, however the purpose of this stuffer sequence is to adjust the size of the CLPA-MDM to the same length in an effort to standardize enzymatic amplification efficiency. Normalization of amplicon size is not a requirement but can provide advantages for amplification efficiency. A second difference between the design of CLPA-CE and CLPA-MDM probe sets is that the latter include a unique array binding sequence for use with an appropriate microarray platform.

In respect of the CLPA-MDM aspect of the invention, a microarray binding site (ABS sequence) is incorporated into the probe designs for use with a "universal" microarray platform for the detection. Similar to the CLPA-CE system, probes are preferably labeled with a fluorophore, for example by using a fluorescently labeled PCR primer. Alternatively, for example, a sandwich assay labeling technique can be used for the final read-out. Sandwich assays involve designing the probes with a common (generic) label binding site (LBS) in place or in addition to the stuffer sequence and using a secondary probe that will bind to this site during the array hybridization step. This methodology is particularly useful when it is desirable to label the arrays with a chemiluminescent system like a horse radish peroxidase (HRP) labeled oligonucleotide, or with an electrochemical detection system. Generally, planar microarrays are employed (e.g. microarrays spotted on glass slides or circuit board) for the read-out. However, bead microarrays such as those available from Luminex and Illumine can also be used (e.g. Luminex xMAP/xtag).

Nucleic Acid Quality Assessment

In certain aspects, multiple CLPA probe sets that differ in binding position on a nucleic acid target relative to a target capture probe are used (FIG. 11) in methods to assess nucleic acid quality. In the embodiment pictured in FIG. 11, a target capture probe is hybridized to one end of the target nucleic acid, and multiple ligation products produced from different probe sets directed to different target domains of the target nucleic acid are used to produce a target complex comprising the target capture probe and the multiple ligation products.

In such aspects, differences in the signals from the different ligation products provide an assessment of the quality of the nucleic acid target. For example, by measuring the differences in capture efficiency/signal from the unique CLPA probe set located closest to the target capture probe (e.g., 1-100 bp away from the target capture probe) compared to a CLPA probe set further from the target capture probe (e.g., 300-1000 bp away), it is possible to infer the fragmentation or level of degradation of the nucleic acid target. In further exemplary embodiments, the relative ratio of signals generated for the different CLPA probe sets provides a measure of the level of degradation for a particular nucleic acid target. In further embodiments, the ligation probe sets are designed such that they are directed to target domains at known distances from the domain to which the target capture probe is hybridized. In such embodiments, the target complex comprising the target capture probe, the ligation products and the target nucleic acid are captured on a surface or a substrate through a capture moiety on the target capture probe, and unbound target nucleic acids and ligation probes are separated from the captured target complexes. The relative ratio of signals associated with the multiple different probe sets then provides an indication of the amount of degradation present in the target nucleic acids in the sample, and the known distances between the ligation products and the target capture probe provides a kind of "molecular ruler" for quantifying the degradation in the target nucleic acids. For example, in reference to FIG. 11, if in an exemplary embodiment the majority of the target nucleic acids in a sample are degraded in a domain located between the domains to which CLPA set 2 and CLPA set 3 are hybridized, then the signal from CLPA sets 1 and 2 will be relatively larger than the signal from CLPA set 3. This relative ratio between the signals provides an indication of the length and integrity of the target nucleic acids in the sample.

As will be appreciated by those in the art, the spacing of the different probe sets will depend on the size of the original target and the desired information. The spacing can be relatively equidistant (e.g. the use of 3 probe sets spaced roughly 30% of the total length apart), or can be clustered as desired.

In further embodiments, multiple target capture probes are used for assessment of the quality of the nucleic acid target. As is further discussed herein, the different target capture probes can be designed to hybridize near or at the ends of the target nucleic acid and may also or in the alternative be designed to hybridize between different ligation products. In some embodiments, two target capture probes are designed to hybridize to domains both upstream and downstream of one or more ligation products. Use of the two different capture probes can help ensure that even in highly degraded samples, all target complexes comprising ligation products are efficiently captured on a surface or a substrate and separated from unbound target nucleic acids and ligation probes prior to amplification of the ligation products.

Information on degradation is useful in assessing the quality of the nucleic acid and more specifically RNA contained in samples. This technique is particularly useful in assessing the quality of RNA in formalin fixed paraffin embedded (FFPE) tissue samples and other samples where the risk of sample degradation is high.

As discussed above, the difference in capture efficiency can be indirectly determined by measuring the relative ratio of signals. This methodology can be combined with microarray, CE, sequencing, real time PCR and other methods of nucleic acid analysis to further assess the target nucleic acids in accordance with any of the methods described above.

VIII. Hardware

In one aspect of the invention, a fluidic device similar to those described by Liu (2006) is used to automate the methodology described in this invention. See for example U.S. Pat. No. 6,942,771, herein incorporated by reference for components including but not limited to cartridges, devices, pumps, wells, reaction chambers, and detection chambers. The fluidic device may also include zones for capture of magnetic particles, separation filters and resins, including membranes for cell separation (i.e. Leukotrap™ from Pall). The device may include detection chambers for in-cartridge imaging of fluorescence signal generated during Real-Time PCR amplification (i.e. SYBR green, Taqman, Molecular Beacons), as well as capillary electrophoresis channels for on-device separation and detection of reactions products (amplicons and ligation products). In a preferred embodiment, the capillary electrophoresis channel can be molded in a plastic substrate and filled with a sieving polymer matrix (POP-7™ from Applied Biosystems). Channels containing non-sieving matrix can also be used with properly designed probe sets.

In a preferred embodiment, the devices of the invention comprise liquid handling components, including components for loading and unloading fluids at each station or sets of stations. The liquid handling systems can include robotic systems comprising any number of components. In addition, any or all of the steps outlined herein may be automated; thus, for example, the systems may be completely or partially automated.

As will be appreciated by those in the art, there are a wide variety of components which can be used, including, but not limited to, one or more robotic arms; plate handlers for the positioning of microplates; holders with cartridges and/or caps; automated lid or cap handlers to remove and replace lids for wells on non-cross contamination plates; tip assemblies for sample distribution with disposable tips; washable tip assemblies for sample distribution; 96 well loading blocks; cooled reagent racks; microtiter plate pipette positions (optionally cooled); stacking towers for plates and tips; and computer systems.

Fully robotic or microfluidic systems include automated liquid-, particle-, cell- and organism-handling including high throughput pipetting to perform all steps of screening applications. This includes liquid, particle, cell, and organism manipulations such as aspiration, dispensing, mixing, diluting, washing, accurate volumetric transfers; retrieving, and discarding of pipet tips; and repetitive pipetting of identical volumes for multiple deliveries from a single sample aspiration. These manipulations are cross-contamination-free liquid, particle, cell, and organism transfers. This instrument performs automated replication of microplate samples to filters, membranes, and/or daughter plates, high-density transfers, full-plate serial dilutions, and high capacity operation.

In a preferred embodiment, chemically derivatized particles, plates, cartridges, tubes, magnetic particles, or other solid phase matrix with specificity to the assay components are used. The binding surfaces of microplates, tubes or any solid phase matrices include non-polar surfaces, highly polar surfaces, modified dextran coating to promote covalent binding, antibody coating, affinity media to bind fusion proteins or peptides, surface-fixed proteins such as recombinant protein A or G, nucleotide resins or coatings, and other affinity matrix are useful in this invention.

In a preferred embodiment, platforms for multi-well plates, multi-tubes, holders, cartridges, minitubes, deep-well plates, microfuge tubes, cryovials, square well plates, filters, chips, optic fibers, beads, and other solid-phase matrices or platform with various volumes are accommodated on an upgradeable modular platform for additional capacity. This modular platform includes a variable speed orbital shaker, and multi-position work decks for source samples, sample and reagent dilution, assay plates, sample and reagent reservoirs, pipette tips, and an active wash station.

In a preferred embodiment, thermocycler and thermo-regulating systems are used for stabilizing the temperature of heat exchangers such as controlled blocks or platforms to provide accurate temperature control of incubating samples from 0° C. to 100° C.; this is in addition to or in place of the 5 station thermocontrollers.

In a preferred embodiment, interchangeable pipet heads (single or multi-channel) with single or multiple magnetic probes, affinity probes, or pipetters robotically manipulate the liquid, particles, cells, and organisms. Multi-well or multi-tube magnetic separators or platforms manipulate liquid, particles, cells, and organisms in single or multiple sample formats.

In some embodiments, the instrumentation will include a detector, which can be a wide variety of different detectors, depending on the labels and assay. In a preferred embodiment, useful detectors include a microscope(s) with multiple channels of fluorescence; plate readers to provide fluorescent, electrochemical and/or electrical impedance analyzers, ultraviolet and visible spectrophotometric detection with single and dual wavelength endpoint and kinetics capability, fluorescence resonance energy transfer (FRET), luminescence, quenching, two-photon excitation, and intensity redistribution; CCD cameras to capture and transform data and images into quantifiable formats; capillary electrophoresis systems, mass spectrometers and a computer workstation.

These instruments can fit in a sterile laminar flow or fume hood, or are enclosed, self-contained systems, for cell culture growth and transformation in multi-well plates or tubes and for hazardous operations. The living cells may be grown under controlled growth conditions, with controls for temperature, humidity, and gas for time series of the live cell assays. Automated transformation of cells and automated colony pickers may facilitate rapid screening of desired cells.

Flow cytometry or capillary electrophoresis formats can be used for individual capture of magnetic and other beads, particles, cells, and organisms.

The flexible hardware and software allow instrument adaptability for multiple applications. The software program modules allow creation, modification, and running of methods. The system diagnostic modules allow instrument alignment, correct connections, and motor operations. The customized tools, labware, and liquid, particle, cell and organism transfer patterns allow different applications to be performed. The database allows method and parameter storage. Robotic and computer interfaces allow communication between instruments.

In a preferred embodiment, the robotic apparatus includes a central processing unit which communicates with a memory and a set of input/output devices (e.g., keyboard, mouse, monitor, printer, etc.) through a bus. Again, as outlined below, this may be in addition to or in place of the CPU for the multiplexing devices of the invention. The general interaction between a central processing unit, a memory, input/output devices, and a bus is known in the art. Thus, a variety of different procedures, depending on the experiments to be run, are stored in the CPU memory.

These robotic fluid handling systems can utilize any number of different reagents, including buffers, reagents, samples, washes, assay components such as label probes, etc.

IX. Overall Process

One distinct advantage of aspects of the present invention is the ability to collect samples, particularly for RNA detection, into a stabilization buffer that allows both for a) long time periods before testing without sample degradation (of particular use in the assay of RNA, as RNA is degraded extremely rapidly under traditional conditions) and b) the ability to run the assay in the collection buffer without having to do further purification steps to remove components from the mixture that prevent enzymatic assays from being run, such as high denaturing salt concentrations. The ability to collect samples such as blood directly into a buffer that simultaneously lyses the cells and stabilizes the RNA for long periods of time (e.g. days to weeks or longer) allows remote collection and a time lag before assay processing. In addition, these methods thus avoid any special conditions for handling, such as avoidance of heat exposure and/or cold chain handling. For example, samples can be collected and mailed using regular mail and be tested without additional steps.

Furthermore, the ability to assay directly in the collected sample is a significant benefit over the use of sample preparation steps to purify the samples for traditional enzyme based assays.

In further embodiments, a sample is collected into a stabilization buffer in one geographic location and can then be transported to a different geographic location prior to conducting assays on the sample in accordance with any of the aspects and embodiments of the invention discussed herein. In other words, as is discussed above, the present invention provides methods and compositions that result in a stabilized sample that can be collected in one geographic location and then subjected to chemical ligation methods and assays as discussed herein in a different geographic location.

X. Kits

In another aspect of the invention, a kit for the routine detection of a predetermined set of nucleic acid targets is produced that utilizes probes, techniques, methods, and a chemical ligation reaction as described herein as part of the detection process. The kit can comprise probes, target sequences, instructions, buffers, and/or other assay components.

In a further aspect the invention provides for kits for stabilizing and detecting or quantifying RNA in a sample comprising a buffer solution comprising a denaturant, a first ligation probe, and a second ligation probe. In a preferred embodiment, the denaturant is chosen from the group consisting of guanidinium hydrochloride and guanidinium isothiocyanate. In a further preferred embodiment the buffer solution further comprises EDTA, a reducing agent, a surfactant and a pH buffer. In particularly preferred embodiment, the reducing agent is chosen from the group consisting of DTT and mercaptoethanol. In another particularly preferred embodiment, the surfactant is chosen from the group consisting of Triton X-100 and sodium N-lauroylsarcosine.

In still further aspects, the present invention provides kits for detecting a target nucleic acid sequence where that target sequence comprises an adjacent first and second target domain. Such kits may include: a 2× lysis buffer comprising 6 M GuHCl and at least one set of ligation probes, where that at least one set of ligation probes includes a first ligation probe that includes a first probe domain complementary to the first target domain of the target nucleic acid sequence and a second ligation probe that includes a second probe domain complementary to the second target domain of the target nucleic acid sequence. As is further discussed above, the ligation probes included in kits of the invention may include further functionalities, including stuffer sequences, primer sequences, and anchor sequences, and any combination thereof.

EXAMPLES

Example 1: Quantitative Multiplex Detection of Five Targets

Figure 8:
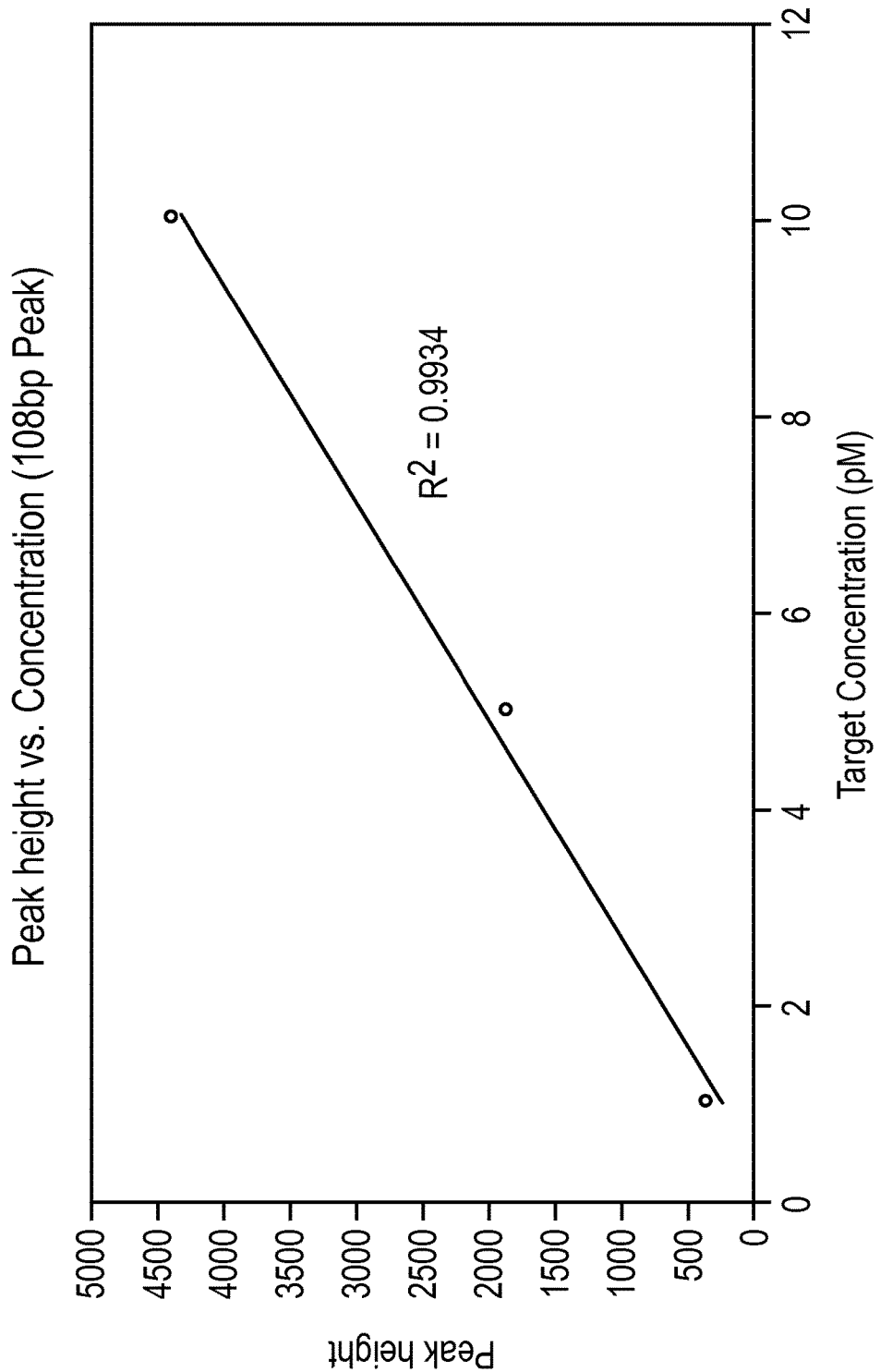
FIG. 8 shows the linear relationship between target concentration and peak height in CLPA-CE analysis.

Multiplex CLPA reactions were performed using five (5) DNA target mimics (corresponding to portions of the MOAP1 (SEQ ID NO:5), PCNA (SEQ ID NO:9), DDB2 (SEQ ID NO:12), BBC3 (SEQ ID NO:16) and BAX (SEQ ID NO:19) genes) combined in one reaction in the presence of their respective CLPA probes (Table 1) (S and L probes at 1 nM each). The target mimics were pooled in different concentration as shown in Table 2. The target mimics, S probes and L probes were incubated in PCR buffer (1×PCR buffer is 1.5 mM MgCL$_2$, 50 mM KCl, 10 mM Tris-HCl pH 8.3) for 1 hour at 50° C. A 1 µl aliquot of each reaction mixture was used as template for PCR amplification using Dynamo SYBR green PCR mix in the presence of Universal Primers (SEQ ID NOS 1 and 2, 300 nM). The samples were PCR cycled for 27 cycles (95° C. 15 min followed by 27 cycles of 95° C. (10 s), 60° C. (24 s), 72° C. (10 s). After PCR amplification, the samples were denatured and injected into an ABI 3130 DNA sequencer (capillary electrophoresis instrument). The CE trace from the ABI for the 3 samples as well as a plot of the peak versus target mimic concentration of PCNA is shown in FIG. 7 and a plot of the linear response of the signal of PCNA as a function on input concentration is shown in FIG. 8.

TABLE 1

Probe and target sequence information.

| SEQ ID | Name | Sequence Detail | Amplicon Size |
|---|---|---|---|
| 1 | Forward PCR Primer | FAM-GGGTTCCCTAAGGGTTGGA | |
| 2 | Reverse PCR Primer | GTGCCAGCAAGATCCAATCTAGA | |
| 3 | MOAP1-L | LTACATCCTTCCTAGTCAATTACACTCTAGATTGGATCTTGCTGGCAC | 47 |
| 4 | MOAP1-S | 5'-Biotin-GGGTTCCCTAAGGGTTGGATAGGTAAATGGCAGTGTAGAACS | 41 |
| | | Ligated MOAP1 Amplicon | 88 |
| 5 | MOAP1-Target mimic | GTGTAATTGACTAGGAAGGATGTAGTTCTACACTGCCATTTACCTA | |
| 6 | MOAP1-RNA Target mimic | GUGUAAUUGACUAGGAAGGAUGUAGUUCUACACUGCCAUUUACCUA | |
| 7 | PCNA-L | LTGGTTTGGTGCTTCAAATACTCTCTAGATTGGATCTTGCTGGCAC | 45 |
| 8 | PCNA-S | Biotin-GGGTTCCCTAAGGGTTGGATCGAGTCTACAGATCCCCAACTTTCATAGTCTGAAACTTTCTCCS | 63 |
| | | Ligated PCNA Amplicon | 108 |
| 9 | PCNA-Target Mimic | AGTATTTGAAGCACCAAACCAGGAGAAAGTTTCAGACTATGA | |
| 10 | DDB2-L | LTAGCAGACACATCCAGGCTCTAGATTGGATCTTGCTGGCAC | 51 |
| 11 | DDB2-S | Biotin-GGGTTCCCTAAGGGTTGGATCGAGTCTACTCCAACTTTGACCACCATTCGGCTACS | 49 |
| | | Ligated DDB2 Amplicon | 96 |
| 12 | DDB2 Target Mimic | GCCTGGATGTGTCTGCTAGTAGCCGAATGGTGGTCA | |
| 13 | DDB2-RNA Target Mimic | GCCUGGAUGUGUCUGCUAGUAGCCGAAUGGUGGUCA | |
| 14 | BBC3-L | LTCCGAGATTTCCCCCTCTAGATTGGATCTTGCTGGCAC | 38 |
| 15 | BBC3-S | Biotin-GGGTTCCCTAAGGGTTGGATCCCAGACTCCTCCCTCTS | 37 |
| | | Ligated BBC3 Amplicon | 75 |
| 16 | BBC3 Target Mimic | GGG GGA AAT CTC GGA AGA GGG AGG AGT CTG GG | |
| 17 | BAX-L | LTCACGGTCTGCCACGCTCTAGATTGGATCTTGCTGGCAC | 39 |
| 18 | BAX-S | Biotin-GGGTTCCCTAAGGGTTGGA TGA GTC TAC ATGA TC CT TCCCGCCACAAAGATGGS | 53 |
| | | Ligated BAX Amplicon | 92 |

TABLE 1 -continued

Probe and target sequence information.

| | | | |
|---|---|---|---|
| 19 | BAX-Target Mimic | CGTGGCAGACCGTGACCATCTTTGTGGCGGGA | |
| 20 | 3-phosphorothioate GAPDH | Biotin-GGGTTCCCTAAGGGTTGGACGGACGCCTGCTTCACCACCTTCTTGATGTCAS | 51 |
| 21 | Middle 2L probe GAPDH | LTCATATTTGGCAGGTTTTTCTAGACGGCAGGTL | 32 |
| 22 | 5'-phosphorothioate GAPDH | SCAGGTCCACCACTGACACGTTGGCAGTTCTAGATTGGATCTTGCTGGCAC | 50 |
| | | Ligated 3-probe amplicon | 133 |
| 23 | ReversePrimer A3632-p | Biotin-ATTAACCCTCACTAAAGGGA | |
| 24 | GAPDH Target Mimic | ACT GCC AAC GTG TCA GTG GTG GAC CTG ACC TGC CGT CTA GAA AAA CCT GCC AAA TAT GAT GAC ATC AAG AAG GTG GTG AAG CAG GCG TC | |
| 25 | GAPDH 3-L | LTTTTCTAGACGGCAGGTCAGGTCCACCAGATGATCGACGAGACACTCTCGCCATCTAGATTGGATCTTGCTGGCAC | |
| 26 | GAPDH 3-S | GGGTTCCCTAAGGGTTGGACGGACCAACTCCTCGCCATATCATCTGTACACCTTCTTGATGTCATCATATTTGGCAGGTS | |
| 27 | GAPDH-3-FAM/BHQ-1 Taqman Probe | (FAM)ccaactcctcgccatatcatctgtacaccttcttg(BHQ-1) | |
| 28 | GAPDH 4-L | LTGCTGATGATCTTGAGGCTGTTGTCATACTGATGATCGACGAGACACTCTCGCCATCTAGATTGGATCTTGCTGGCAC | |
| 29 | GAPDH-4-S | GGGTTCCCTAAGGGTTGGACGATGGAGTTGATGCTGACGGAAGTCATAGTAAGCAGTTGGTGGTGCAGGAGGCATS | |
| 30 | GAPDH-4-QUASAR 670/BHQ-2 Taqman Probe | (Quasar 670)tgctgacggaagtcatagtaagcagttggt(BHQ-2) | |
| 31 | PCNA 2-L | LTCCTTGAGTGCCTCCAACACCTTCTTGAGGATGATCGACGAGACACTCTCGCCATCTAGATTGGATCTTGCTGGCAC | |
| 32 | PCNA 2-S | GGGTTCCCTAAGGGTTGGACGGTACAACAAGACCCAGCTGACGACTCTTAATATCCCAGCAGGCCTCGTTGATGAGGS | |
| 33 | PCNA 2-Cal Fluor Orange 560/BHQ-1 | (CAL Red 610)ctgacgactcttaatatcccagcaggcctcgtt(BHQ-2) | |
| 34 | DDB2-2-L | LTTAGTTCCAAGATAACCTTGGTTCCAGGCTGATGATCGACGAGACACTCTCGCCATCTAGATTGGATCTTGCTGGCAC | |
| 35 | DDB2-2-S | BiotinGGGTTCCCTAAGGGTTGGACGTTAGACGCCAATAGGAGTTTCACTGGTGGCTACCACCCACTGAGAGGAGAAAAGTCATS | |
| 36 | DDB2-2-(CAL Fluor Orange 560/BHQ-1 | (Cal Orange 560)cgccaataggagtttcactggtggctacca(BHQ-2) | |
| 37 | MRPS5-TC | [BIOTIN]GCCAGAGAGGTTACGTGGCGGCTCTCTTCA | 30 |
| 38 | MRPS5-S | GGATGCTATGAGCGATCTGCAGCGTGCAGTCTTCACATCTTCCCAGTCCAGTTTGACGS | 58 |
| 39 | MRPS5-L | LTCTGGAACCTCATCTTCTGGCTCTGGATCCTTCCTAAGTGAATGTTGACAGGATGCTCTAGATTGGATCTTGCTGGCAC | 79 |
| | | Ligated MRPS5 Amplicon | 137 |

TABLE 1 -continued

Probe and target sequence information.

| | | | |
|---|---|---|---|
| 40 | PCNA-TC | [BIOTIN]TCTTCATCCTCGATCTTGGGAGCCAAGTAG | 30 |
| 41 | PCNA-S | GGATGCTATGAGCGATCTGCAGCCACTATACATCTTACTATACTTTACTCTACAACAAGGGGTACATCTGCAGACAS | 76 |
| 42 | PCNA-L | LTACTGAGTGTCACCGTTGAAGAGAGTGGAGTGGCTTTTGTAAAGTCTTCTAGATTGGATCTTGCTGGCAC | 70 |
| | | Ligated PCNA Amplicon | 146 |
| 43 | CDR2-TC | [BIOTIN]AGAGTGATCGGTATTTTGTTCTCTGTTCA | 29 |
| 44 | CDR2-S | GGATGCTATGAGCGATCTGCAGCGCAATTCATTTCATTCACAATCAATCTAAAGATCTCCTTAAACAACGCTTTGTATTCTGGAGGS | 86 |
| 45 | CDR2-L | LTGTTGTAGGGGAACTCACGGGCTCTGGGTTGACAGAGGCCAGTTAGGATGTTACCACCAGTGAATGTTGACAGGATCCTCTAGATTGGATCTTGCTGGCAC | 101 |
| | | Ligated CDR2 Amplicon | 187 |

| | | | *Luminex Bead # |
|---|---|---|---|
| 46 | GAPDH-L | LTCCATTGATGACAAGCTTCCCGTTCTCAGCTCGCGTTCTAAGCTTCCCTTTAGTGAGGGTTAAT | |
| 47 | GAPDH-S | Biotin-TAATACGACTCACTATAGGGCGAGTAGAAAGTTGAAATTGATTATGATCTCGCTCCTGGAAGATGGTGATGGGATTS | 12 |
| 48 | ACTG2-L | LTTCTCCCAGTGACTGAGGGCTGGTGTGTCTTTGGCTCCCTTTAGTGAGGGTTAAT | |
| 49 | ACTG2-S | Biotin-TAATACGACTCACTATAGGGCGAATTGAGAAAGAGATAAATGATAGGGACTGGAGCACCGAGGGTATGAGAGGTTCS | 72 |
| 50 | ACPP-L | LTTCAACTCCTTGGCTAGTACACTTCGGTCTAGCGCTCCCTTTAGTGAGGGTTAAT | |
| 51 | ACPP-S | Biotin-TAATACGACTCACTATAGGGCGGTAAGAGTATTGAAATTAGTAAGAGGTCTCCATGCCGAAACACCAAAGTCACAAACS | 66 |
| 52 | RDH11-L | LTGTGCATCTCAAAGCCATCTGCTGTCTTCGGCTCCCTTTAGTGAGGGTTAAT | |
| 53 | RDH11-S | Biotin-TAATACGACTCACTATAGGGCGTTTGTTGTTAAGTATGTGATTTAGGGAGGAAGTGACCCAAGTGGTTGACTCCTAS | 63 |
| 54 | DES-L | LTGTTCTCTGCTTCTTCCTTCAACTGAATCTCCTCCTGCTTCCCTTTAGTGAGGGTTAAT | |
| 55 | DES-S | Biotin-TAATACGACTCACTATAGGGTATTTGATAAGAGAATGAAGAAGTATCCACGTCCGCTCGGAAGGCAGCCAAATS | 68 |
| 56 | Primer A3534-p | p-TAATACGACTCACTATAGGG | |

*Luminex Product Insert Sheet MagTAG-Plex Microspheres.
L = DABSYL ligation moiety
S = phosphorothioate moiety

TABLE 2

Sample Concentrations

| Sample | Target Mimic Concentrations |
|---|---|
| 1 | All Target mimics at 10 pM final Concentration |
| 2 | MOAP1, DDB2 and BBC3 at 10 pM, PCNA at 5 pM and BAX at 2 pM |
| 3 | MOAP1, DDB2 and BBC3 at 10 pM, PCNA at 1 pM and BAX at 0.5 pM |

Example 2: CLPA Reactions Using MOAP1 and DDB2 DNA and RNA Target Mimics

Reactions were prepared in duplicate as presented in Table 3 using DNA or RNA target mimics for the MOAP1 and DDB2 genes and CLPA probes sets designed to target the sequences. The probe numbers refer to the SEQ ID NOs in Table 1. The reagents were added in the concentrations and volumes shown in Table 4. The respective S-probe, L-probe and target mimic were heated to 50° C. for 60 minutes in a 0.2 mL PCR tube, after which 2.5 µl of the CLPA reaction was used as template in a real-time PCR reaction with 40 amplification cycles. Real-time PCR data was averaged for the duplicate samples and is presented in Table 3 (Ct value column). Minimal differences in Ct value between RNA and DNA target mimics were observed indicating similar probe ligation efficiency on RNA and DNA substrates.

TABLE 3

CLPA Probe Sets.

| Sample | Identifier | L-Probe (1 nM) SEQ ID NO | S-Probe (1 nM) SEQ ID NO | Target Mimic (10 pM) SEQ ID NO | Ct value |
|---|---|---|---|---|---|
| 1 | MOAP-1 DNA | 3 | 4 | 5 | 19.5 |
| 2 | MOAP-1 RNA | 3 | 4 | 6 | 20 |
| 3 | DDB2 DNA | 10 | 11 | 12 | 21 |
| 4 | DDB2 RNA | 10 | 11 | 13 | 21 |

TABLE 4

Reagent table-Example 1

| | |
|---|---|
| 1X PCR Buffer Buffer* | 12.5 ul |
| S-Probe (1 nM) & L-Probe (1 nM) | 2.5 ul each |
| Target Mimic (100 pM) | 2.5 ul |
| Water | 5.0 ul |
| Heat at 50 C. for 1 hour | |

*1X PCR buffer is 1.5 mM MgCL2, 50 mM KCl, 10 mM Tris-HCl pH 8.3

Example 3: Direct Analysis of DDB2 RNA Transcripts in Lysis Buffer and Lysed Blood DDB2 messenger RNA (mRNA) was prepared using an in-vitro transcription kit from Ambion and a cDNA vector plasmid from Origene (SC122547). The concentration of mRNA was determined using PicoGreen RNA assay kit from Invitrogen. The DDB2 probe sets (Table 5) were tested with different concentrations of DDB2 mRNA transcript spiked into either water or whole blood. The reactions mixture components are listed in Table 5. Samples 1-4 consisted of DDB2 transcript at 10 ng, 1 ng, 0.1 ng and 0.01 ng in water, and samples 5-8 consisted of the same concentration range spiked into whole blood. Similar reactions protocols were followed with the exception of adding Proteinase K to the blood samples so as to reduce protein coagulation. The procedure is as follows: The reagents were added in the concentrations and volumes in Table 5 and Table 6.

The RNA transcripts were stable once combined with the buffer prior to the subsequent heat step and could be stored in this buffer solution for several days without observing any significant degradation of the RNA. The S-probes, mRNA transcript, Guanidine hydrochloride lysis buffer and either water (samples 1-4) or whole blood (samples 5-8) were heated to 80° C. for 5 minutes and then they were moved to a 55° C. heat block. The L-probe, wash buffer, streptavidin beads and proteinase K were added, and the reaction was incubated at 55° C. for 60 minutes. The samples were removed from the heat block and the magnetic beads were captured using a dynal MPC 96S magnetic capture plate. The supernatant was removed and the beads were washed 3 times with wash buffer. DyNamo SYBR green PCR master mix (25 ul, 1×) and universal primers (SEQ ID NOS 1 and 2, 300 nM) were added to the beads and samples were heat cycled using a Stratagene MX4000 realtime PCR instrument for 30 cycles (95° C. for 15 minutes, 30 cycles 95° C. (10 s), 60° C. (24 s), 72° C. (10 s)). The Ct values were recorded and the amplified samples were injected into an Agilent Bioanalyzer 2100 so as to verify the length of the amplicons. All amplicons showed the correct size (~96 bp) and the performance was comparable for the blood and water samples demonstrating the ability to directly analyze RNA in lysed blood. The results are summarizes in Table 7 below. In additional experiments it was shown that the length of time (from a few minutes to several hours and even up to several days) that the RNA transcripts were stored in the buffer solution prior to the initial heat step did not significantly alter the results summarized in Table 7.

TABLE 5

CLPA Probe Sets.

| Sample | Identifier | L-Probe (1 nM) | S-Probe (1 nM) | RNA Transcript |
|---|---|---|---|---|
| 1-8 | DDB2 | SEQ ID NO: 10 | SEQ ID NO: 11 | Origene Plasmid SC122547 |

TABLE 6

DDB2 reaction mixture.

| Samples | 1-4 | 5-8 |
|---|---|---|
| GuHCL Lysis Buffer (2X) | 12.5 µl | 12.5 µl |
| S-Probe (5 nM) | 1 µl | 1 µl |

TABLE 6-continued

DDB2 reaction mixture.

| Samples | 1-4 | 5-8 |
|---|---|---|
| RNA Transcript (10 ng/ul to 0.01 ng/ul) | 1 µl | 1 µl |
| Whole Blood | 0 µl | 12.5 µl |
| Water | 12.5 ul | 0 µl |
| Heat 80° C. for 5 min, chill on ice | | |
| Wash Buffer | 20 µl | 15 µl |
| L-Probe (5 nM) | 1 µl | 1 µl |
| Dynal M-270 Beads | 2 µl | 2 µl |
| Proteinase K (10 mg/ml) | 0 µl | 5 µl |
| Total | 50 µl | 50 µl |
| Incubate 55° C. for 60 min. | | | a) GuHCL lysis buffer (1X) is 3M GUHCL, 20 mM EDTA, 5 mM DTT, 1.5% Triton, 30 mM Tris pH 7.2).
b) Wash Buffer is 100 mM Tris (pH 7.4), 0.01% Triton.

TABLE 7

Summary results of water versus blood

| Assay | DDB2 Conc | Ct value | Sample |
|---|---|---|---|
| 1 | 10 ng | 13.5 | Water |
| 2 | 1 ng | 17 | Water |
| 3 | 0.1 ng | 20.2 | Water |
| 4 | 0.01 ng | 24 | Water |
| 5 | 10 ng | 13.5 | Blood |
| 6 | 1 ng | 16 | Blood |
| 7 | 0.1 ng | 19.2 | Blood |
| 8 | 0.01 ng | 23.5 | Blood |

Example 4: 3-Probe CLPA-CE Assay

Reactions were prepared in duplicate as presented in Table 8 using DNA target mimic probe SEQ ID NO 24 and the 3-probe CLPA probe set (SEQ ID NOS 20, 21 and 22). The probe numbers refer to the SEQ ID NOS in Table 1. The reagents were added in the concentrations and volumes in Table 9. The S-probes, L-probe and target mimics were immediately heated to 50° C. for 60 minutes in a 0.2 mL PCR tube, after which 2.5 µl of the CLPA reaction was used as template in a Dynamo SYBR green PCR reaction with 25 amplification cycles. Real-time PCR data was averaged for the duplicate samples and is presented in Table 8 (Ct value column). A 1 µl sample of each reaction was then analyzed via Agilent Bioanalyzer 2100 to determine the size of the reaction product.

TABLE 8

CLPA Probe Sets.

| Samples | Identifier | 3'-S probe SEQ ID NO | 2L-Probe SEQ ID NO | 5'-S Probe SEQ ID NO | Target Mimic SEQ ID NO | Amplicon size | Ct value |
|---|---|---|---|---|---|---|---|
| 1&2 | GAPDH | 20 | 21 | 22 | 24 | About 135 bp | 16.3 |
| 3&4 | Negative | 20 | 21 | 22 | 24 | None observed | No CT |

Probes at 1 nM concentration; target mimic at 10 pM concentration.

TABLE 9

Reagent table-Example 4

| | |
|---|---|
| 1X PCR Buffer Buffer* | 12.5 µl |
| 3 and 5' S-Probe (10 nM) & 2L-Probe (10 nM) | 2.5 µl each |
| Target Mimic (1 nM) | 2.5 µl |
| Water | 2.5 µl |
| Heat at 50° C. for 1 hour | |

*1X PCR buffer is 1.5 mM MgCL2, 50 mM KCl, 10 mM Tris-HCl pH 8.3

Example 5: Multiplex Real-Time CLPA Detection of mRNA

In a 0.2 ml PCR tube were added 4 sets of CLPA reagents that were engineered to possess unique binding sites for different color dual labeled probes. The reactions were prepared as indicated in Table 10 and Table 11. The CLPA probes sets and dual labeled probes correspond to SEQ ID NOS 25 through 36 in Table 1. The S and run-off transcript mRNA (GAPDH, PCNA and DDB2) were added to 2× lysis buffer (GuHCL lysis buffer (1×) is 3M GUHCL, 20 mM EDTA, 5 mM DTT, 1.5% Triton, 30 mM Tris pH 7.2). The mRNA transcripts were stable once combined with the buffer prior to the subsequent heat step and could be stored in this buffer solution for several days without observing any significant degradation of the RNA. The solution was then heated to 80° C. for 5 min. The samples were cooled on ice and streptavidin coated magnetic beads (DYNAL M-270) and L-probe were added. The samples were heated at 50° C. for 1 hour. The magnetic beads were captured on a DYNAL MPC plate and washed twice with wash buffer. The beads were recaptured and dynamo PCR 1× mastermix was added with the 4 different dual labeled probes and universal PCR primers (25 ul total volume). The samples were heat cycled using a Stratagene MX4000 realtime PCR instrument for 30 cycles (95° C. for 15 minutes, 30 cycles 95° C. (10 s), 60° C. (24 s), 72° C. (10 s)) with proper filters for monitoring the fluorescence in the FAM, Cal Fluor orange 560, Cal Fluor Red 610, and Quasar 670 channels. The Ct values observed for each channel were recorded and are indicated in Table 10.

TABLE 10

Multiplex reagents used in Example 5.

| Samples | S Probes (25 pM) SEQ ID NOs | L Probes (25 pM) SEQ ID NOs | Targets | Ct(FAM)-GAPDH3 | Ct(560)-DDB2 | Ct(610)-PCNA | Ct(670)-GAPDH4 |
|---|---|---|---|---|---|---|---|
| 1 & 2 | 26, 29, 32, 35 | 25, 28 31, 34 | 250 ng yeast tRNA; 40 pg GAPDH(Origene SC118869), 40 pg PCNA (SC118528), 40 pg DDB2 (SC122547) mRNA | 25.5 | 24.5 | 24.8 | 25.8 |
| 3 & 4 | 26, 29, 32, 35 | 25, 28 31, 34 | 250 ng yeast tRNA (negative) | No Ct | No Ct | No Ct | No Ct |
| 5 & 6 | 26, 29, 32, 35 | 25, 28 31, 34 | 250 ng yeast tRNA; 40 pg GAPDH(Origene SC118869), 40 pg PCNA (SC118528), 40 pg DDB2 (SC122547) mRNA | 22.1 | 24.5 | 22.1 | 22.2 |
| 7 & 8 | 26, 29, 32, 35 | 25, 28 31, 34 | 250 ng yeast tRNA (negative) | No Ct | No Ct | No Ct | No Ct |

TABLE 11

Additional reagents used in Example 5.

| | |
|---|---|
| GuHCL Lysis Buffer (2X) | 12.5 μl |
| S-Probes (0.25 nM Stock of each) | 5 μl |
| mRNAs (250 ng tRNA +/− mRNAs) | 5 μl |
| Water | 2.5 μl |
| Heat 80° C. for 5 min, chill on ice | |
| Water | 18 μl |
| L-Probes (0.25 nm stock of each) | 5 μl |
| Beads | 2 μl |
| Total | 50 μl |
| Incubate 50° C. 1 Hour | |

Example 6: Formalin-Fixed, Paraffin-Embedded (FFPE) CLPA Assay

Figure 9:
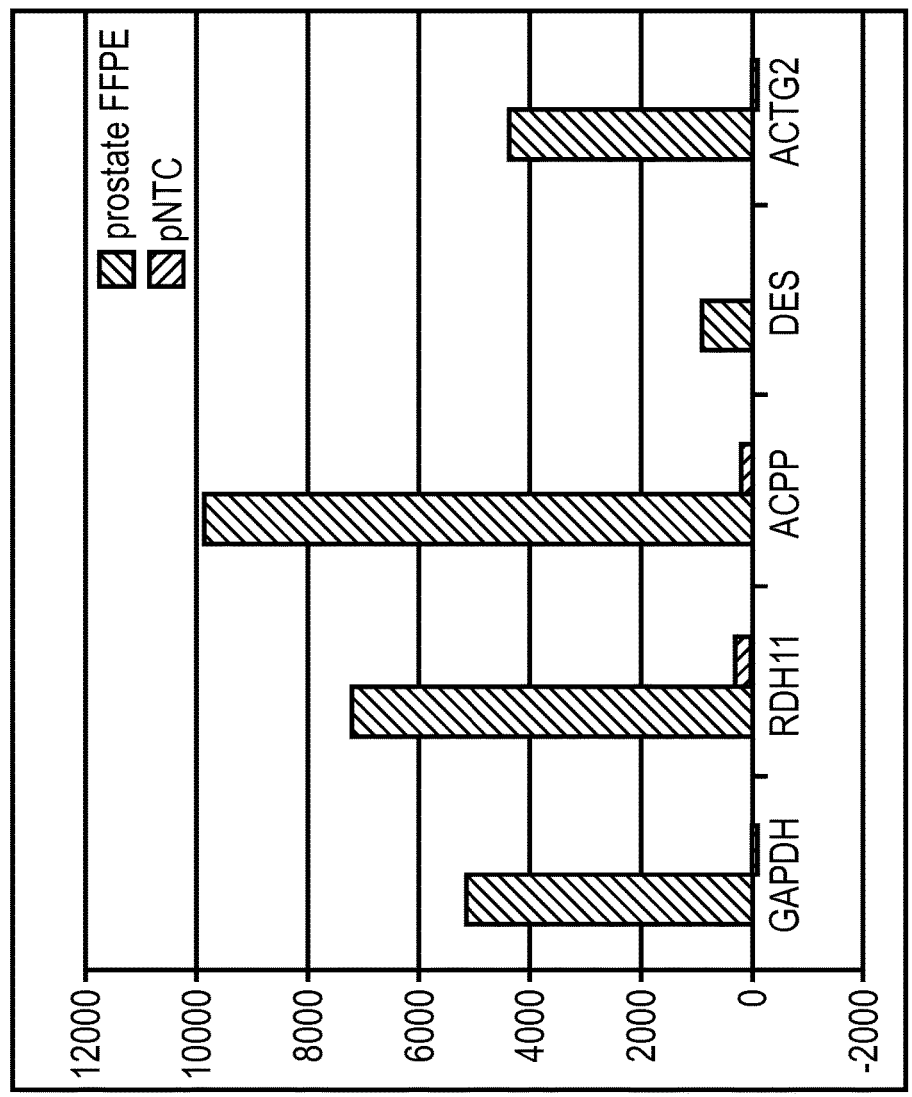
FIG. 9 shows data for an analysis of FFPE tissue samples comparing a Luminex Signal for various targets with a slice of prostate FFPE tissue (left hand bar for each target) and the no target control (pNTC—right hand bar for each target).

Protocol:
1. 25 ul CLPA Lysis Buffer (6M GuHCl, 40 mM EDTA, 10 mM DTT, 3% Triton X-100, 100 mM Tris pH 7.5) containing 400 pM of each S probe (Sequence IDs 47, 49, 51, 53, and 55) and 25 ul of TE buffer were added to a 200 ul PCR tube.
2. Formalin-Fixed, Paraffin-Embedded (FFPE) tissue blocks were sectioned using a microtome blade (Leica, RM 2155) to a thickness of 5 microns and fixed on pathology glass slides. FFPE sample with an approximate size of 2 mm×5 mm×5 microns were scraped off the glass slide and added to PCR tubes.
3. The PCR tube containing the FFPE sample and lysis buffer is sonicated at 50 Hz in a water bath sonicator (Branson Ultrasonics) for 5 minutes at 55° C.
4. The tube is removed from the sonication bath and 40 ul of Proteinase K solution (2.5 mg/ml) and 10 ul of L-probe solution (1 nM in each probe, Seq. ID 46, 48, 50, 52, and 54) were added with mixing.
5. The tubes were incubated at 55° C. for 3 hours.
6. The samples were removed from the heat block, and the samples were centrifuged for 1 min at 3000 rpm using a benchtop swing-rotor centrifuge.
7. Only the supernatant were transferred to a fresh PCR tube.
8. 2.0 ul on Invitrogen/Dynal M-270 streptavidin coated magnetic beads were added, mixed and the samples were incubated for 5 minutes.
9. The beads were captured using a Dynal MPC 96-S magnetic plate and the supernatant was removed.
10. The beads were washed 2 times with 200 ul of wash buffer (100 mM tris buffer, pH 7.0)
11. The final wash was discarded and the beads were resuspended in 10 ul of Dynamo F-450 Taq polymerase master mix (Finnzymes) and 10 ul of PCR primer set (600 nM each of sequence ID 56 and 23).
12. The samples were then thermally cycled according to the protocol: 95° C. 10 min ramp; 28 cycle PCR: 94° C. for 10 seconds; 60° C. for 20 seconds; 72° C. for 20 seconds.
13. At the thermal cycling was complete, 1 ul Exonuclease was added to each PCR reaction tube and the samples were incubated for 20 min at 37° C. followed by 95 C for 2 min.
14. 2.5 ul of PCR reaction was removed from each well and added to 22.5 ul of Luminex Bead Mix. The Luminex Bead Mix was prepared as follows. Combine 2500 microspheres for each set per reaction (Beads 66, 63, 68, 12 and 72). Dilute/concentrate the MagPlex-TAG microsphere mixture to 111 of each microsphere set per uL in 1.1× Tm Hybridization Buffer by vortex and sonication for approximately 20 seconds.
15. The samples are then incubated at 95° C. for 1.5 min and then 37° C. for 1 hour with agitation using a Thermomixer.
16. Prepare Reporter Mix by diluting SAPE to 10 ug/mL in 1× Tm Buffer (0.2M NaCl, 0.1 M Tris, 0.08% Triton X-100, pH 8.0).
17. Add 100 ul Reporter Mix to each well. Mix gently.
18. Incubate at 37° C. for 15 minutes.
19. The MagTag assay was then run on the Luminex instrument according to manufacturer's protocols The results are shown in FIG. 9.

Example 7: Target Capture CLPA Blood Assay

In a 0.2 ml PCR tube, 25 ul of whole blood was mixed with 25 ul of 2× GuHCl Lysis buffer. The sample was vortexed briefly. To this tube was added 25 ul of a solution containing 2.0 nM target capture probes (TC) and 2.0 nM S-probe probes. The solution was mixed and heated to 80° C. for 5 min and then cooled to 55° C. While at 55° C., 50 ul of a solution containing 1.0 nM L-probes and 2 mg/ml of proteinase K were added. The S-probe, L-probe and TC probe sequences are listed in Table 1, Sequence ID 37-45.

The solution was mixed and heated to 55° C. for 30 minutes. After 30 minutes, 2 ul of M-270 streptavidin coated magnetic beads were added. The samples were mixed by gentle pipetting followed by incubation for 5 minutes longer at 55° C. The samples were removed from the heat blood and immediately placed onto a 96-well magnetic concentrator plate (Dynal). After 15 seconds, the supernatant was removed completely. The beads were washed 3 times with 180 ul of wash buffer (100 mM tris buffer, pH 7.4, 0.01% triton). The was buffer was removed and the PCR mix containing 300 nM each of primer 1 and 2 were added. The samples were thermal cycled for 28 cycles (95° C. 2 min, 28 cycles 94° C. (10 s), 60 C (20 s) and 72° C. (20 S)). After thermal cycling, the 2.0 ul of PCR product was mixed with 1 ul of ABI Genescan 600 V2 size standard and 17 ul of formamide. The samples were heated to 95° C. for 5 minutes and then placed on an ABI 3500 Capillary electrophoresis instrument for analysis. Only 3 peaks were observed within the range of 110-200 base pairs on the CE trace.

TABLE 13

Example 7 results

| Gene | Size | Peak Height (RFU) |
|---|---|---|
| MRPS5 | 137 | 30000 |
| PCNA | 146 | 28000 |
| CDR2 | 187 | 4000 |

The present specification provides a complete description of the methodologies, systems and/or structures and uses thereof in example aspects of the presently-described technology. Although various aspects of this technology have been described above with a certain degree of particularity, or with reference to one or more individual aspects, those skilled in the art could make numerous alterations to the disclosed aspects without departing from the spirit or scope of the technology hereof. Since many aspects can be made without departing from the spirit and scope of the presently described technology, the appropriate scope resides in the claims hereinafter appended. Other aspects are therefore contemplated. Furthermore, it should be understood that any operations may be performed in any order, unless explicitly claimed otherwise or a specific order is inherently necessitated by the claim language. It is intended that all matter contained in the above description and shown in the accompanying drawings shall be interpreted as illustrative only of particular aspects and are not limiting to the embodiments shown. Unless otherwise clear from the context or expressly stated, any concentration values provided herein are generally given in terms of admixture values or percentages without regard to any conversion that occurs upon or following addition of the particular component of the mixture. To the extent not already expressly incorporated herein, all published references and patent documents referred to in this disclosure are incorporated herein by reference in their entirety for all purposes. Changes in detail or structure may be made without departing from the basic elements of the present technology as defined in the following claims.

What is claimed is:

1. A method for detecting a plurality of different target nucleic acids in a sample, wherein each target nucleic acid comprises a first target domain adjacent to a second target domain and a third target capture domain located upstream or downstream from said first and second target domains, said method comprising:
   (a) providing a plurality of ligation substrates each comprising:
      (i) one of said target nucleic acids;
      (ii) a first set of ligation probes comprising:
         (A) a first nucleic acid ligation probe comprising:
            (1) a first probe domain hybridized to a first target domain of said one target nucleic acid sequence;
            (2) a 5'-ligation moiety; and
         (B) a second nucleic acid ligation probe comprising:
            (1) a second probe domain hybridized to a second target domain of said one target nucleic acid sequence; and
            (2) a 3' ligation moiety;
   (b) ligating said first and second ligation probes without the use of a ligase enzyme to form a first plurality of ligation products;
   (c) hybridizing target capture probes comprising a capture moiety to said third target domain of said target nucleic acids to form target complexes;
   (d) capturing said target complexes on a surface using said capture moiety;
   (e) amplifying said ligation products to form amplicons;
   (f) detecting said amplicons,
   thereby detecting said target nucleic acids.

2. The method of claim 1, wherein:
   said target nucleic acids further comprise a fourth target domain adjacent to a fifth target domain;
   said plurality of ligation substrates each further comprises a second set of ligation probes comprising a third nucleic acid ligation probe hybridized to said fourth target domain and a fourth nucleic acid ligation probe hybridized to said fifth target domain;
   said method further comprising ligating said third and fourth ligation probes in the absence of a ligase enzyme such that said one target nucleic acid sequence comprises multiple ligation products;
   and said detecting step (f) comprises detecting amplicons generated from said multiple ligation products.

3. The method of claim 2, wherein said target nucleic acids further comprise a sixth target domain adjacent to a seventh target domain;
   said plurality of ligation substrates each further comprises a third set of ligation probes comprising a fifth nucleic acid ligation probe hybridized to said sixth target domain and a sixth nucleic acid ligation probe hybridized to said seventh target domain;
   said method further comprising ligating said third and fourth ligation probes in the absence of a ligase enzyme such that said one target nucleic acid sequence comprises multiple ligation products.

4. The method of claim 1, wherein each of said ligation probes further comprises a primer sequence.

5. The method of claim 1, wherein at least one of said ligation probes of each set of ligation probes further comprise a variable spacer sequence such that said amplicons have a target specific length.

6. The method of claim 1, wherein only one ligation probe of each set of ligation probes comprises said variable spacer sequence.

7. The method of claim 5, wherein said variable spacer sequence is contained between said probe domain and said primer of said ligation probe.

8. The method of claim 1, wherein said capture moiety of said target capture probe comprises a member selected from: a capture nucleic acid sequence, a bead and a binding partner of a binding partner pair.

9. The method of claim 1, wherein said 5' ligation moiety comprises DABSYL and said 3' ligation moiety comprises phosphorothioate.

10. The method of claim 1, wherein said 3' ligation moiety comprises DABSYL.

11. The method of claim 1, wherein said sample was collected into a buffer comprising guanidinium hydrochloride (GuHCl).

12. The method of claim 11, wherein said sample is blood.

13. The method of claim 1, wherein said target nucleic acids comprise RNA.

14. The method of claim 1, wherein said detecting step (f) utilizes a technique selected from the group consisting of capillary electrophoresis, mass spectrometry, microarray analysis, sequencing, real-time PCR, optical detection, fluorescence detection, bioluminescence detection, chemiluminescence detection, electrochemical detection, electrochemiluminescence detection and lateral flow detection.

15. The method of claim 1, wherein said hybridizing step (c) occurs simultaneously with said ligating step (b).

16. A method for detecting a plurality of target RNA sequences in a sample, wherein each target nucleic acid sequence comprises an adjacent first and second target domain and a third target domain, said method comprising:
(a) collecting a sample into a buffer to form a stabilized sample;
(b) conducting an assay in accordance with claim 1 in said stabilized sample to detect said plurality of target nucleic acids.

17. The method of claim 16, wherein said sample is stable for at least 1 week at ambient room temperature.

* * * * *

SEQUENCE LISTING

<160> NUMBER OF SEQ ID NOS: 56

<210> SEQ ID NO 1
<211> LENGTH: 19
<212> TYPE: DNA
<213> ORGANISM: Artificial Sequence
<220> FEATURE:
<223> OTHER INFORMATION: Synthetic Primer

<400> SEQUENCE: 1
gggttcccta agggttgga        19

<210> SEQ ID NO 2
<211> LENGTH: 23
<212> TYPE: DNA
<213> ORGANISM: Artificial Sequence
<220> FEATURE:
<223> OTHER INFORMATION: Synthetic Primer

<400> SEQUENCE: 2
gtgccagcaa gatccaatct aga        23

<210> SEQ ID NO 3
<211> LENGTH: 47
<212> TYPE: DNA
<213> ORGANISM: Artificial Sequence
<220> FEATURE:
<223> OTHER INFORMATION: Synthetic Probe

<400> SEQUENCE: 3
tacatccttc ctagtcaatt acactctaga ttggatcttg ctggcac        47

<210> SEQ ID NO 4
<211> LENGTH: 41

```
<212> TYPE: DNA
<213> ORGANISM: Artificial Sequence
<220> FEATURE:
<223> OTHER INFORMATION: Synthetic Probe

<400> SEQUENCE: 4
gggttcccta agggttggat aggtaaatgg cagtgtagaa c                   41

<210> SEQ ID NO 5
<211> LENGTH: 46
<212> TYPE: DNA
<213> ORGANISM: Artificial Sequence
<220> FEATURE:
<223> OTHER INFORMATION: Synthetic Oligonucleotide

<400> SEQUENCE: 5
gtgtaattga ctaggaagga tgtagttcta cactgccatt taccta             46

<210> SEQ ID NO 6
<211> LENGTH: 46
<212> TYPE: RNA
<213> ORGANISM: Artificial Sequence
<220> FEATURE:
<223> OTHER INFORMATION: Synthetic Probe

<400> SEQUENCE: 6
guguaauuga cuaggaagga uguaguucua cacugccauu uaccua             46

<210> SEQ ID NO 7
<211> LENGTH: 45
<212> TYPE: DNA
<213> ORGANISM: Artificial Sequence
<220> FEATURE:
<223> OTHER INFORMATION: Synthetic Probe

<400> SEQUENCE: 7
tggtttggtg cttcaaatac tctctagatt ggatcttgct ggcac              45

<210> SEQ ID NO 8
<211> LENGTH: 63
<212> TYPE: DNA
<213> ORGANISM: Artificial Sequence
<220> FEATURE:
<223> OTHER INFORMATION: Synthetic Probe

<400> SEQUENCE: 8
gggttcccta agggttggat cgagtctaca gatccccaac tttcatagtc tgaaactttc    60
tcc                                                             63

<210> SEQ ID NO 9
<211> LENGTH: 42
<212> TYPE: DNA
<213> ORGANISM: Artificial Sequence
<220> FEATURE:
<223> OTHER INFORMATION: Synthetic Oligonucleotide

<400> SEQUENCE: 9
agtatttgaa gcaccaaacc aggagaaagt ttcagactat ga                  42

<210> SEQ ID NO 10
<211> LENGTH: 41
<212> TYPE: DNA
<213> ORGANISM: Artificial Sequence
<220> FEATURE:
<223> OTHER INFORMATION: Synthetic Probe
```

<400> SEQUENCE: 10
tagcagacac atccaggctc tagattggat cttgctggca c                41

<210> SEQ ID NO 11
<211> LENGTH: 55
<212> TYPE: DNA
<213> ORGANISM: Artificial Sequence
<220> FEATURE:
<223> OTHER INFORMATION: Synthetic Probe

<400> SEQUENCE: 11
gggttcccta agggttggat cgagtctact ccaactttga ccaccattcg gctac                55

<210> SEQ ID NO 12
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 12
gcctggatgt gtctgctagt agccgaatgg tggtca                36

<210> SEQ ID NO 13
<211> LENGTH: 36
<212> TYPE: RNA
<213> ORGANISM: Artificial Sequence
<220> FEATURE:
<223> OTHER INFORMATION: Synthetic Oliogonucleotide

<400> SEQUENCE: 13
gccuggaugu gucugcuagu agccgaaugg ugguca                36

<210> SEQ ID NO 14
<211> LENGTH: 38
<212> TYPE: DNA
<213> ORGANISM: Artificial Sequence
<220> FEATURE:
<223> OTHER INFORMATION: Synthetic Probe

<400> SEQUENCE: 14
tccgagattt cccctctag attggatctt gctggcac                38

<210> SEQ ID NO 15
<211> LENGTH: 37
<212> TYPE: DNA
<213> ORGANISM: Artificial Sequence
<220> FEATURE:
<223> OTHER INFORMATION: Synthetic Probe

<400> SEQUENCE: 15
gggttcccta agggttggat cccagactcc tccctct                37

<210> SEQ ID NO 16
<211> LENGTH: 32
<212> TYPE: DNA
<213> ORGANISM: Artificial Sequence
<220> FEATURE:
<223> OTHER INFORMATION: Synthetic Oliogonucleotide

<400> SEQUENCE: 16
gggggaaatc tcggaagagg gaggagtctg gg                32

<210> SEQ ID NO 17
<211> LENGTH: 39

```
<212> TYPE: DNA
<213> ORGANISM: Artificial Sequence
<220> FEATURE:
<223> OTHER INFORMATION: Synthetic Probe

<400> SEQUENCE: 17
tcacggtctg ccacgctcta gattggatct tgctggcac                           39

<210> SEQ ID NO 18
<211> LENGTH: 53
<212> TYPE: DNA
<213> ORGANISM: Artificial Sequence
<220> FEATURE:
<223> OTHER INFORMATION: Synthetic Probe

<400> SEQUENCE: 18
gggttcccta agggttggat gagtctacat gatccttccc gccacaaaga tgg           53

<210> SEQ ID NO 19
<211> LENGTH: 32
<212> TYPE: DNA
<213> ORGANISM: Artificial Sequence
<220> FEATURE:
<223> OTHER INFORMATION: Synthetic Oliogonucleotide

<400> SEQUENCE: 19
cgtggcagac cgtgaccatc tttgtggcgg ga                                  32

<210> SEQ ID NO 20
<211> LENGTH: 51
<212> TYPE: DNA
<213> ORGANISM: Artificial Sequence
<220> FEATURE:
<223> OTHER INFORMATION: Synthetic Probe

<400> SEQUENCE: 20
gggttcccta agggttggac ggacgcctgc ttcaccacct tcttgatgtc a             51

<210> SEQ ID NO 21
<211> LENGTH: 32
<212> TYPE: DNA
<213> ORGANISM: Artificial Sequence
<220> FEATURE:
<223> OTHER INFORMATION: Synthetic Probe

<400> SEQUENCE: 21
tcatatttgg caggttttc tagacggcag gt                                   32

<210> SEQ ID NO 22
<211> LENGTH: 50
<212> TYPE: DNA
<213> ORGANISM: Artificial Sequence
<220> FEATURE:
<223> OTHER INFORMATION: Synthetic Probe

<400> SEQUENCE: 22
caggtccacc actgacacgt tggcagttct agattggatc ttgctggcac               50

<210> SEQ ID NO 23
<211> LENGTH: 20
<212> TYPE: DNA
<213> ORGANISM: Artificial Sequence
<220> FEATURE:
<223> OTHER INFORMATION: Synthetic Primer

<400> SEQUENCE: 23
```
attaaccctc actaaaggga					20

<210> SEQ ID NO 24
<211> LENGTH: 89
<212> TYPE: DNA
<213> ORGANISM: Artificial Sequence
<220> FEATURE:
<223> OTHER INFORMATION: Synthetic Oligonucleotide

<400> SEQUENCE: 24
actgccaacg tgtcagtggt ggacctgacc tgccgtctag aaaaacctgc caaatatgat		60 gacatcaaga aggtggtgaa gcaggcgtc					89

<210> SEQ ID NO 25
<211> LENGTH: 76
<212> TYPE: DNA
<213> ORGANISM: Artificial Sequence
<220> FEATURE:
<223> OTHER INFORMATION: Synthetic Probe

<400> SEQUENCE: 25
ttttctagac ggcaggtcag gtccaccaga tgatcgacga gacactctcg ccatctagat		60 tggatcttgc tggcac					76

<210> SEQ ID NO 26
<211> LENGTH: 79
<212> TYPE: DNA
<213> ORGANISM: Artificial Sequence
<220> FEATURE:
<223> OTHER INFORMATION: Synthetic Probe

<400> SEQUENCE: 26
gggttcccta agggttggac ggaccaactc ctcgccatat catctgtaca ccttcttgat		60 gtcatcatat ttggcaggt					79

<210> SEQ ID NO 27
<211> LENGTH: 35
<212> TYPE: DNA
<213> ORGANISM: Artificial Sequence
<220> FEATURE:
<223> OTHER INFORMATION: Synthetic Probe

<400> SEQUENCE: 27
ccaactcctc gccatatcat ctgtacacct tcttg					35

<210> SEQ ID NO 28
<211> LENGTH: 78
<212> TYPE: DNA
<213> ORGANISM: Artificial Sequence
<220> FEATURE:
<223> OTHER INFORMATION: Synthetic Probe

<400> SEQUENCE: 28
tgctgatgat cttgaggctg ttgtcatact gatgatcgac gagacactct cgccatctag		60 attggatctt gctggcac					78

<210> SEQ ID NO 29
<211> LENGTH: 75
<212> TYPE: DNA
<213> ORGANISM: Artificial Sequence
<220> FEATURE:
<223> OTHER INFORMATION: Synthetic Probe

<400> SEQUENCE: 29

```
gggttccctaagggttggacgatggagttgatgctgacggaagtcatagtaagcagttgg      60 tggtgcaggaggcat                                                    75
```

<210> SEQ ID NO 30
<211> LENGTH: 30
<212> TYPE: DNA
<213> ORGANISM: Artificial Sequence
<220> FEATURE:
<223> OTHER INFORMATION: Synthetic Probe

<400> SEQUENCE: 30

```
tgctgacggaagtcatagtaagcagttggt                                     30
```

<210> SEQ ID NO 31
<211> LENGTH: 77
<212> TYPE: DNA
<213> ORGANISM: Artificial Sequence
<220> FEATURE:
<223> OTHER INFORMATION: Synthetic Probe

<400> SEQUENCE: 31

```
tccttgagtgcctccaacaccttcttgaggatgatcgacgagacactctcgccatctaga      60 ttggatcttgctggcac                                                  77
```

<210> SEQ ID NO 32
<211> LENGTH: 77
<212> TYPE: DNA
<213> ORGANISM: Artificial Sequence
<220> FEATURE:
<223> OTHER INFORMATION: Synthetic Probe

<400> SEQUENCE: 32

```
tccttgagtgcctccaacaccttcttgaggatgatcgacgagacactctcgccatctaga      60 ttggatcttgctggcac                                                  77
```

<210> SEQ ID NO 33
<211> LENGTH: 33
<212> TYPE: DNA
<213> ORGANISM: Artificial Sequence
<220> FEATURE:
<223> OTHER INFORMATION: Synthetic Probe

<400> SEQUENCE: 33

```
ctgacgactcttaatatcccagcaggcctcgtt                                  33
```

<210> SEQ ID NO 34
<211> LENGTH: 78
<212> TYPE: DNA
<213> ORGANISM: Artificial Sequence
<220> FEATURE:
<223> OTHER INFORMATION: Synthetic Probe

<400> SEQUENCE: 34

```
ttagttccaagataaccttggttccaggctgatgatcgacgagacactctcgccatctag      60 attggatcttgctggcac                                                 78
```

<210> SEQ ID NO 35
<211> LENGTH: 79
<212> TYPE: DNA
<213> ORGANISM: Artificial Sequence
<220> FEATURE:
<223> OTHER INFORMATION: Synthetic Probe

<400> SEQUENCE: 35 gggttccta agggttggac gttagacgcc aataggagtt tcactggtgg ctaccaccca    60
ctgagaggag aaaagtcat                                                79

<210> SEQ ID NO 36
<211> LENGTH: 30
<212> TYPE: DNA
<213> ORGANISM: Artificial Sequence
<220> FEATURE:
<223> OTHER INFORMATION: Synthetic Probe

<400> SEQUENCE: 36
cgccaatagg agtttcactg gtggctacca                                    30

<210> SEQ ID NO 37
<211> LENGTH: 30
<212> TYPE: DNA
<213> ORGANISM: Artificial Sequence
<220> FEATURE:
<223> OTHER INFORMATION: Synthetic Probe

<400> SEQUENCE: 37
gccagagagg ttacgtggcg gctctcttca                                    30

<210> SEQ ID NO 38
<211> LENGTH: 58
<212> TYPE: DNA
<213> ORGANISM: Artificial Sequence
<220> FEATURE:
<223> OTHER INFORMATION: Synthetic Probe

<400> SEQUENCE: 38
ggatgctatg agcgatctgc agcgtgcagt cttcacatct tcccagtcca gtttgacg     58

<210> SEQ ID NO 39
<211> LENGTH: 79
<212> TYPE: DNA
<213> ORGANISM: Artificial Sequence
<220> FEATURE:
<223> OTHER INFORMATION: Synthetic Probe

<400> SEQUENCE: 39
tctggaacct catcttctgg ctctggatcc ttcctaagtg aatgttgaca ggatgctcta   60
gattggatct tgctggcac                                                79

<210> SEQ ID NO 40
<211> LENGTH: 30
<212> TYPE: DNA
<213> ORGANISM: Artificial Sequence
<220> FEATURE:
<223> OTHER INFORMATION: Synthetic Probe

<400> SEQUENCE: 40
tcttcatcct cgatcttggg agccaagtag                                    30

<210> SEQ ID NO 41
<211> LENGTH: 76
<212> TYPE: DNA
<213> ORGANISM: Artificial Sequence
<220> FEATURE:
<223> OTHER INFORMATION: Synthetic Probe

<400> SEQUENCE: 41
ggatgctatg agcgatctgc agccactata catcttacta tactttactc tacaacaagg   60
ggtacatctg cagaca                                                        76

<210> SEQ ID NO 42
<211> LENGTH: 70
<212> TYPE: DNA
<213> ORGANISM: Artificial Sequence
<220> FEATURE:
<223> OTHER INFORMATION: Synthetic Probe

<400> SEQUENCE: 42
tactgagtgt caccgttgaa gagagtggag tggcttttgt aaagtcttct agattggatc        60
ttgctggcac                                                               70

<210> SEQ ID NO 43
<211> LENGTH: 29
<212> TYPE: DNA
<213> ORGANISM: Artificial Sequence
<220> FEATURE:
<223> OTHER INFORMATION: Synthetic Probe

<400> SEQUENCE: 43
agagtgatcg gtattttgtt ctctgttca                                          29

<210> SEQ ID NO 44
<211> LENGTH: 86
<212> TYPE: DNA
<213> ORGANISM: Artificial Sequence
<220> FEATURE:
<223> OTHER INFORMATION: Synthetic Probe

<400> SEQUENCE: 44
ggatgctatg agcgatctgc agcgcaattc atttcattca caatcaatct aaagatctcc        60
ttaaacaacg ctttgtattc tggagg                                             86

<210> SEQ ID NO 45
<211> LENGTH: 101
<212> TYPE: DNA
<213> ORGANISM: Artificial Sequence
<220> FEATURE:
<223> OTHER INFORMATION: Synthetic Probe

<400> SEQUENCE: 45
tgttgtaggg gaactcacgg gctctgggtt gacagaggcc agttaggatg ttaccaccag        60
tgaatgttga caggatcctc tagattggat cttgctggca c                           101

<210> SEQ ID NO 46
<211> LENGTH: 64
<212> TYPE: DNA
<213> ORGANISM: Artificial Sequence
<220> FEATURE:
<223> OTHER INFORMATION: Synthetic Probe

<400> SEQUENCE: 46
tccattgatg acaagcttcc cgttctcagc tcgcgttcta agcttccctt tagtgagggt        60
taat                                                                     64

<210> SEQ ID NO 47
<211> LENGTH: 76
<212> TYPE: DNA
<213> ORGANISM: Artificial Sequence
<220> FEATURE:
<223> OTHER INFORMATION: Synthetic Probe

```
<400> SEQUENCE: 47
taatacgact cactataggg cgagtagaaa gttgaaattg attatgatct cgctcctgga    60
agatggtgat gggatt                                                   76

<210> SEQ ID NO 48
<211> LENGTH: 55
<212> TYPE: DNA
<213> ORGANISM: Artificial Sequence
<220> FEATURE:
<223> OTHER INFORMATION: Synthetic Probe

<400> SEQUENCE: 48
ttctcccagt gactgagggc tggtgtgtct ttggctccct ttagtgaggg ttaat         55

<210> SEQ ID NO 49
<211> LENGTH: 76
<212> TYPE: DNA
<213> ORGANISM: Artificial Sequence
<220> FEATURE:
<223> OTHER INFORMATION: Synthetic Probe

<400> SEQUENCE: 49
taatacgact cactataggg cgaattgaga aagagataaa tgatagggac tggagcaccg    60
agggtatgag aggttc                                                   76

<210> SEQ ID NO 50
<211> LENGTH: 55
<212> TYPE: DNA
<213> ORGANISM: Artificial Sequence
<220> FEATURE:
<223> OTHER INFORMATION: Synthetic Probe

<400> SEQUENCE: 50
ttcaactcct tggctagtac acttcggtct agcgctccct ttagtgaggg ttaat         55

<210> SEQ ID NO 51
<211> LENGTH: 78
<212> TYPE: DNA
<213> ORGANISM: Artificial Sequence
<220> FEATURE:
<223> OTHER INFORMATION: Synthetic Probe

<400> SEQUENCE: 51
taatacgact cactataggg cggtaagagt attgaaatta gtaagaggtc tccatgccga    60
aacaccaaag tcacaaac                                                 78

<210> SEQ ID NO 52
<211> LENGTH: 52
<212> TYPE: DNA
<213> ORGANISM: Artificial Sequence
<220> FEATURE:
<223> OTHER INFORMATION: Synthetic Probe

<400> SEQUENCE: 52
tgtgcatctc aaagccatct gctgtcttcg gctcccttta gtgagggtta at            52

<210> SEQ ID NO 53
<211> LENGTH: 76
<212> TYPE: DNA
<213> ORGANISM: Artificial Sequence
<220> FEATURE:
<223> OTHER INFORMATION: Synthetic Probe

<400> SEQUENCE: 53
```

```
taatacgact cactataggg cgtttgttgt taagtatgtg atttagggag gaagtgaccc      60
aagtggttga ctccta                                                     76

<210> SEQ ID NO 54
<211> LENGTH: 59
<212> TYPE: DNA
<213> ORGANISM: Artificial Sequence
<220> FEATURE:
<223> OTHER INFORMATION: Synthetic Probe

<400> SEQUENCE: 54
tgttctctgc ttcttccttc aactgaatct cctcctgctt ccctttagtg agggttaat     59

<210> SEQ ID NO 55
<211> LENGTH: 73
<212> TYPE: DNA
<213> ORGANISM: Artificial Sequence
<220> FEATURE:
<223> OTHER INFORMATION: Synthetic Probe

<400> SEQUENCE: 55
taatacgact cactataggg tatttgataa gagaatgaag aagtatccac gtccgctcgg    60
aaggcagcca aat                                                       73

<210> SEQ ID NO 56
<211> LENGTH: 20
<212> TYPE: DNA
<213> ORGANISM: Artificial Sequence
<220> FEATURE:
<223> OTHER INFORMATION: Synthetic Primer

<400> SEQUENCE: 56
taatacgact cactataggg                                                20
```